United States Patent
Bignell et al.

(10) Patent No.: US 10,457,985 B2
(45) Date of Patent: *Oct. 29, 2019

(54) METHODS FOR INDEXING SAMPLES AND SEQUENCING MULTIPLE POLYNUCLEOTIDE TEMPLATES

(71) Applicant: Illumina Cambridge Limited, Nr Saffron Walden (GB)

(72) Inventors: Helen Bignell, Cambridge (GB); Louise Fraser, Cambridge (GB); Niall Anthony Gormley, Cambridge (GB)

(73) Assignee: Illumina Cambridge Limited, Cambridge (GB)

( * ) Notice: Subject to any disclaimer, the term of this patent is extended or adjusted under 35 U.S.C. 154(b) by 108 days.

This patent is subject to a terminal disclaimer.

(21) Appl. No.: 15/365,266

(22) Filed: Nov. 30, 2016

(65) Prior Publication Data

US 2017/0145499 A1 May 25, 2017

Related U.S. Application Data

(60) Division of application No. 14/307,254, filed on Jun. 17, 2014, now Pat. No. 9,512,478, which is a continuation of application No. 13/444,136, filed on Apr. 11, 2012, now Pat. No. 8,822,150, which is a continuation of application No. 13/219,923, filed on Aug. 29, 2011, now abandoned, which is a continuation of application No. 12/012,613, filed on Feb. 4, 2008, now Pat. No. 8,053,192.

(60) Provisional application No. 60/899,221, filed on Feb. 2, 2007.

(51) Int. Cl.
| | |
|---|---|
| C12Q 1/68 | (2018.01) |
| C12P 19/34 | (2006.01) |
| C12Q 1/6874 | (2018.01) |
| C12Q 1/6837 | (2018.01) |
| C12Q 1/6855 | (2018.01) |
| C12Q 1/6869 | (2018.01) |

(52) U.S. Cl.
CPC ......... *C12Q 1/6874* (2013.01); *C12Q 1/6837* (2013.01); *C12Q 1/6855* (2013.01); *C12Q 1/6869* (2013.01)

(58) Field of Classification Search
None
See application file for complete search history.

(56) References Cited

U.S. PATENT DOCUMENTS

| | | | |
|---|---|---|---|
| 4,719,179 A | 1/1988 | Barany | |
| 5,093,245 A | 3/1992 | Keith et al. | |
| 5,302,509 A | 4/1994 | Cheeseman | |
| 5,326,692 A | 7/1994 | Brinkley et al. | |
| 5,405,746 A | 4/1995 | Uhlen | |
| 5,436,142 A | 7/1995 | Wigler et al. | |
| 5,474,796 A | 12/1995 | Brennan | |
| 5,508,169 A | 4/1996 | Deugau et al. | |
| 5,514,539 A | 5/1996 | Bukh et al. | |
| 5,547,839 A | 8/1996 | Dower et al. | |
| 5,589,332 A | 12/1996 | Shih et al. | |
| 5,616,478 A | 4/1997 | Chetverin | |
| 5,629,158 A | 5/1997 | Uhlen | |
| 5,641,658 A | 6/1997 | Adams et al. | |
| 5,645,801 A | 7/1997 | Bouma et al. | |
| 5,645,994 A | 7/1997 | Huang | |
| 5,683,872 A | 11/1997 | Rudert et al. | |
| 5,690,894 A | 11/1997 | Pinkel et al. | |
| 5,750,337 A | 5/1998 | Squirrell et al. | |
| 5,753,439 A | 5/1998 | Smith et al. | |
| 5,759,822 A | 6/1998 | Chenchik et al. | |
| 5,795,714 A | 8/1998 | Cantor et al. | |
| 5,800,992 A | 9/1998 | Fodor et al. | |
| 5,830,663 A | 11/1998 | Embleton et al. | |
| 5,837,466 A | 11/1998 | Lane et al. | |
| 5,843,660 A | 12/1998 | Schumm et al. | |
| 5,849,542 A | 12/1998 | Reeve et al. | |
| 5,922,574 A | 7/1999 | Minter | |
| 5,939,291 A | 8/1999 | Loewy et al. | |
| 5,942,391 A | 8/1999 | Zhang et al. | |
| 5,976,802 A | 11/1999 | Ansorge et al. | |
| 6,033,881 A | 3/2000 | Himmler et al. | |
| 6,045,994 A | 4/2000 | Zabeu et al. | |
| 6,054,276 A | 4/2000 | Macevicz | |
| 6,060,288 A | 5/2000 | Adams et al. | |

(Continued)

FOREIGN PATENT DOCUMENTS

| | | |
|---|---|---|
| DE | 4141178 | 6/1993 |
| EP | 0 224 126 | 6/1987 |

(Continued)

OTHER PUBLICATIONS

"Figure 1D from U.S. Pat. No. 6,060,288 with Examiner handwritings (in U.S. Appl. No. 10/449,010)", Sep. 26, 2006.

(Continued)

*Primary Examiner* — Young J Kim
(74) *Attorney, Agent, or Firm* — Illumina, Inc.

(57) ABSTRACT

The invention relates to methods for indexing samples during the sequencing of polynucleotide templates, resulting in the attachment of tags specific to the source of each nucleic acid sample such that after a sequencing run, both the source and sequence of each polynucleotide can be determined. Thus, the present invention pertains to analysis of complex genomes (e.g., human genomes), as well as multiplexing less complex genomes, such as those of bacteria, viruses, mitochondria, and the like.

18 Claims, 11 Drawing Sheets

Specification includes a Sequence Listing.

(56) References Cited

U.S. PATENT DOCUMENTS

| | | | |
|---|---|---|---|
| 6,090,592 | A | 7/2000 | Adams et al. |
| 6,107,023 | A | 8/2000 | Reyes et al. |
| 6,114,149 | A | 9/2000 | Fry et al. |
| 6,261,770 | B1 | 7/2001 | Warthoe |
| 6,277,606 | B1 | 8/2001 | Wigler et al. |
| 6,280,949 | B1 | 8/2001 | Lizardi |
| 6,287,825 | B1 | 9/2001 | Weissman et al. |
| 6,316,229 | B1 | 11/2001 | Lizardi et al. |
| 6,322,971 | B1 | 11/2001 | Chetverin et al. |
| 6,326,489 | B1 | 12/2001 | Church et al. |
| 6,361,947 | B1 | 3/2002 | Dong et al. |
| 6,372,434 | B1 | 4/2002 | Weissman et al. |
| 6,380,378 | B1 | 4/2002 | Kitamura et al. |
| 6,395,887 | B1 | 5/2002 | Weissman et al. |
| 6,406,893 | B1 | 6/2002 | Knapp et al. |
| 6,432,680 | B1 | 8/2002 | Lin et al. |
| 6,468,751 | B1 | 10/2002 | Adams et al. |
| 6,489,103 | B1 | 12/2002 | Griffiths et al. |
| 6,511,803 | B1 | 1/2003 | Church et al. |
| 7,033,764 | B2 | 4/2006 | Korlach et al. |
| 7,115,400 | B1 | 10/2006 | Adessi et al. |
| 7,323,305 | B2 | 1/2008 | Leamon et al. |
| 8,053,192 | B2 | 11/2011 | Bignell et al. |
| 8,182,989 | B2 | 5/2012 | Bignell et al. |
| 8,822,150 | B2 * | 9/2014 | Bignell ............... C12Q 1/6874 435/6.11 |
| 9,512,478 | B2 | 12/2016 | Bignell et al. |
| 2003/0082543 | A1 | 5/2003 | Su et al. |
| 2004/0067493 | A1 | 4/2004 | Matsuzaki et al. |
| 2004/0137473 | A1 | 7/2004 | Wigler et al. |
| 2005/0095645 | A1 | 5/2005 | Jones et al. |
| 2006/0008824 | A1 | 1/2006 | Ronaghi et al. |
| 2006/0188901 | A1 | 8/2006 | Barnes et al. |
| 2006/0263789 | A1 * | 11/2006 | Kincaid .................. C12Q 1/68 435/6.12 |
| 2009/0176662 | A1 | 7/2009 | Rigatti et al. |

FOREIGN PATENT DOCUMENTS

| | | |
|---|---|---|
| EP | 0 356 021 | 2/1990 |
| EP | 0 374 665 | 6/1990 |
| EP | 0487104 | 5/1992 |
| EP | 0 201 184 | 12/1992 |
| EP | 0543484 | 5/1993 |
| EP | 0 356 025 | 4/1994 |
| EP | 0 665 293 | 8/1995 |
| EP | 0701001 | 3/1996 |
| EP | 0 763 135 | 3/1997 |
| EP | 1 019 496 | 7/2000 |
| EP | 1 482 036 | 12/2004 |
| GB | 2233654 | 1/1991 |
| GB | 2412170 | 9/2005 |
| WO | 1987/06270 | 10/1987 |
| WO | 1988/10315 | 12/1988 |
| WO | 1989/01050 | 2/1989 |
| WO | 1989/09282 | 10/1989 |
| WO | 1989/12695 | 12/1989 |
| WO | 1990/02205 | 3/1990 |
| WO | 1990/06042 | 6/1990 |
| WO | 1990/09455 | 8/1990 |
| WO | 1990/11369 | 10/1990 |
| WO | 1991/06678 A1 | 5/1991 |
| WO | 1992/04469 | 3/1992 |
| WO | 1992/10587 | 6/1992 |
| WO | 1993/03151 | 2/1993 |
| WO | 1993/04199 | 3/1993 |
| WO | 1993/09250 | 5/1993 |
| WO | 1993/21340 | 10/1993 |
| WO | 1994/02634 | 2/1994 |
| WO | 1994/03624 | 2/1994 |
| WO | 1994/05414 | 3/1994 |
| WO | 1994/24312 | 10/1994 |
| WO | 1995/12416 | 5/1995 |
| WO | 1995/33073 | 12/1995 |
| WO | 1996/04404 | 2/1996 |
| WO | 1996/24688 | 8/1996 |
| WO | 1996/27025 | 9/1996 |
| WO | 1996/32504 | 10/1996 |
| WO | 1996/34114 | 10/1996 |
| WO | 1996/36737 | 11/1996 |
| WO | 1997/04126 | 2/1997 |
| WO | 1997/19193 | 5/1997 |
| WO | 1997/41256 | 11/1997 |
| WO | 1997/45554 | 12/1997 |
| WO | 1997/47767 | 12/1997 |
| WO | 1998/36094 | 8/1998 |
| WO | 1998/44151 | 10/1998 |
| WO | 1998/44152 | 10/1998 |
| WO | 1998/45474 | 10/1998 |
| WO | 2000/18957 | 4/2000 |
| WO | 2000/23620 | 4/2000 |
| WO | 2000/41524 | 7/2000 |
| WO | 2000/47767 | 8/2000 |
| WO | 2000/75374 | 12/2000 |
| WO | 2003035841 | 5/2003 |
| WO | 2004/70007 | 8/2004 |
| WO | 2004/81183 | 9/2004 |
| WO | 2005/68656 | 7/2005 |
| WO | 2005/90599 | 9/2005 |
| WO | 2006/137734 | 12/2006 |
| WO | 2008/007951 | 1/2008 |

OTHER PUBLICATIONS

Abel, "Fiber-Optic Evanescent Wave Biosensor for the Detection of Oligonucleotides", Analytical Chemistry, vol. 68, Sep. 1996, 2905-2912.

Adessi, et al., "Solid Phase DNA amplification: characterisation of primer attachment and amplification mechanisms", Nucleic Acids Research 28, 2000, 1-8.

Babic, et al., "MutS interaction with mismatch and alkylated base containing DNA molecules detected by optical biosensor", Mutation Research 372:87-96, 1996.

Beattie, et al., "Hybridization of DNA targets to glass-tethered oligonucleotide probes", Molecular Biotechnology, 4, 1995, 213-225.

Binladen, Jonas et al., "The use of coded PCR primers enables high-throughput sequencing of multiple homolog amplification products by 454 parallel sequencing", Plos One vol. 2 No. 2, 2007, E197.

Blanchard, et al., "Oligonucleotide array synthesis using ink jets", Genome Science and Technology 1(3):225, 1996.

Bronk, et al., "Combined imaging and chemical sensing using a single optical imaging fiber.", Anal. Chem. 67:2750-2757, 1995.

Chang, et al., "PCR Amplification of Chromosome-specific DNA Isolated from Flow Cytometry-Sorted Chromosomes", Genomics 12, 1992, 307-312.

Chee, et al., "Accessing genetic information with high-density DNA arrays", Science 274 (5287), 2001, 601.

Chen, et al., "Isolation of Plasmid DNA Rescued from Single Colonies of Agrobacterium Tumefaciens by Means of Rolling Circle Amplification", Plant Molecular Biology Reporter, 21, 411-415, 2003, 5.

Chenchik, et al., "Full length cDNA cloning", BioTechniques vol. 21, 1996, 526-534.

Cheng, et al., "Chip PCR II Investigation of different PCR amplification systems in microfabricated silicon-glass chips", Nucleic Acids Research 24, 1996, 380-385.

Chrisey, et al., "Covalent attachment of synthetic DNA to self-assembled monolayer films", NAR, 24(15), 1996, 3031-3039.

Chu, et al., "Derivitization of unprotected polynucleotides", NAR, 11 (18), 1983, 6514-6529.

Drmanac, et al., "Sequencing by hybridization: towards an automated sequencing of one million m13 clones arrayed on membranes", Electrophoresis 13, 1992, 566-573.

Dubiley, et al., "Polymorphism analysis and gene detection by minisequencing on an array of gel-immobilized primers", Nucleic Acids Research 27,1999, 1-6.

(56) References Cited

OTHER PUBLICATIONS

Egan, et al., "Structural studies and chemistry of bacterial polysaccharides. Investigations of Phosphodiester-Linked Capsular Polysaccharides Isolated from Haemophilus influenzae Types a, b, c, and f: NMR Spectroscopic Identification and Chemical Modification of End", Groups and the Nature of Base-Catalyzed Hydrolytic Depolymerization, J. Am. Chem. Soc., 104, 1982, 2898-2910.
Eggleston, et al., "A helicase assay based on the displacement of fluorescent nucleic acid-binding ligands", Nucleic Acids Research 24(7), 1996, 1179-1186.
Ferguson, J A. et al., "A Fiber-Optic DNA Biosensor Microarray for the Analysis of Gene Expression", Nature Biotechnol. vol. 14, 1996, 1681-1684.
Fodor, et al., "Light-Directed, Spatially Addressable Parallel Chemical Synthesis", Science, vol. 251, 1991, 767-773.
Fu, et al., "Sequencing Double-stranded DNA by Strand Displacement", Nucleic Acids Research vol. 25 No. 3, 1997, 677-679.
Ghosh, et al., "Covalent attachment of oligonucleotides to solid supports", NAR, 15 (13), 1987, 5353-5371.
Gilham, "The synthesis of Celluloses covalently bound nucleotides, polynucleotides, and nucleic acids", Biochemistry, 1968, 2810-2813.
Gingeras, et al., "Hybridization properties of immobilized nucleic acids", NAR, 15, 1987, 5373-5390.
Gubler, et al., "A simple and very efficient method for generating cDNA Libraries", Gene 25, 1983, 263-269.
Guo, Zhen et al., "Direct fluorescence analysis of genetic polymorphisms by hybridization with oligonucleotide arrays on glass supports", Nucleic Acids Research, vol. 22(24), 1994, 5456-5465.
Hafner, et al., "Identification of microRNAs and other small regulatory RNAs using cDNA library sequencing", Methods: A companion to methods in Enzymology, Academic press Inc, New York, US vol. 44 No. 1, 2007, 3-12.
Hahn, et al., "Quantitative polymerase chain reaction with enzyme-linked immunosorbent assay detection of selectively digested amplified sample and control DNA", Anal Biochem 229, 1995, 236-248.
Helfman, et al., "Identification of clones that encode chicken tropomyosin by direct immunological screening of a cDNA expression library", PNAS US 80,1983, 31-35.
Higuchi, et al., "Kinetic PCR analysis: real-time monitoring of DNA amplification reactions", Bio/Technology 11:1026-1030, 1993.
Johnson, "Molecular Cloning of DNA from specific chromosomal regions by Microdissection and Sequence-Independent Amplification of DNA", Genomics 6, 1990, 243-251.
Joos, et al., "Covalent attachment of hybridizable oligonucleotides to glass supports", Analytical Biochemistry, 247, 1997, 96-101.
Kalisch, et al., "Covalently linked sequencing primer linkers (splinkers) for sequence analysis of restriction fragments", Gene 44, 1986, 263-270.
Kaneoka, et al., "Solid-phase direct DNA sequencing of allele specific polymerase chain reaction amplified HLA-DR genes", Biotechniques 10(1):30, 32, 34, 1991.
Kimmel, et al., "Preparation of cDNA and the Generation of cDNA Libraries: Overview", Methods in Enzymology 152, 1987, 307-316.
Kinzler, et al., "Whole genome PCR: application to the identification of sequences bound by gene regulatory proteins", Nucleic Acids Research, 17(10), 1989, 3645-3653.
Kremsky, et al., "Immobilization of DNA oligonucelotides containing an aldehyde or carboxylic acid group at the 5' terminus", NAR 15 (7), 1987, 2891-2909.
Kulp, et al., "Polymer immobilized enzyme optrodes for the detection of penicillin", Anal. Chem. 59:2849-2853, 1987.
Lambert et al., "cDNA library construction from small amounts of RNA using paramagnetic beads and PCR", Nucleic Acids Research 21(3):775-6, 1993.
Lamture, et al., "Direct Detection of Nucleic Acid Hybridization on the Surface of a Charge Coupled-Device", Nucleic Acids Research, 22(11), 1994, 2121-2125.
Lizardi, "Mutation detection and single-molecule counting using isothermal rolling-circle amplification", Nature Genetics, vol. 19, 1998, 225-232.
Lockhart, D J. et al., "Expression monitoring by hybridization to high-density oligonucleotide arrays", Nature Biotechnology, vol. 14 December, ISSN 1087-015.,1996, 1675-1680.
Lucito, et al., "Genetic analysis using genomic representations", PNAS, 95, 1998, 4487-4492.
Ludecke, et al., "Cloning defined regions of the human genome by microdissection of banded chromosomes and enzymatic amplification", Nature 338, 1989, 348-350.
Lund, et al., "Assessment of methods for covalent binding of nucleic acids to magnetic beads, Dynabeads, and the characteristics of the bound nucleic acids in hybridization reactions", NAR, 16 (22), 1988, 10860-10881.
Manley, et al., "DNA-dependent transcription of adenovirus genes in a soluble whole-cell extract", PNAS 77(7):3855-3859, 1980.
Maskos, et al., "Oligonucleotide Synthesis and Hybridisations on Glass Supports: A Novel Linker for Oligonucleotide Synthesis and Hybridisation Properties of Oligonucleotides Synthesized in Situ", Nucleic Acids Research, 20(7), 1992, 1679-1684.
Maskos, et al., "Parallel analysis of oligodeoxyribonucleotide (oligonucleotide) interaction. I. Analysis of factors influencing oligonucleotide duplex formation", Nucleic Acids Research 20(7):1675-1678, 1992.
Matsunaga, et al., "Selecting and amplifying one fragment from a DNA fragment mixture by polyermerase chain reaction with a pair of selective primers", Electrophoresis, vol. 17, 1996, 1833-1840.
Matsuzaki, "Parallel Genotyping of Over 10,000 SNPs Using a One-Primer Assay on a High-Density Oligonucleotide Array", Genome Research, 14, 2004, 414-425.
Meyer, Matthias et al., "Parallel tagged sequencing on the 454 platform", Nature protocols vol. 3 No. 2, 2008, 267-278.
Meyer, Matthias et al., "Targeted high-throughput sequencing of tagged nucleic acid samples", Nucleic Acids Research vol. 35 No. 15, 2007, e97.
Mueller, et al., "In Vivo Footprinting of a muscle specific Enhancer by Ligation Mediated PCR", Science 246, 1989, 780-786.
Munkholm, C. et al., "Polymer modification of fiber optical imaging fibers", Analytical Chemistry vol. 58 No. 7, 1986, 1427-1430.
Nielsen, Kare et al., "DeepSAGE—digital transcriptomics with high sensitivity, simple experimental protocol and multiplexing of samples", Nucleic Acids Research vol. 34 No. 19, 2006, e133 (5 pages).
Notomi, et al., "Loop-mediated isothermal amplification of DNA", Nucleic Acids Research 28, 2000, i-vii.
Nussbaum, et al., "Isolation of anonymous DNA Sequences from within a submicroscopic X chromosomal deletion in a patient with choroideremia, deafness and mental retardation", PNAS US 84, 1987, 6521-6525.
Ochman, et al., "Genetic applications of an Inverse Polymerase Chain Reaction", Genetics 120, 1988, 621-623.
O'Donnell-Maloney, et al., "The development of microfabricated array for DNA sequencing and analysis", Tibtech, 14, 1996, 401-407.
Oliphant, et al., "Cloning of random-sequence oligodeoxynucleotides", Gene 44, 1986, 177-183.
Oroskar et al., "Detection of immobilized amplicons by ELISA-like techniques", Clinical Chemistry 42, 1996, 1547-1555.
Parameswaran, P. et al., "A Pyrosequencing-tailored nucleotide barcode design unveils opportunities for large-scale sample multiplexing", Nucleic Acids Research vol. 35 No. 19, 2007, e130.
Pease, et al., "Light-generated oligonucleotide array for rapid DNA sequence analysis", Proc. Natl. Acad. Sci., vol. 91, Issue 11, 1994, 5502-5026.
Peeters, et al., "Comparison of four biofunctional reagents for coupling peptides to proteins and the effect of the three moities on the immunogenicity of the conjugates", Journal of Immunological Methods, 120, 1989, 133-143.
Pfeifer, et al., "Genomic Sequencing and Methylation Analysis by Ligation Mediated PCR", Science 246, 1989, 810-813.

(56) References Cited

OTHER PUBLICATIONS

Pirrung, et al., "Comparison of Methods for Photochemical Phosphoramidite-Based DNA Synthesis", Journal of Organic Chemistry, 60(20), 1995, 6270-6276.
Piunno, et al., "Fiber-optic DNA sensor for fluorometric nucleic acid determination", Anal. Chem. 67:2635-2643, Aug. 1995.
Prashar, Y. et al., "Analysis of differential gene expression by display of 3' end restriction fragments of cDNAs", Proc. of the Nat Acad of Sciences, US vol. 93, 1996, 659-663.
Rasmussen, et al., "Covalent immobilization of DNA onto polystyrene microwells: The molecules are only bound at th e5' end", Analytical Biochemistry, 198, 1991, 138-142.
Saiki, et al., "Analysis of enzymatically amplified . . . -globin and HLA-DQ . . . DNA with allele-specific oligonucleotide probes", Nature 324, 1986, 163-166.
Saiki, et al., "Enzymatic amplification of B-globin genomic sequences and restriction site analysis for diagnosis of sickel cell anemia", Science, 230, 1985, 1350-1354.
Saiki, et al., "Genetic analysis of amplified DNA with immobilized sequence-specific oligonucleotide probes", PNAS 86:6230-4, 1989.
Saiki, et al., "Primer-Directed Enzymatic Amplification of DNA with a Thermostable DNA Polymerase", Science 239, 1988, 487-491.
Sanger, et al., "Cloning in Single-Stranded Bacteriophage as an Aid to Rapid DNA Sequencing", Mol Biology 143, 1980, 161-178.
Saunders, et al., "PCR amplification of DNA microdissected from a single polytene chromosome band: a comparison with conventional microcloning", Nucleic Acids Research 17, 1989, 9027-9037.
Shendure, et al., "Accurate Multiplex Polony Sequencing of an Evolved Bacterial Genome", Science, vol. 309, Sep. 9, 2005, 1728-1732.
Stamm, et al., "Sanchored PCR: PCR with cDNA couples to a solid phase", Nucleic Acids Research 19(6):1350, 1991.
Steigerwald, et al., "Ligation-mediated PCR Improves the sensitivity of methylation analysis by restriction enzymes and detection of specific DNA Strand breaks", Nucleic Acids Research 18, 1990, 1435-1439.
Sterky, et al., "Direct sequencing of bacterial artificial chromosomes [bacS] prokaryotic genomes by biotin capture PCR", Journal of Biotechnology, vol. 60, 1998, 119-129.
Strick, et al., "Stress-Induced Structural Transitions of DNA and Proteins", Annu Rev. Biophys. Biomol. Struct. 29, 2000, 523-543.
Thomas, et al., "Affymetrix: Genes on Chips", Expr. Opino. Ther. Patents, 8, 1998, 503-508.
Triglia, et al., "A procedure for in vitro amplification of DNA segments that lie outside the boundaries of know sequences", Nucleic Acids Research 16, 1988, 8186.
Vanness, et al., "A versatile solid support system for oligodeoxynucleotide probe-based hybridization assays", Nucleic Acids Research 19(12):3345-3350, 1991.
Velculescu, et al., "Serial analysis of gene expression", Science, 270, 1995, 484-487.
Vos, et al., "AFLP: a new technique for DNA Fingerprinting", NAR vol. 23 No. 21, 1995, 4407-4414.
Walker, "Empirical Aspects of Strand Displacement Amplification", PCR Methods Appl 3, 1993, 1-6.
Walker, et al., "Isothermal in vitro amplification of DNA by a restriction enzyme/DNA polymerase system", PNAS, 89, 1992, 392-396.
Walker, et al., "Multiplex strand displacement amplification (SDA) and detection of DNA sequences from *Mycobacterium tuberculosis* and other mycobacteria", Nucleic Acids Research 22, 1994, 2670-2677.
Walker, et al., "Strand displacement amplification—an isothermal, in vitro DNA amplification technique", NAR, 20, 1992, 1691-1696.
Walter, et al., "Strand displacement amplification as an in vitro model for rolling-circle replication: deletion formation and evolution during serial transfer", PNAS 91, 1994, 7937-7941.
Westin, et al., "Anchored multiplex amplification on a microelectric chip array", Nature Biotechnology 18, 2000, 199-204.
Winn-Deen, et al., "Non-radioactive detection of *Mycobacterium tuberculosis* LCR products in a microtiter plate format", Mol. Cell. Probes 7:179-186, 1993.
Wolf, et al., "Rapid hybridization kinetics of DNA attached to submicron latex particles", NAR, 15, 1987, 2911-2926.
Yang, et al., "Covalent Immobilization of oligonucleotides on modified glass/silicon surfaces for solid-phase DNA hybridization and amplification", Chemistry Letters, 1998, 257-8.
Yershov, et al., "DNA analysis and diagnostics on oligonucleotide microchips", PNAS US 93, 1996, 4913-4918.

* cited by examiner

Cluster Sequencing Data

- Mixed two libraries and sequenced by SBS in one channel
- Data from a single tile

| Reference Sequences | % of Clusters Aligning to Reference |
|---|---|
| PhiX | 68 |
| BAC | 29 |
| E.Coli | 3 |

| | PhiX TAG | BAC TAG | Other TAGs |
|---|---|---|---|
| PhiX | 98 % | 0.1 % | 2 % |
| BAC | 0.1 % | 98 % | 2 % |

- Majority of BAC and PhiX inserts were sequenced with the correct TAG

Fig. 4

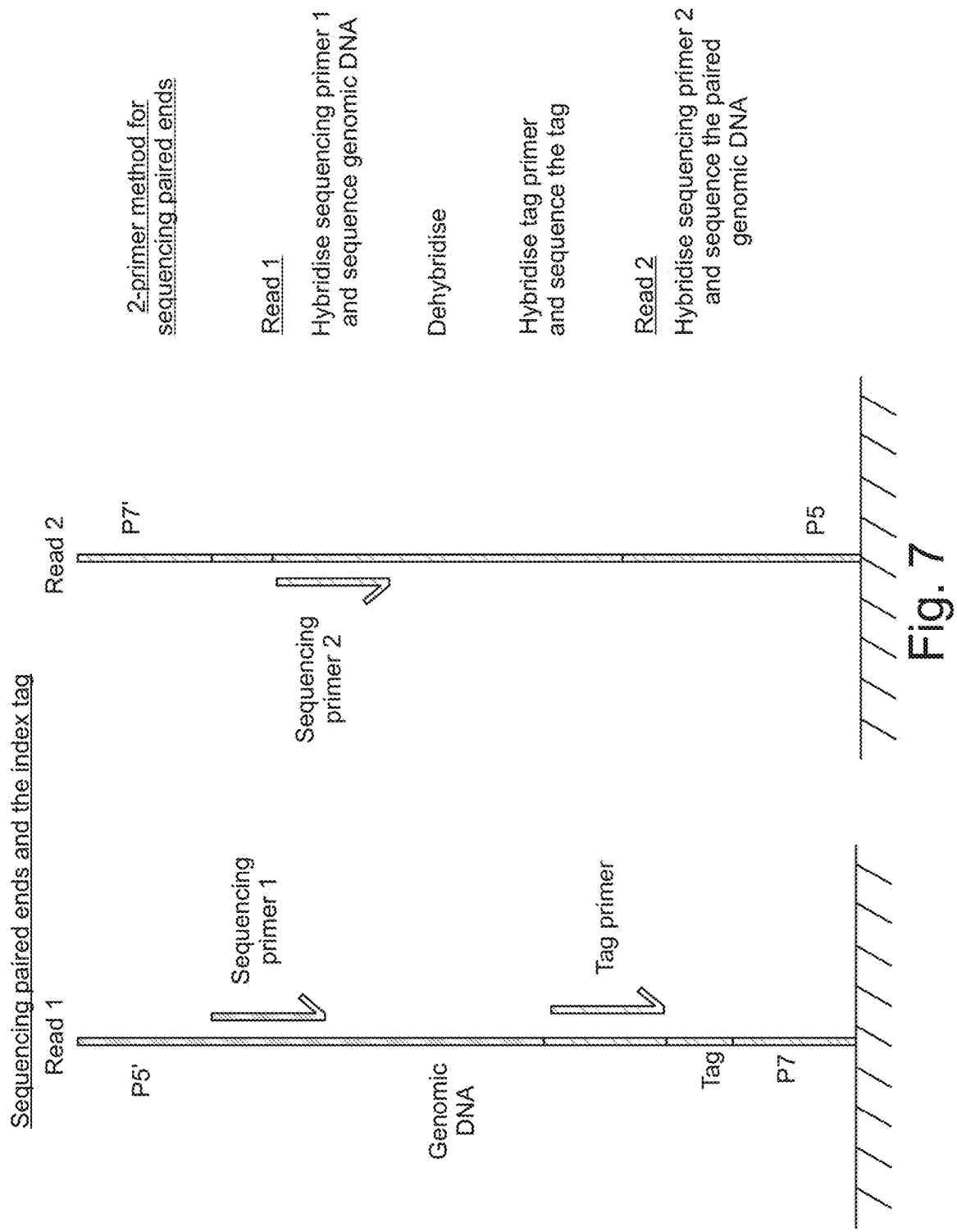

Experiment - 6BAC+6PhiX

Data analysis from 100 tiles, lane 1

*Not 100% due to E.coli contamination in both BAC and PhiX samples

| Tag | Genome | Clus No | BAC R1 | BAC R2 | PhiX R1 | PhiX R2 |
|---|---|---|---|---|---|---|
| ATCATCG | PhiX | 6522 | 0% | 0% | 96% | 92% |
| CGATGT | PhiX | 3548 | 0% | 0% | 96% | 92% |
| TTAGGC | PhiX | 10394 | 0% | 0% | 97% | 93% |
| TGACCA | PhiX | 6842 | 0% | 0% | 97% | 93% |
| ACAGTG | PhiX | 6677 | 0% | 0% | 97% | 93% |
| CAGATC | PhiX | 11231 | 0% | 0% | 96% | 93% |
| GCCAAT | BAC | 6174 | 97% | 92% | 0% | 0% |
| ACTTGA | BAC | 5375 | 97% | 93% | 0% | 0% |
| GATCAG | BAC | 5404 | 97% | 93% | 0% | 0% |
| TAGCTT | BAC | 10239 | 97% | 94% | 0% | 0% |
| GGCTAC | BAC | 9734 | 97% | 93% | 0% | 0% |
| CTTGTA | BAC | 9704 | 97% | 93% | 0% | 0% |

Can align missed calls

| Expected Tag | Observed Tag | Genome | Clus No | BAC R1 | BAC R2 | PhiX R1 | PhiX R2 |
|---|---|---|---|---|---|---|---|
| TGACCA | TGACAA | | 8 | 0% | 0% | 100% | 88% |
| TGACCA | TCCAAT | | 34 | 97% | 94% | 0% | 0% |
| TGACCA | TATCAG | | 28 | 100% | 96% | 0% | 0% |

Data suggest very low level of false positives, with the possibility of error checking

Fig. 8

Forked Adaptor Primers SBS3 / SBS12 (indexing/paired ends)
Adaptor oligo 2     5'  ACACTCTTTCCCTACACGACGCTCTTCCGATCT 3'  (SEQ ID NO. 1)
Adaptor oligo 1 (short)           5' P-GATCGGAAGAGCACACGTCT 3'  (SEQ ID NO. 3)

```
        5'ACACTCTTTCCCTACACGAC GCTCTTCCGATCT 3' (SEQ ID NO. 1)
                                3' TCTGTGCACA CGAGAAGGCTAG 5' (SEQ ID NO. 3)
```

PCR Primer
Universal LPX primer  5' GTGACTGGAGTTCAGACGTGTGCTCTTCCGATCxT 3' (SEQ ID NO. 7)
LPX primer            5' AATGATACGGCGACCACCGAGATCTACACTCTTTCCTACACGACGCTCTTCCGATCxT (SEQ ID NO. 8)
Tag1 primer (CGTGAT)  5' CAAGCAGAAGACGGCATACGAGATCGTGATGTGACTGGAGTTC 3'(SEQ ID NO. 9)
Tag2 primer (CGTGAT)  5' CAAGCAGAAGACGGCATACGAGATACATCGGTGACTGGAGTTC 3'(SEQ ID NO. 10)
Tag3 primer (GCCTAA)  5' CAAGCAGAAGACGGCATACGAGATGCCTAAGTGACTGGAGTTC 3'(SEQ ID NO. 11)
Tag4 primer (TGGTCA)  5' CAAGCAGAAGACGGCATACGAGATTGGTCAGTGACTGGAGTTC 3'(SEQ ID NO. 12)
Tag5 primer (CACTGT)  5' CAAGCAGAAGACGGCATACGAGATCACTGTGTGACTGGAGTTC 3'(SEQ ID NO. 13)
Tag6 primer (ATTGGC)  5' CAAGCAGAAGACGGCATACGAGATATTGGCGTGACTGGAGTTC 3'(SEQ ID NO. 14)
Tag7 primer (GATCTG)  5' CAAGCAGAAGACGGCATACGAGATGATCTGGTGACTGGAGTTC 3'(SEQ ID NO. 15)
Tag8 primer (TCAAGT)  5' CAAGCAGAAGACGGCATACGAGATTCAAGTGTGACTGGAGTTC 3'(SEQ ID NO. 16)
Tag9 primer (CTGATC)  5' CAAGCAGAAGACGGCATACGAGATCTGATCGTGACTGGAGTTC 3'(SEQ ID NO. 17)
Tag10 primer (AAGCTA) 5' CAAGCAGAAGACGGCATACGAGATAAGCTAGTGACTGGAGTTC 3'(SEQ ID NO. 18)
Tag11 primer (GTAGCC) 5' CAAGCAGAAGACGGCATACGAGATGTAGCCGTGACTGGAGTTC 3'(SEQ ID NO. 19)
Tag12 primer (TACAAG) 5' CAAGCAGAAGACGGCATACGAGATTACAAGGTGACTGGAGTTC 3'(SEQ ID NO. 20)

Sequencing primers
SBS12      5' GTGACTGGAGTTCAGACGTGTGCTCTTCCGATC 3'(SEQ ID NO. 63)
SBS12rev   5' GATCGGAAGAGCACACGTCTGAACTCCAGTCAC 3'(SEQ ID NO. 62)
SBS3       5' ACACTCTTTCCCTACACGACGCTCTTCCGATC 3'(SEQ ID NO. 61)

Fig. 9

SEQUENCE LISTING

```
<160> NUMBER OF SEQ ID NOS: 63

<210> SEQ ID NO 1
<211> LENGTH: 33
<212> TYPE: DNA
<213> ORGANISM: Artificial
<220> FEATURE:
<223> OTHER INFORMATION: Synthetic oligonucleotide
<220> FEATURE:
<221> NAME/KEY: misc_feature
<222> LOCATION: (32)..(33)
<223> OTHER INFORMATION: Nucleotides at positions 32 and 33 linked by a
      phosphorothioate bond

<400> SEQUENCE: 1
acactctttc cctacacgac gctcttccga tct                               33

<210> SEQ ID NO 2
<211> LENGTH: 32
<212> TYPE: DNA
<213> ORGANISM: Artificial
<220> FEATURE:
<223> OTHER INFORMATION: Synthetic Oligonucleotide

<400> SEQUENCE: 2
gatcggaaga gcggttcagc aggaatgccg ag                                32

<210> SEQ ID NO 3
<211> LENGTH: 20
<212> TYPE: DNA
<213> ORGANISM: Artificial
<220> FEATURE:
<223> OTHER INFORMATION: Synthetic Oligonucleotide

<400> SEQUENCE: 3
gatcggaaga gcacacgtct                                              20

<210> SEQ ID NO 4
<211> LENGTH: 58
<212> TYPE: DNA
<213> ORGANISM: Artificial
<220> FEATURE:
<223> OTHER INFORMATION: Synthetic Oligonucleotide
<220> FEATURE:
<221> NAME/KEY: misc_feature
<222> LOCATION: (57)..(58)
<223> OTHER INFORMATION: Nucleotides in positions 57 and 58 linked by a
      phosphorothioate bond

<400> SEQUENCE: 4
aatgatacgg cgaccaccga gatctacact ctttccctac acgacgctct tccgatct    58

<210> SEQ ID NO 5
```

<211> LENGTH: 61
<212> TYPE: DNA
<213> ORGANISM: Artificial
<220> FEATURE:
<223> OTHER INFORMATION: Synthetic Oligonucleotide
<220> FEATURE:
<221> NAME/KEY: misc_feature
<222> LOCATION: (60)..(61)
<223> OTHER INFORMATION: Nucleotides in positions 60 and 61 linked by a
      phosphorothioate bond

<400> SEQUENCE: 5
caagcagaag acggcatacg agatcggtct cggcattcct gctgaaccgc tcttccgatc    60
t                                                                    61

<210> SEQ ID NO 6
<211> LENGTH: 61
<212> TYPE: DNA
<213> ORGANISM: Artificial
<220> FEATURE:
<223> OTHER INFORMATION: Synthetic Oligonucleotide
<220> FEATURE:
<221> NAME/KEY: misc_feature
<222> LOCATION: (60)..(61)
<223> OTHER INFORMATION: Nucleotides in positions 60 and 61 linked by a
      phosphorothioate bond

<400> SEQUENCE: 6
caagcagaag acggcatacg atcgcggtct cggcattcct gctgaaccgc tcttccgatc    60
t                                                                    61

<210> SEQ ID NO 7
<211> LENGTH: 34
<212> TYPE: DNA
<213> ORGANISM: Artificial
<220> FEATURE:
<223> OTHER INFORMATION: Synthetic Oligonucleotide
<220> FEATURE:
<221> NAME/KEY: misc_feature
<222> LOCATION: (33)..(34)
<223> OTHER INFORMATION: Nucleotides at positions 33 and 34 linked by
      phosphorothioate

<400> SEQUENCE: 7
gtgactggag ttcagacgtg tgctcttccg atct                                34

<210> SEQ ID NO 8
<211> LENGTH: 58
<212> TYPE: DNA
<213> ORGANISM: Artificial
<220> FEATURE:
<223> OTHER INFORMATION: Synthetic Oligonucleotide
<220> FEATURE:
<221> NAME/KEY: misc_feature
<222> LOCATION: (57)..(58)
<223> OTHER INFORMATION: Nucleotides at positions 57 and 58 linked by
      phophorothioate bond

<400> SEQUENCE: 8
aatgatacgg cgaccaccga gatctacact ctttccctac acgacgctct tccgatct      58

<210> SEQ ID NO 9
<211> LENGTH: 43
<212> TYPE: DNA
<213> ORGANISM: Artificial
<220> FEATURE:
<223> OTHER INFORMATION: Synthetic Oligonucleotide

<400> SEQUENCE: 9
caagcagaag acggcatacg agatcgtgat gtgactggag ttc                    43

<210> SEQ ID NO 10
<211> LENGTH: 43
<212> TYPE: DNA
<213> ORGANISM: Artificial
<220> FEATURE:
<223> OTHER INFORMATION: Synthetic Oligonucleotide

<400> SEQUENCE: 10
caagcagaag acggcatacg agatacatcg gtgactggag ttc                    43

<210> SEQ ID NO 11
<211> LENGTH: 43
<212> TYPE: DNA
<213> ORGANISM: Artificial
<220> FEATURE:
<223> OTHER INFORMATION: Synthetic Oligonucleotide

<400> SEQUENCE: 11
caagcagaag acggcatacg agatgcctaa gtgactggag ttc                    43

<210> SEQ ID NO 12
<211> LENGTH: 43
<212> TYPE: DNA
<213> ORGANISM: Artificial
<220> FEATURE:
<223> OTHER INFORMATION: Synthetic Oligonucleotide

<400> SEQUENCE: 12
caagcagaag acggcatacg agattggtca gtgactggag ttc                    43

<210> SEQ ID NO 13
<211> LENGTH: 43
<212> TYPE: DNA
<213> ORGANISM: Artificial
<220> FEATURE:
<223> OTHER INFORMATION: Synthetic Oligonucleotide

<400> SEQUENCE: 13
caagcagaag acggcatacg agatcactgt gtgactggag ttc                    43

<210> SEQ ID NO 14
<211> LENGTH: 43
<212> TYPE: DNA
<213> ORGANISM: Artificial
<220> FEATURE:
<223> OTHER INFORMATION: Synthetic Oligonucleotide

<400> SEQUENCE: 14
caagcagaag acggcatacg agatattggc gtgactggag ttc                    43

<210> SEQ ID NO 15
<211> LENGTH: 43
<212> TYPE: DNA
<213> ORGANISM: Artificial
<220> FEATURE:
<223> OTHER INFORMATION: Synthetic Oligonucleotide

<400> SEQUENCE: 15
caagcagaag acggcatacg agatgatctg gtgactggag ttc                    43

<210> SEQ ID NO 16
<211> LENGTH: 43
<212> TYPE: DNA

<213> ORGANISM: Artificial
<220> FEATURE:
<223> OTHER INFORMATION: Synthetic Oligonucleotide

<400> SEQUENCE: 16
caagcagaag acggcatacg agattcaagt gtgactggag ttc        43

<210> SEQ ID NO 17
<211> LENGTH: 43
<212> TYPE: DNA
<213> ORGANISM: Artificial
<220> FEATURE:
<223> OTHER INFORMATION: Synthetic Oligonucleotide

<400> SEQUENCE: 17
caagcagaag acggcatacg agatctgatc gtgactggag ttc        43

<210> SEQ ID NO 18
<211> LENGTH: 43
<212> TYPE: DNA
<213> ORGANISM: Artificial
<220> FEATURE:
<223> OTHER INFORMATION: Synthetic Oligonucleotide

<400> SEQUENCE: 18
caagcagaag acggcatacg agataagcta gtgactggag ttc        43

<210> SEQ ID NO 19
<211> LENGTH: 43
<212> TYPE: DNA
<213> ORGANISM: Artificial
<220> FEATURE:
<223> OTHER INFORMATION: Synthetic Oligonucleotide

<400> SEQUENCE: 19
caagcagaag acggcatacg agatgtagcc gtgactggag ttc        43

<210> SEQ ID NO 20
<211> LENGTH: 43
<212> TYPE: DNA
<213> ORGANISM: Artificial
<220> FEATURE:
<223> OTHER INFORMATION: Synthetic Oligonucleotide

<400> SEQUENCE: 20
caagcagaag acggcatacg agattacaag gtgactggag ttc        43

<210> SEQ ID NO 21
<211> LENGTH: 204
<212> TYPE: DNA
<213> ORGANISM: Artificial
<220> FEATURE:
<223> OTHER INFORMATION: Synthetic Oligonucleotide

<400> SEQUENCE: 21
aatgatacgg cgaccaccga gatctacact ctttccctac acgacgctct tccgatctac        60
tgatttcatt gcagccaaag gcaaactttg gctgcatcgt tttacagtcg ccataagcct       120
ttcctctgtt aaaccgcctt ctgagatcgg aagagcggtt cagcaggaat gccgagaccg       180
atctcgtatg ccgtcttctg cttg                                              204

<210> SEQ ID NO 22
<211> LENGTH: 214
<212> TYPE: DNA
<213> ORGANISM: Artificial

<220> FEATURE:
<223> OTHER INFORMATION: Synthetic Oligonucleotide

<400> SEQUENCE: 22
aatgatacgg cgaccaccga gatctacact ctttccctac acgacgctct tccgatctat   60
caatattgtg aaaatgacca tactgccaaa aaaaaactac aaattcaatg caattttcat  120
caaaatacca tcatcattct tcacaatatt gatagatcgg aagagcggtt cagcaggaat  180
gccgagaccg atctcgtatg ccgtcttctg cttg                              214

<210> SEQ ID NO 23
<211> LENGTH: 215
<212> TYPE: DNA
<213> ORGANISM: Artificial
<220> FEATURE:
<223> OTHER INFORMATION: Synthetic Oligonucleotide

<400> SEQUENCE: 23
aatgatacgg cgaccaccga gatctacact ctttccctac acgacgctct tccgatctct   60
cactcctggc agagggacgt gtgactagcc atgggcccct aggtctccag ttcctgggta  120
gcttgtattt ttgaacatct cctgtatatt agttagatcg gaagagcggt tcagcaggaa  180
tgccgagacc gatctcgtat gccgtcttct gcttg                             215

<210> SEQ ID NO 24
<211> LENGTH: 147
<212> TYPE: DNA
<213> ORGANISM: Artificial
<220> FEATURE:
<223> OTHER INFORMATION: Synthetic Oligonucleotide

<400> SEQUENCE: 24
aatgatacgg cgaccaccga gatctacact ctttccctac acgacgctct tccgatctag   60
tgtagttgag atctgcctta gcagcaagat cggaagagcg gttcagcagg aatgccgaga  120
ccgatctcgt atgccgtctt ctgcttg                                      147

<210> SEQ ID NO 25
<211> LENGTH: 183
<212> TYPE: DNA
<213> ORGANISM: Artificial
<220> FEATURE:
<223> OTHER INFORMATION: Synthetic Oligonucleotide

<400> SEQUENCE: 25
aatgatacgg cgaccaccga gatctacact ctttccctac acgacgctct tccgatctaa   60
cacatttcaa agtttggggc cctcctcctc cccaaaaaac aaaccacaaa aaacaaacaa  120
aaagatcgga gagcggttc agcaggaatg ccgagaccga tctcgtatgc cgtcttctgc  180
ttg                                                                183

<210> SEQ ID NO 26
<211> LENGTH: 170
<212> TYPE: DNA
<213> ORGANISM: Artificial
<220> FEATURE:
<223> OTHER INFORMATION: Synthetic Oligonucleotide

<400> SEQUENCE: 26
ggcgaccacc gagatctaca ctctttccct acacgacgct cttccgatct gaatgccttt   60
tatagcattt aatttttcct aagtataatt accaaataaa aattgtataa gatcggaaga  120
gcggttcagc aggaatgccg agaccgatct cgtatgccgt cttctgcttg        170

<210> SEQ ID NO 27
<211> LENGTH: 180
<212> TYPE: DNA
<213> ORGANISM: Artificial
<220> FEATURE:
<223> OTHER INFORMATION: Synthetic Oligonucleotide

<400> SEQUENCE: 27
aatgatacgg cgaccaccga gatctacact ctttccctac acgacgctct tccgatcttg        60
ggcccgggag gagtttgccg gggaggagtg ggtttggaat cggggttaaa ggaaagagaa        120
gatcggaaga gcggttcagc aggaatgccg agaccgatct cgtatgccgt cttctgcttg        180

<210> SEQ ID NO 28
<211> LENGTH: 190
<212> TYPE: DNA
<213> ORGANISM: Artificial
<220> FEATURE:
<223> OTHER INFORMATION: Synthetic Oligonucleotide

<400> SEQUENCE: 28
tgatacggcg accaccgaga tctacactct ttccctacac gacgctcttc cgatctaaga        60
tctatttcaa atggactgta gatctaagta taaaaggtaa gagaataatt attctagaaa        120
gtaaatgtaa gatcggaaga gcggttcagc aggaatgccg agaccgatct cgtatgccgt        180
cttctgcttg        190

<210> SEQ ID NO 29
<211> LENGTH: 192
<212> TYPE: DNA
<213> ORGANISM: Artificial
<220> FEATURE:
<223> OTHER INFORMATION: Synthetic Oligonucleotide

<400> SEQUENCE: 29
aatgatacgg cgaccaccag atctacactc tttccctaca cgacgctctt ccgatctggg        60
aggccaaggt gggtggatca cctgagatca ggagttcgag accagctggc caacatgatg        120
aaactctgtc tagatcggaa gagcggttca gcaggaatgc cgagaccgat ctcgtatgcc        180
gtcttctgct tg        192

<210> SEQ ID NO 30
<211> LENGTH: 185
<212> TYPE: DNA
<213> ORGANISM: Artificial
<220> FEATURE:
<223> OTHER INFORMATION: Synthetic Oligonucleotide

<400> SEQUENCE: 30
aatgatacgg cgaccaccga gatctacact ctttccctac acgacgctct tccgatcttg        60
accattgtaa ccattaatgt agactgcaat gatatgcact atttacaacc ttttttaaga        120
ctctagatcg gaagagcggt tcagcaggaa tgccgagacc gatctcgtat gccgtcttct        180
gcttg        185

<210> SEQ ID NO 31
<211> LENGTH: 199
<212> TYPE: DNA
<213> ORGANISM: Artificial
<220> FEATURE:
<223> OTHER INFORMATION: Synthetic Oligonucleotide

<400> SEQUENCE: 31

```
aatgatacgg cgaccaccga gatctacact ctttccctac acgacgctct tccgatctct    60
ttgaagagct ggcagtagaa gataaacagg ctggggaaga agagaaagtg ctcaaggaga   120
aggagcagca gcagcagcag atcggaagag cggttcagca ggaatgccga gaccgatctc   180
gtatgccgtc ttctgcttg                                                199
```

<210> SEQ ID NO 32
<211> LENGTH: 212
<212> TYPE: DNA
<213> ORGANISM: Artificial
<220> FEATURE:
<223> OTHER INFORMATION: Synthetic Oligonucleotide

<400> SEQUENCE: 32

```
aatgatacgg cgaccaccga gatctacact ctttccctac acgacgctct tccgatctag    60
tattcaacaa gtctgtcttt tccaagtgtc tttaaagacc agaaatacct gttttttaaca  120
cacagggttg caaaattcag aggagattgg cagatcggaa gagcggttca gcaggaatgc   180
cgagaccgat ctcgtatgcc gtcttctgct tg                                 212
```

<210> SEQ ID NO 33
<211> LENGTH: 247
<212> TYPE: DNA
<213> ORGANISM: Artificial
<220> FEATURE:
<223> OTHER INFORMATION: Synthetic Oligonucleotide

<400> SEQUENCE: 33

```
aatgatacgg cgaccaccga gatctacact ctttccctac acgacgctct tccgatctct    60
tgagatgagt gatgacggcg cgctggaagt tgctcgtcgc gctcgcggta cgccgcgcat   120
tgccaaccgt ctgctgcgtc gagtgcgtga tttcgccgaa gtgaagcacg atggcaccat   180
ctcaagagat cggaagagcg gttcagcagg aatgccgaga ccgatctcgt atgccgtctt   240
ctgcttg                                                             247
```

<210> SEQ ID NO 34
<211> LENGTH: 202
<212> TYPE: DNA
<213> ORGANISM: Artificial
<220> FEATURE:
<223> OTHER INFORMATION: Synthetic Oligonucleotide

<400> SEQUENCE: 34

```
aatgatacgg cgaccaccga gatctacact ctttccctac acgacgctct tccgatctgg    60
ggttggtgga acccagatgc ctcccaggat tggtgggccc tgtggcactt gtacctgctg   120
ttgctgttgc tgctgctgct gagatcggaa gagcggttca gcaggaatgc cgagaccgat   180
ctcgtatgcc gtcttctgct tg                                            202
```

<210> SEQ ID NO 35
<211> LENGTH: 166
<212> TYPE: DNA
<213> ORGANISM: Artificial
<220> FEATURE:
<223> OTHER INFORMATION: Synthetic Oligonucleotide

<400> SEQUENCE: 35

```
aatgatacgg cgaccaccga gatctacact ctttccctac acgacgctct tccgatctat    60
```
gataaggagc aggtttacag atcataagtg caaaagcggg cgagaagatc ggaagagcgg    120
ttcagcagga atgccgagac cgatctcgta tgccgtcttc tgcttg    166

<210> SEQ ID NO 36
<211> LENGTH: 147
<212> TYPE: DNA
<213> ORGANISM: Artificial
<220> FEATURE:
<223> OTHER INFORMATION: Synthetic Oligonucleotide

<400> SEQUENCE: 36
gatacggcga ccaccgagat ctacactctt tccctacacg acgctcttcc gatctctgat    60
actgttgtaa ccacccaatt ggttcaagat cggaagagcg gttcagcagg aatgccgaga    120
ccgatctcgt atgccgtctt ctgcttg    147

<210> SEQ ID NO 37
<211> LENGTH: 183
<212> TYPE: DNA
<213> ORGANISM: Artificial
<220> FEATURE:
<223> OTHER INFORMATION: Synthetic Oligonucleotide

<400> SEQUENCE: 37
aatgatacga ccaccgagat ctacactctt tccctacacg acgctcttcc gatcttaaag    60
ctaccagtta tatggctgtt ggtttctatg tggctaaata cgttaacaaa agtcagata    120 tgagatcgga agagcggttc agcaggaatg ccgagaccgc gatcgtatgc cgtcttctgc    180
ttg    183

<210> SEQ ID NO 38
<211> LENGTH: 174
<212> TYPE: DNA
<213> ORGANISM: Artificial
<220> FEATURE:
<223> OTHER INFORMATION: Synthetic Oligonucleotide

<400> SEQUENCE: 38
gatacggcga ccaccgagat ctacactctt tccctacacg acgctcttcc gatctcgacc    60
actcgcgatt caatcatgac ttcgtgataa aagattgagt gtgaggttat aacagatcgg    120
aagagcggtt cagcaggaat gccgagaccg cgatcgtatg ccgtcttctg cttg    174

<210> SEQ ID NO 39
<211> LENGTH: 179
<212> TYPE: DNA
<213> ORGANISM: Artificial
<220> FEATURE:
<223> OTHER INFORMATION: Synthetic Oligonucleotide

<400> SEQUENCE: 39
tgatacggcg accaccgaga tctacactct ttccctacac gacgctcttc cgatcttcta    60
tgaaggatgt tttccgttct ggtgattcgt ctaagaagtt taagattgct gagggtcaag    120
atcggaagag cggttcagca ggaatgccga gaccgcgatc gtatgccgtc ttctgcttg    179

<210> SEQ ID NO 40
<211> LENGTH: 169
<212> TYPE: DNA
<213> ORGANISM: Artificial
<220> FEATURE:
<223> OTHER INFORMATION: Synthetic Oligonucleotide

<400> SEQUENCE: 40

```
aatgatacgg cgaccaccga gatctacact ctttccctac acgacgctct tccgatctgg    60
ttgcgccgcc aaaacgtcgg ctacagtaac ttttcccagc ctcaatctag atcggaagag   120
cggttcagca ggaatgccga gaccgcgatc gtatgccgtc ttctgcttg               169

<210> SEQ ID NO 41
<211> LENGTH: 166
<212> TYPE: DNA
<213> ORGANISM: Artificial
<220> FEATURE:
<223> OTHER INFORMATION: Synthetic Oligonucleotide

<400> SEQUENCE: 41
tgatacggcg accaccgaga tctacatctt tccctacacg acgctcttcc gatctaacaa    60
ctgaacggac tggaaacact ggtcataatc atggtggcga ataagagatc ggaagagcgg   120
ttcagcagga atgccgagac cgcgatcgta tgccgtcttc tgcttg                  166

<210> SEQ ID NO 42
<211> LENGTH: 164
<212> TYPE: DNA
<213> ORGANISM: Artificial
<220> FEATURE:
<223> OTHER INFORMATION: Synthetic Oligonucleotide

<400> SEQUENCE: 42
aatgatacgg cgaccaccga gatctacact ctttccctac acgacgctct tccgatctaa    60
atacgttaac aaaaagtcag atatggacct tgctgctaaa ggtagatcgg aagagcggtt   120
cagcaggaat gccgagaccg cgatcgtatg ccgtcttctg cttg                    164

<210> SEQ ID NO 43
<211> LENGTH: 194
<212> TYPE: DNA
<213> ORGANISM: Artificial
<220> FEATURE:
<223> OTHER INFORMATION: Synthetic Oligonucleotide

<400> SEQUENCE: 43
aatgatacgg cgaccaccga gatctacact ctttccctac acgacgctct tccgatctgt    60
caatataacc agtagtgtta acagtcggga gaggagtggc attaacacca tccttcatga   120
acttaatcca ctgagatcgg aagagcggtt cagcaggaat gccgagaccg cgatcgtatg   180
ccgtcttctg cttg                                                     194

<210> SEQ ID NO 44
<211> LENGTH: 198
<212> TYPE: DNA
<213> ORGANISM: Artificial
<220> FEATURE:
<223> OTHER INFORMATION: Synthetic Oligonucleotide

<400> SEQUENCE: 44
aatgatacgg cgaccaccga gatctacact ctttccctac acgacgctct tccgatctga    60
tagtttgacg gttaatgctg gtaatggtgg ttttcttcat tgcattcaga tggatacatc   120
tgtcaacgcc gctaatcaga tcggaagagc ggttcagcag gaatgccgag accgcgatcg   180
tatgccgtct tctgcttg                                                 198

<210> SEQ ID NO 45
<211> LENGTH: 179
<212> TYPE: DNA
```

```
<213> ORGANISM: Artificial
<220> FEATURE:
<223> OTHER INFORMATION: Synthetic Oligonucleotide

<400> SEQUENCE: 45
aatgatacgg cgaccaccga gatctacact ctttccctac acgacgctct tccgatcttg    60
aaaccaacat aaacattatt gcccggcgta cgaggaagga cgtcaatagt cacacagtag   120
atcggaagag cggttcagca ggaatgccga gaccgcgatc gtatgccgtc ttctgcttg    179

<210> SEQ ID NO 46
<211> LENGTH: 198
<212> TYPE: DNA
<213> ORGANISM: Artificial
<220> FEATURE:
<223> OTHER INFORMATION: Synthetic Oligonucleotide

<400> SEQUENCE: 46
aatgatacgg cgaccaccga gatctacact ctttccctac acgacgctct tccgatctcc    60
agcttcttcg gcacctgttt tacagacacc taaagctaca tcgtcaacgt tatattttga   120
tagtttgacg gttaataaga tcggaagagc ggttcagcag gaatgccgag accgcgatcg   180
tatgccgtct tctgcttg                                                 198

<210> SEQ ID NO 47
<211> LENGTH: 151
<212> TYPE: DNA
<213> ORGANISM: Artificial
<220> FEATURE:
<223> OTHER INFORMATION: Synthetic Oligonucleotide

<400> SEQUENCE: 47
aatgatacgg cgaccaccga gatctacact ctttccctac acgacgctct tccgatctca    60
gttttgccgc aagctggctg ctgaacgccc agatcggaag agcggttcag caggaatgcc   120
gagaccgcga tcgtatgccg tcttctgctt g                                  151

<210> SEQ ID NO 48
<211> LENGTH: 173
<212> TYPE: DNA
<213> ORGANISM: Artificial
<220> FEATURE:
<223> OTHER INFORMATION: Synthetic Oligonucleotide

<400> SEQUENCE: 48
aatgatacgg cgaccaccga gatctacact ctttccctac acgacgctct tccgatcttt    60
tgctgatgaa ctaagtcaac ctcagcacta accttgcgag tcatttcttt gaagatcgga   120
agagcggttc agcaggaatg ccgagaccgc gatcgtatgc cgtcttctgc ttg          173

<210> SEQ ID NO 49
<211> LENGTH: 151
<212> TYPE: DNA
<213> ORGANISM: Artificial
<220> FEATURE:
<223> OTHER INFORMATION: Synthetic Oligonucleotide

<400> SEQUENCE: 49
aatgatacgg cgaccaccga gatctacact ctttccctac acgacgctct tccgatctaa    60
tagacgcaac gcgagcagta gactccttct agatcggaag agcggttcag caggaatgcc   120
gagaccgcga tcgtatgccg tcttctgctt g                                  151
```

```
<210> SEQ ID NO 50
<211> LENGTH: 168
<212> TYPE: DNA
<213> ORGANISM: Artificial
<220> FEATURE:
<223> OTHER INFORMATION: Synthetic Oligonucleotide

<400> SEQUENCE: 50
aatgatacgg cgaccaccga gatctacact ctttccctac acgacgctct tccgatctgg      60
aggcctccag caatcttgaa cactcatcct taatacctttt cttttgaga tcggaagagc     120 ggttcagcag gaatgccgag accgcgatcg tatgccgtct tctgcttg                  168

<210> SEQ ID NO 51
<211> LENGTH: 181
<212> TYPE: DNA
<213> ORGANISM: Artificial
<220> FEATURE:
<223> OTHER INFORMATION: Synthetic Oligonucleotide

<400> SEQUENCE: 51
aatgatacgg cgaccaccga gatctacact ctttccctac acgacgctct tccgatctac      60
tcctaagcag aaaacctacc gcgcttcgct tggtcaaccc ctcagcggca aaaattaaaa     120
agatcggaag agcggttcag caggaatgcc gagaccgcga tcgtatgccg tcttctgctt    180
g                                                                    181

<210> SEQ ID NO 52
<211> LENGTH: 182
<212> TYPE: DNA
<213> ORGANISM: Artificial
<220> FEATURE:
<223> OTHER INFORMATION: Synthetic Oligonucleotide

<400> SEQUENCE: 52
aatgatacgg cgaccaccga gatctacact ctttccctac acgacgctct tccgatctga      60
gccgacatcg aggtgccaaa caccgccgtc gatatgaact cttgggcggt atcagcctgt    120
tagatcggaa gagcggttca gcaggaatgc cgagaccgcg atcgtatgcc gtcttctgct    180
tg                                                                   182

<210> SEQ ID NO 53
<211> LENGTH: 58
<212> TYPE: DNA
<213> ORGANISM: Artificial
<220> FEATURE:
<223> OTHER INFORMATION: Synthetic Oligonucleotide

<400> SEQUENCE: 53
aatgatacgg cgaccaccga gatctacact ctttccctac acgacgctct tccgatct        58

<210> SEQ ID NO 54
<211> LENGTH: 61
<212> TYPE: DNA
<213> ORGANISM: Artificial
<220> FEATURE:
<223> OTHER INFORMATION: Synthetic Oligonucleotide
<220> FEATURE:
<221> NAME/KEY: misc_feature
<222> LOCATION: (38)..(40)
<223> OTHER INFORMATION: n is a, c, g, or t

<400> SEQUENCE: 54
agatcggaag agcggttcag caggaatgcc gagaccgnnn tcgtatgccg tcttctgctt      60
``` g                                                                61

<210> SEQ ID NO 55
<211> LENGTH: 30
<212> TYPE: DNA
<213> ORGANISM: Artificial
<220> FEATURE:
<223> OTHER INFORMATION: Synthetic Oligonucleotide
<220> FEATURE:
<221> NAME/KEY: misc_feature
<222> LOCATION: (10)..(11)
<223> OTHER INFORMATION: Nucleotides at positions 10 and 11 linked by
      diol

<400> SEQUENCE: 55
tttttttttt aatgatacgg cgaccaccga                                  30

<210> SEQ ID NO 56
<211> LENGTH: 31
<212> TYPE: DNA
<213> ORGANISM: Artificial
<220> FEATURE:
<223> OTHER INFORMATION: Synthetic Oligonucleotide

<400> SEQUENCE: 56
tttttttttt caagcagaag acggcatacg a                                31

<210> SEQ ID NO 57
<211> LENGTH: 32
<212> TYPE: DNA
<213> ORGANISM: Artificial
<220> FEATURE:
<223> OTHER INFORMATION: Synthetic Oligonucleotide

<400> SEQUENCE: 57
acactctttc cctacacgac gctcttccga tc                               32

<210> SEQ ID NO 58
<211> LENGTH: 37
<212> TYPE: DNA
<213> ORGANISM: Artificial
<220> FEATURE:
<223> OTHER INFORMATION: Synthetic Oligonucleotide

<400> SEQUENCE: 58
agatcggaag agcggttcag caggaatgcc gagaccg                          37

<210> SEQ ID NO 59
<211> LENGTH: 39
<212> TYPE: DNA
<213> ORGANISM: Artificial
<220> FEATURE:
<223> OTHER INFORMATION: Synthetic Oligonucleotide
<220> FEATURE:
<221> NAME/KEY: misc_feature
<222> LOCATION: (33)..(33)
<223> OTHER INFORMATION: Nucleotide at position 33 is 2-deoxyuridine

<400> SEQUENCE: 59
tttttttttt aatgatacgg cgaccaccga ganctacac                        39

<210> SEQ ID NO 60
<211> LENGTH: 31
<212> TYPE: DNA
<213> ORGANISM: Artificial
<220> FEATURE:
<223> OTHER INFORMATION: Synthetic Oligonucleotide
<220> FEATURE:

```
<221> NAME/KEY: misc_feature
<222> LOCATION: (30)..(30)
<223> OTHER INFORMATION: Nucleotide at position 30 is 8-oxoguanine

<400> SEQUENCE: 60 ttttttttttt caagcagaag acggcatacn a                                    31

<210> SEQ ID NO 61
<211> LENGTH: 32
<212> TYPE: DNA
<213> ORGANISM: Artificial
<220> FEATURE:
<223> OTHER INFORMATION: Synthetic Oligonucleotide

<400> SEQUENCE: 61
acactctttc cctacacgac gctcttccga tc                                    32

<210> SEQ ID NO 62
<211> LENGTH: 33
<212> TYPE: DNA
<213> ORGANISM: Artificial
<220> FEATURE:
<223> OTHER INFORMATION: Synthetic Oligonucleotide

<400> SEQUENCE: 62
gatcggaaga gcacacgtct gaactccagt cac                                   33

<210> SEQ ID NO 63
<211> LENGTH: 33
<212> TYPE: DNA
<213> ORGANISM: Artificial
<220> FEATURE:
<223> OTHER INFORMATION: Synthetic Oligonucleotide

<400> SEQUENCE: 63
gtgactggag ttcagacgtg tgctcttccg atc                                   33
```

METHODS FOR INDEXING SAMPLES AND SEQUENCING MULTIPLE POLYNUCLEOTIDE TEMPLATES

CROSS REFERENCE TO RELATED APPLICATIONS

The present application is a division of U.S. Ser. No. 14/307,254, filed Jun. 17, 2014, now U.S. Pat. No. 9,512,478, which is a continuation of U.S. Ser. No. 13/444,136, filed Apr. 11, 2012, now U.S. Pat. No. 8,822,150, which is a continuation U.S. Ser. No. 13/212,923, filed Aug. 18, 2011, now U.S. Pat. No. 8,182,989, which is a continuation of U.S. Ser. No. 12/012,613, filed Feb. 4, 2008, now U.S. Pat. No. 8,053,192, which claims priority from U.S. Provisional Application 60/899,221, filed Feb. 2, 2007. Applicants claim the benefits of priority under 35 U.S.C. § 119 as to the Provisional Application. The entire disclosures of these applications are incorporated herein by reference in their entireties.

FIELD OF THE INVENTION

The invention relates to methods for indexing samples during the sequencing of polynucleotide templates, resulting in the attachment of tags specific to the source of each nucleic acid sample such that after a sequencing run, both the source and sequence of each polynucleotide can be determined. Thus, the present invention pertains to analysis of complex genomes (e.g., human genomes), as well as multiplexing less complex genomes, such as those of bacteria, viruses, mitochondria, and the like.

BACKGROUND TO THE INVENTION

Several publications and patent documents are referenced in this application in order to more fully describe the state of the art to which this invention pertains. The disclosure of each of these publications and documents is incorporated by reference herein.

Advances in the study of biological molecules have been led, in part, by improvement in technologies used to characterise the molecules or their biological reactions. In particular, the study of the nucleic acids DNA and RNA has benefited from developing technologies used for sequence analysis.

The study of complex genomes, in particular, the search for the genetic basis of disease in humans requires genotyping on a massive scale. Screens for numerous genetic markers performed on populations large enough to yield statistically significant data are needed before associations can be made between a given genotype and a particular disease. However large-scale genotyping is demanding in terms of the cost of both materials and labour involved, and the time taken to perform the study, especially if the methodology employed involves separate serial analysis of individual DNA samples. One shortcut is to pool DNA from many individuals and to determine parameters such as the ratio of changes at certain positions in the genome. Such measurements of 'allele frequency' in the pool of samples can be used to correlate the relationship between the changes in the genome sequence and the occurrence of a disease. Hence, an association study involving 1000 patients would in theory only necessitate a 'one-pot' reaction for each genetic change. Pooling therefore represents an effective technique for analysing large quantities of samples in a facile manner.

One disadvantage of pooling samples prior to analysis is that information pertaining to individual DNA samples is lost; only global information such as allele frequencies is gathered, as there is no easy method for discerning which individuals gave rise to a particular genotype. An ability to genotype large populations in a small number of reactions, while retaining the information relating to the source of the individual samples, would yield the information content of a full non-pooled population screen in the time and at the cost of a pooled reaction.

Several of the new methods employed for high throughput DNA sequencing (*Nature.* 437, 376-380 (2005); *Science.* 309, 5741, 1728-1732 (2005)) rely on a universal amplification reaction, whereby a DNA sample is randomly fragmented, then treated such that the ends of the different fragments all contain the same DNA sequence. Fragments with universal ends can be amplified in a single reaction with a single pair of amplification primers. Separation of the library of fragments to the single molecule level prior to amplification ensures that the amplified molecules form discrete populations that can then be further analysed. Such separations can be performed either in emulsions (*Nature.* 437, 376-380 (2005); *Science.* 309, 5741, 1728-1732 (2005)), or on a surface (Nucleic Acids Research 27, e34 (1999); Nucleic Acids Research 15, e87 (2000)).

WO 98/44151 and WO 00/18957 both describe methods of forming polynucleotide arrays based on 'solid-phase' nucleic acid amplification, which is a bridging amplification reaction wherein the amplification products are immobilised on a solid support in order to form arrays comprised of nucleic acid clusters or 'colonies'. Each cluster or colony on such an array is formed from a plurality of identical immobilised polynucleotide strands and a plurality of identical immobilised complementary polynucleotide strands. The arrays so-formed are generally referred to herein as 'clustered arrays' and their general features will be further understood by reference to WO 98/44151 or WO 00/18957, the contents of both documents being incorporated herein in their entirety by reference.

In common with all amplification techniques, solid-phase bridging amplification requires the use of forward and reverse amplification primers which include 'template-specific' nucleotide sequences which are capable of annealing to sequences in the template to be amplified, or the complement thereof, under the conditions of the annealing steps of the amplification reaction. The sequences in the template to which the primers anneal under conditions of the amplification reaction may be referred to herein as 'primer-binding' sequences.

Certain embodiments of the methods described in WO 98/44151 and WO 00/18957 make use of 'universal' primers to amplify templates comprising a variable template portion that it is desired to amplify flanked 5' and 3' by common or 'universal' primer binding sequences. The 'universal' forward and reverse primers include sequences capable of annealing to the 'universal' primer binding sequences in the template construct. The variable template portion, or 'target' may itself be of known, unknown or partially known sequence. This approach has the advantage that it is not necessary to design a specific pair of primers for each target sequence to be amplified; the same primers can be used for amplification of different templates provided that each template is modified by addition of the same universal primer-binding sequences to its 5' and 3' ends. The variable target sequence can therefore be any DNA fragment of interest. An analogous approach can be used to amplify a mixture of templates (targets with known ends), such as a plurality or library of target nucleic acid molecules (e.g. genomic DNA fragments), using a single pair of universal forward and reverse primers, provided that each template molecule in the mixture is modified by the addition of the same universal primer-binding sequences.

DNA from more than one source can be sequenced on an array if each DNA sample is first tagged to enable its identification after it has been sequenced. Many low scale DNA-tag methodologies already exist, for example fluorescent labelling (Haughland, Handbook of Fluorescent Probes and Research Products, Invitrogen/Molecular Probes), but these are limited in scope to less than 10 or so reactions in parallel. DNA tags can be added to the ends of DNA fragments by cloning, of example as described in U.S. Pat. No. 5,604,097. The tags consist of eight four base 'words', where each word uses only three bases (A, T and C) in various combinations resulting in a total of 16,777,216 different tags that all have the same base pair composition and melting points. Such tags are used to label target molecules in a sample so that after an amplification reaction, each original molecule in the sample has a unique tag. The tags can then be used to 'sort' the sample onto beads containing sequences complementary to the tags such that each bead contains multiple copies of a single amplified target sequence (Brenner et al., (2000) Nature Biotechnology, 18, 630). In this application the tags are not sequenced, so the method does not provide a method of analysing targets from multiple samples, but rather a method of sorting a mixture of amplified templates from a single sample. The problem with enabling the method for individual samples rather than individual molecules is that the tags are synthesised in a combinatorial manner, meaning that all 16,777,216 different sequences are obtained in a single mixture in the same tube. Whilst this is ideal for treating one sample such that each individual molecule in the sample carries a different tag, it does not permit attachment of the same tag to every molecule in the sample.

DNA samples from multiple sources can, however, be tagged with different nucleic acid tags such that the source of the sample can be identified. Previous application WO05068656 describes the generic concept of indexing samples. In order to utilise this invention on arrays of amplified single molecule templates, for example as described in WO9844151, WO06099579 or WO04069849, it is advantageous to prepare the nucleic acids using the novel method described herein. The optimised DNA sample preparation techniques described herein are applicable to any method where the samples are amplified prior to sequencing. The DNA sample preparation techniques presented herein describe in detail the optimal placements of the sequencing primers and indexed tags within the DNA constructs to be sequenced.

SUMMARY OF THE INVENTION

The present inventors have developed methods for indexing samples, wherein the samples are amplified from isolated single template molecules. Using the techniques of the invention, it is possible to prepare a nucleic acid sample for a sequencing reaction wherein both the target sequence and the tag sequence can be determined.

In a first embodiment of the invention, a method is presented for sequencing nucleic acid sequences on an array and identifying subsets of nucleic acid sequences on an array, wherein each subset of nucleic acid sequences is isolated from a different source, wherein the method comprises the steps of:

(a) providing at least two samples of randomly fragmented double stranded nucleic acid targets, wherein each of said randomly fragmented double stranded nucleic acid targets is isolated from a different source;
(b) ligating a universal adaptor to the ends of each target fragment of each sample to generate adaptor-target-adaptors of each sample, wherein each of said adaptor-target-adaptors comprises a target fragment flanked by universal adaptor sequences and said universal adaptor comprises a region of double stranded nucleic acid and at least one region of single stranded nucleic acid;
(c) amplifying adaptor-target-adaptors of each sample with two or more sample specific amplification primers to generate amplified nucleic acids, wherein one of said amplification primers comprises a sample specific tag sequence, and wherein amplified nucleic acids of each sample comprise said sample specific tag sequence and said sample specific tag sequence differentiates amplified nucleic acids originating from different samples;
(d) pooling the amplified nucleic acids of different samples;
(e) immobilising the amplified nucleic acids of different samples on an array to generate an array of immobilised fragments;
(f) sequencing the immobilised fragments on the array to determine a sequence read of each immobilised target fragment and identify the sample specific tag sequence of each immobilised fragment, thereby determining both a nucleic acid sequence of said immobilized fragment and identifying the immobilized fragment as a member of a subset of nucleic acids on the array.

In a second embodiment of the invention, a method is presented for sequencing nucleic acid sequences on an array and identifying subsets of nucleic acid sequences on an array, wherein each subset of nucleic acid sequences is isolated from a different source, wherein the method comprises the steps of:

(a) providing at least two samples of randomly fragmented double stranded nucleic acid targets, wherein each of said randomly fragmented double stranded nucleic acid targets is isolated from a different source;
(b) ligating a sample specific tagged adaptor to the ends of each target fragment of each sample to generate adaptor-target-adaptors of each sample, wherein each of said adaptor-target-adaptors comprises a target fragment flanked by tagged adaptor sequences and said tagged adaptor comprises a region of double stranded nucleic acid and at least one region of single stranded nucleic acid and a sample specific tag that differentiates adaptor-target-adaptors originating from different samples;
(c) pooling the adaptor-target-adaptors of different samples to generate a pooled sample of adaptor-target-adaptors;
(d) amplifying the pooled sample of adaptor-target-adaptors with a pair of universal amplification primers to generate an amplified pooled sample;
(e) immobilising the amplified pooled sample on an array to generate an array of immobilised fragments;
(f) sequencing the array to determine a sequence read of each immobilised target fragment and identify the sample specific tag sequence of each immobilised fragment, thereby determining both a nucleic acid sequence of said immobilized fragment and identifying the immobilized fragment as a member of a subset of nucleic acids on the array.

In a third embodiment of the invention, a method is presented for sequencing nucleic acid sequences on an array and identifying subsets of nucleic acid sequences on an array, wherein each subset of nucleic acid sequences is isolated from a different source, wherein the method comprises the steps of:

(a) providing at least two samples of randomly fragmented double stranded nucleic acid targets, wherein each of said randomly fragmented double stranded nucleic acid targets is isolated from a different source;

(b) ligating a sample specific tagged adaptor to the ends of each target fragment of each sample to generate adaptor-target-adaptors of each sample, wherein each of said adaptor-target-adaptors comprises a target fragment flanked by tagged adaptor sequences and said tagged adaptor comprises a region of double stranded nucleic acid and at least one region of single stranded nucleic acid and a sample specific tag that differentiates adaptor-target-adaptors originating from different samples, and wherein the sample specific tag sequence is attached directly to the target fragment in each adaptor-target-adaptor with no intervening nucleotides between the sample specific tag sequence and target fragment sequences;

(c) amplifying adaptor-target-adaptors of each sample with a pair of amplification primers complementary to the sample specific tag sequence to generate amplified nucleic acids from each sample;

(d) pooling the amplified nucleic acids from each sample to generate a pool of amplified nucleic acid samples;

(e) immobilising the pool of amplified nucleic acid samples on an array to generate an array of immobilised fragments;

(f) sequencing the array to determine a sequence read of each immobilised target fragment and identify the sample specific tag sequence of each immobilised fragment, thereby determining both a nucleic acid sequence of said immobilized fragment and identifying the immobilized fragment as a member of a subset of nucleic acids on the array.

In accordance with the first or second embodiment of the invention, sequencing can be performed in two separate reads. In accordance with the third embodiment of the invention, sequencing of the target fragment and the sample specific tag sequence can be performed in a single sequencing read.

With respect to the first, second, or third embodiments, the method encompasses a step wherein the pooled samples are amplified on a solid surface prior to sequencing. In a particular aspect, the solid surface on which amplification is performed is a collection of beads. In a more particular aspect, the collection of beads may be isolated as single beads in an emulsion.

With respect to the first, second, or third embodiments, the method encompasses a step wherein the array of immobilized fragments is amplified prior to sequencing to generate an amplified array. In a particular aspect, an amplified array so produced is a clustered array of amplified single molecules. Such clustered arrays may be formed, for example, by solid-phase nucleic acid amplification or isothermal solid-phase nucleic acid amplification.

The present method encompasses sequencing that involves cycles of ligation with labelled oligonucleotides or cycles of addition of nucleotides. In a particular aspect of the invention, the nucleotides are labelled. In a more particular aspect the nucleotides are labelled with fluorophores.

In an aspect of any of the first, second, or third embodiments of the invention, the sequencing step may be carried out on an array of immobilised beads.

A further aspect of the invention comprises a kit comprising a double stranded nucleic acid adapter and at least two different primer polynucleotides that carry a different tag sequence that does not hybridise to the adapter.

BRIEF DESCRIPTION OF THE FIGURES

FIG. 4 shows numerical data on two sequencing reads obtained from a sample prepared according to the first method of the invention, amplified into an array of clusters and sequenced with two sequencing reads, one for the target and one for the tag.

FIG. 7 shows the embodiment of the method where the first sequencing read is performed, followed by removing the first sequencing primer, hybridising a second sequencing primer to determine the tag sequence, inverting the strand on the surface using a strand resynthesis protocol, and performing a second read at the opposite end of the fragment to the first read to generate a pair of reads from each fragment along with the tag read.

FIG. 8 shows some exemplary data obtained using the method shown in FIG. 7.

FIG. 9 shows the sequence of the various oligonucleotides used in the process

DETAILED DESCRIPTION OF THE INVENTION

Figure 1:
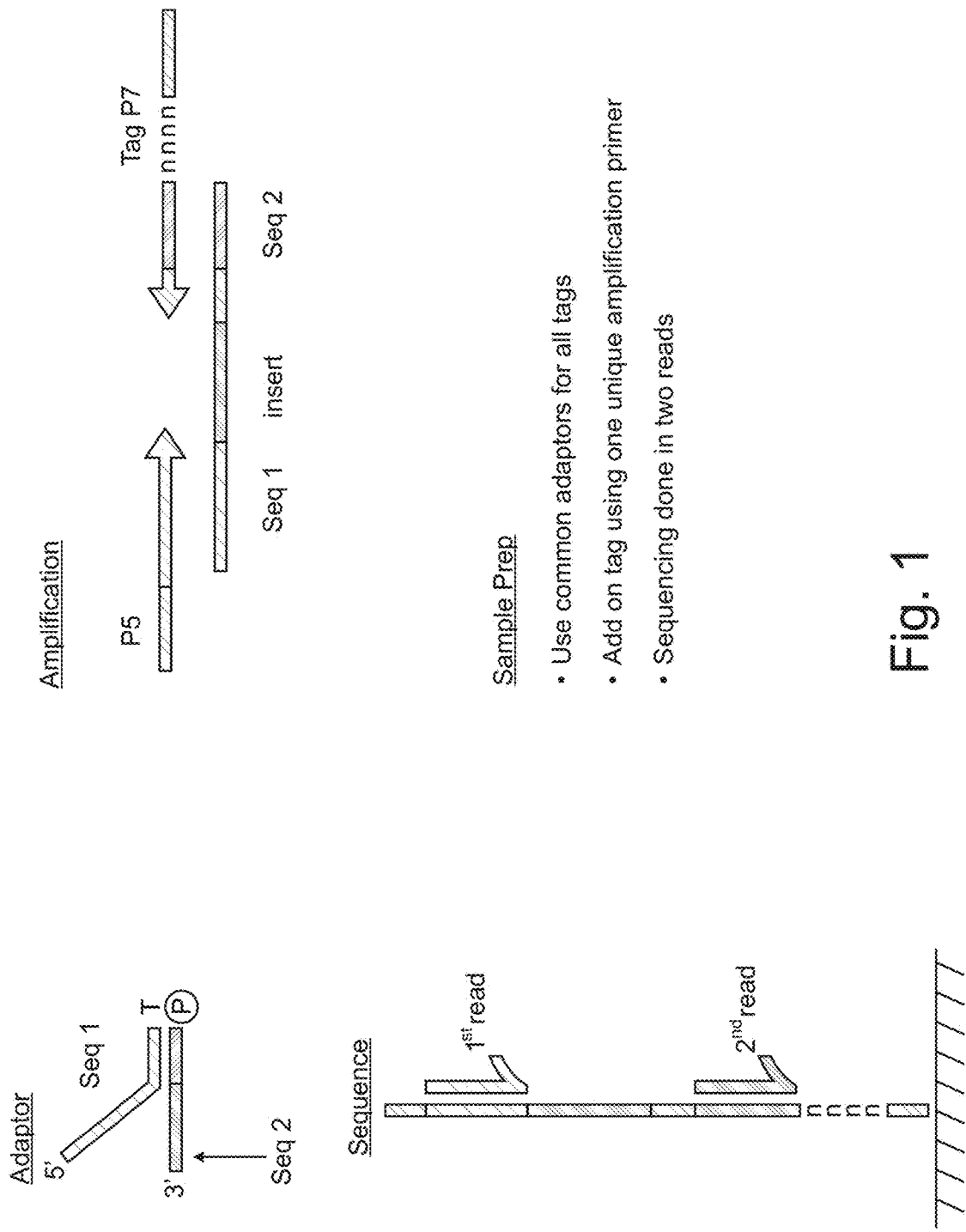
FIG. 1 shows a schematic of an indexed sample construct using the first method of the invention.

The present invention is directed to methods that advance techniques for nucleic acid analysis, such that target nucleic acids from a plurality of sources can be tagged with a unique, identifiable sequence of nucleic acid bases and then sequenced on a single array. As described herein, the presence of a characteristic nucleic acid sequence tag on an immobilised target molecule permits identification of the source of the target, concurrent with a sequence read from the target. This is a dramatic improvement over pre-existing array technologies which generally require a two-step process involving an initial sequencing step for sequencing the pooled nucleic acid targets, followed by a second analysis step wherein the source of the nucleic acid is determined.

The limitations of such pre-existing array technologies are evident in WO 98/44151 and WO 00/18957, for example, which both describe methods of nucleic acid amplification which allow amplification products to be immobilised on a solid support in order to form arrays comprised of clusters or "colonies" formed from a plurality of identical immobilised polynucleotide strands and a plurality of identical immobilised complementary strands. The nucleic acid molecules present in DNA colonies on the clustered arrays prepared according to these methods can provide templates for sequencing reactions, but to date only a single sequencing read can be obtained from each immobilised strand in each colony. The methods described herein allow for two or more reads on a single amplified strand, thereby allowing analysis of the tag sequence independently of the target sequence, and also allowing the possibility of a paired read from the opposite end of each fragment as well as a third read for the tag sequence. The methods also allow the preparation of constructs where the tag sequence is adjacent to the target sequence, and the tag and target are read in a single read, which again can be turned into a paired read methodology if desired.

As will be apparent to the skilled reader, references herein to a particular nucleic acid sequence may, depending on the context, also refer to nucleic acid molecules which comprise the nucleic acid sequence. Sequencing of a target fragment means that a read of the chronological order of bases is established. The bases do not need to be contiguous, although this is preferred, nor does every base on the entire fragment have to be sequenced.

The following passages describe different aspects of the invention in greater detail. Each aspect of the invention may be combined with any other aspect or aspects of the invention unless clearly indicated to the contrary. In particular, any feature indicated as being preferred or advantageous may be combined with any other feature of features indicated as being preferred or advantageous.

The terms 'target nucleic acid sequence', 'target nucleic acid molecule', 'target nucleic acid' and 'target nucleic acid fragment' may be used interchangeably to refer to nucleic acid molecules that it is desired to sequence on an array according to the invention. The target nucleic acid may be essentially any nucleic acid of known or unknown sequence. It may be, for example, a fragment of genomic DNA or cDNA. Sequencing may result in determination of the sequence of the whole, or a part of the target molecule. The targets can be derived from a primary nucleic acid sample that has been randomly fragmented. The targets can be processed into templates suitable for amplification by the placement of universal amplification sequences at the ends of each target fragment. The targets can also be obtained from a primary RNA sample by reverse transcription into cDNA.

As used herein, the term 'polynucleotide' refers to deoxyribonucleic acid (DNA), but where appropriate the skilled artisan will recognise that the method may also be applied to ribonucleic acid (RNA). The terms should be understood to include, as equivalents, analogs of either DNA or RNA made from nucleotide analogs and to be applicable to single stranded (such as sense or antisense) and double stranded polynucleotides. The term as used herein also encompasses cDNA, that is complementary or copy DNA produced from an RNA template, for example by the action of reverse transcriptase.

The primary polynucleotide molecules may originate in double-stranded DNA (dsDNA) form (e.g. genomic DNA fragments, PCR and amplification products and the like) or may have originated in single-stranded form, as DNA or RNA, and been converted to dsDNA form. By way of example, mRNA molecules may be copied into double-stranded cDNAs suitable for use in the method of the invention using standard techniques well known in the art. The precise sequence of the primary polynucleotide molecules is generally not material to the invention, and may be known or unknown.

In a particular embodiment, the primary polynucleotide molecules are RNA molecules. In an aspect of this embodiment, RNA isolated from specific samples is first converted to double-stranded DNA using techniques known in the art. In accordance with the present method, the double-stranded DNA is then tagged or indexed with a sample specific tag. Different preparations of such double-stranded DNA comprising sample specific tags can be generated, in parallel, from RNA isolated from different specific samples. Subsequently, different preparations of double-stranded DNA comprising different sample specific tags can be mixed, sequenced en masse, and the identity of each sequenced fragment determined with respect to the sample from which it was isolated/derived by virtue of the presence of a sample specific tag.

In a particular embodiment, the primary polynucleotide molecules are DNA molecules. More particularly, the primary polynucleotide molecules represent the entire genetic complement of an organism, and are genomic DNA molecules which include both intron and exon sequences (coding sequence), as well as non-coding regulatory sequences such as promoter and enhancer sequences. Although it could be envisaged that particular sub-sets of polynucleotide sequences or genomic DNA could also be used, such as, for example, particular chromosomes. Yet more particularly, the sequence of the primary polynucleotide molecules is not known. Still yet more particularly, the primary polynucleotide molecules are human genomic DNA molecules. The DNA target molecules may be treated chemically or enzymatically either prior to, or subsequent to any random fragmentation processes, and prior to or subsequent to the ligation of the adaptor sequences.

Methods of the invention are especially useful for the parallel sequencing of a large number of relative small samples in the same experiment. In a sequencing platform with a high degree of parallelism, it may be possible to analyse 50-100 million reads in the same experiment, each to a length of 50 bases or more. Thus it may easily be possible to determine more than 5 billion base pairs of sequence from a single experiment. For a genome of 100,000-1 million base pairs, this represents a much larger coverage of each base pair than is actually needed for accurate sequencing. This feature is even more pronounced for viral or mitochondrial genomes or collections of PCR fragments that may be 10,000 base pairs or less. For a 10 kB sample, sequenced in a run of 5 billion base pairs, each base pair will appear on average 500,000 times. For accurate sequencing, it may be desirable for each base pair to appear only 20 times, and thus it will be possible to sequence 25,000 10 kB fragments in the sequencing run. The use of 8 base pair tags gives a possibility of $4^8$ (65536) different samples in the same experiment. For the sake of clarity, sequencing of the tags can be performed in a separate read from the sequencing of the target fragments, so the read length or accuracy of the read from the sample is not lowered by the need to sequence the tags.

For genome sizes of 1 mB, at a depth of 20×, it is possible to sequence 250 samples in a 5 billion base pair experiment. The 250 samples can be coded by as few as a four base tag, but extra bases may be added to ensure accurate analysis. Thus, the primary polynucleotide molecules may be a genome of any organism, but the methods of the present invention may be used to particular advantage when analysing smaller genomes, such as those of bacteria, viruses, mitochondria and the like, which have genome sizes in the regions of a few million base pairs or lower.

Random fragmentation refers to the fragmentation of a polynucleotide molecule in a non-ordered fashion by enzymatic, chemical or mechanical means. Such fragmentation methods are known in the art and utilise standard methods (Sambrook and Russell, Molecular Cloning, A Laboratory Manual, third edition). For the sake of clarity, generating smaller fragments of a larger piece of nucleic acid via specific PCR amplification of such smaller fragments is not equivalent to fragmenting the larger piece of nucleic acid because the larger piece of nucleic acid sequence remains in intact (i.e., is not fragmented by the PCR amplification). Moreover, random fragmentation is designed to produce fragments irrespective of the sequence identity or position of nucleotides comprising and/or surrounding the break. More particularly, the random fragmentation is by mechanical means such as nebulisation or sonication to produce fragments of about 50 base pairs in length to about 1500 base pairs in length, still more particularly 50-700 base pairs in length, yet more particularly 50-400 base pairs in length. Most particularly, the method is used to generate smaller fragments of from 50-150 base pairs in length.

Fragmentation of polynucleotide molecules by mechanical means (nebulization, sonication and Hydroshear for example) results in fragments with a heterogeneous mix of blunt and 3'- and 5'-overhanging ends. It is therefore desirable to repair the fragment ends using methods or kits (such as the Lucigen DNA terminator End Repair Kit) known in the art to generate ends that are optimal for insertion, for example, into blunt sites of cloning vectors. In a particular embodiment, the fragment ends of the population of nucleic acids are blunt ended. More particularly, the fragment ends are blunt ended and phosphorylated. The phosphate moiety can be introduced via enzymatic treatment, for example, using polynucleotide kinase.

In a particular embodiment, the target polynucleotide sequences are prepared with single overhanging nucleotides by, for example, activity of certain types of DNA polymerase such as Taq polymerase or Klenow exo minus polymerase which has a nontemplate-dependent terminal transferase activity that adds a single deoxynucleotide, for example, deoxyadenosine (A) to the 3' ends of, for example, PCR products. Such enzymes can be utilised to add a single nucleotide 'A' to the blunt ended 3' terminus of each strand of the target polynucleotide duplexes. Thus, an 'A' could be added to the 3' terminus of each end repaired duplex strand of the target polynucleotide duplex by reaction with Taq or Klenow exo minus polymerase, whilst the adaptor polynucleotide construct could be a T-construct with a compatible 'T' overhang present on the 3' terminus of each duplex region of the adaptor construct. This end modification also prevents self-ligation of both vector and target such that there is a bias towards formation of the combined ligated adaptor-target sequences.

The method of the invention utilises nucleic acid sequence tags as markers characteristic of the source of particular target molecules on the array. A nucleic acid sequence tag characteristic of the source is attached to each of the target molecules in each isolated sample before the sample is immobilised for sequencing. The tag is not itself formed by part of the target nucleic acid molecule, but becomes part of the template for amplification. Generally the tag will be a synthetic sequence of nucleotides which is added to the target as part of the template preparation step. Accordingly, a sample specific tag is a nucleic acid sequence tag which is attached to each of the target molecules of a particular sample, the presence of which is indicative of or is used to identify the sample or source from which the target molecules were isolated.

Preferably the nucleic acid sequence tag may be up to 20 nucleotides in length, more preferably 1-10 nucleotides, and most preferably 4-6 nucleotides in length. A four nucleotide tag gives a possibility of multiplexing 256 samples on the same array, a six base tag enables 4096 samples to be processed on the same array.

Figure 2:
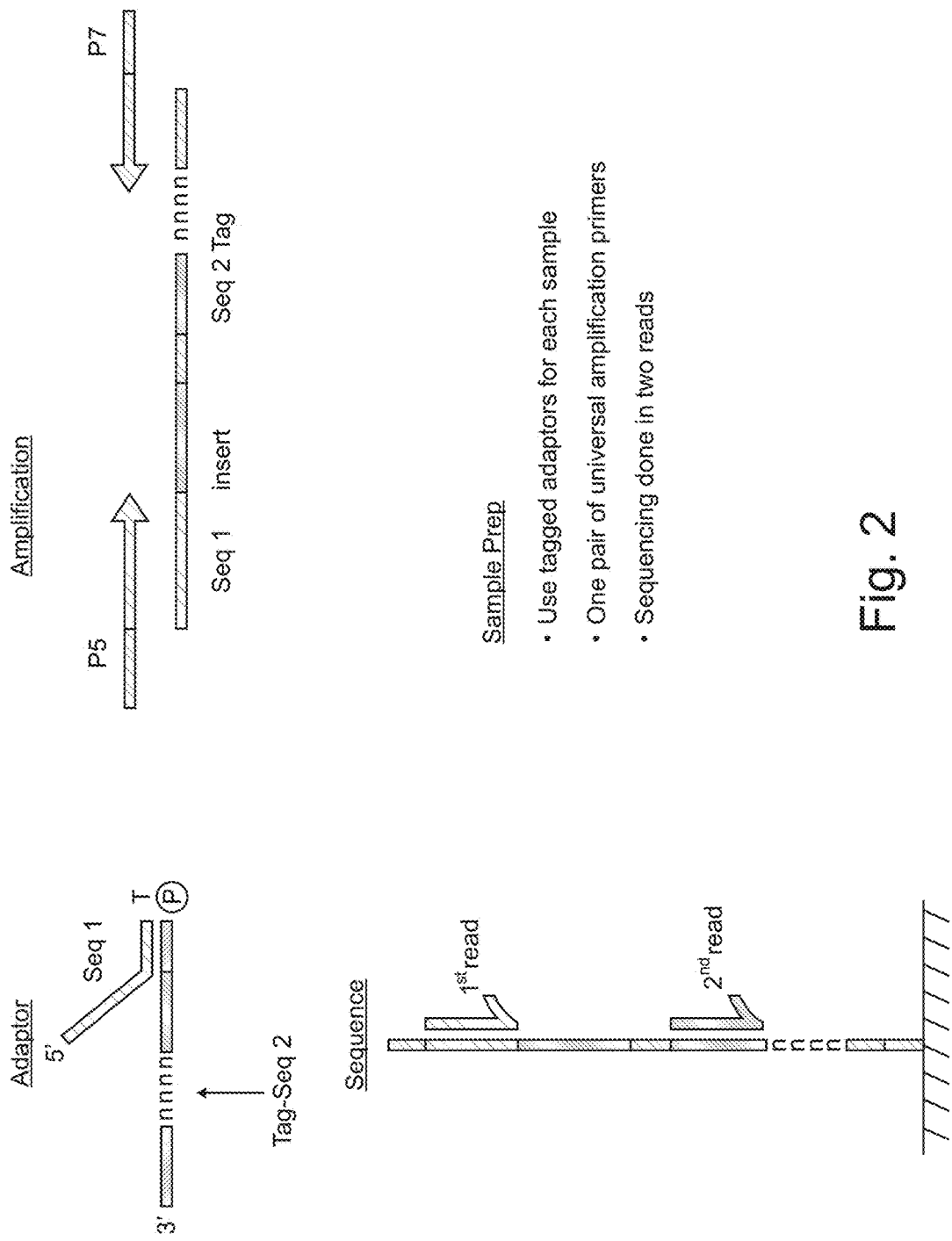
FIG. 2 shows a schematic of an indexed sample construct using the second method of the invention.
Figure 3:
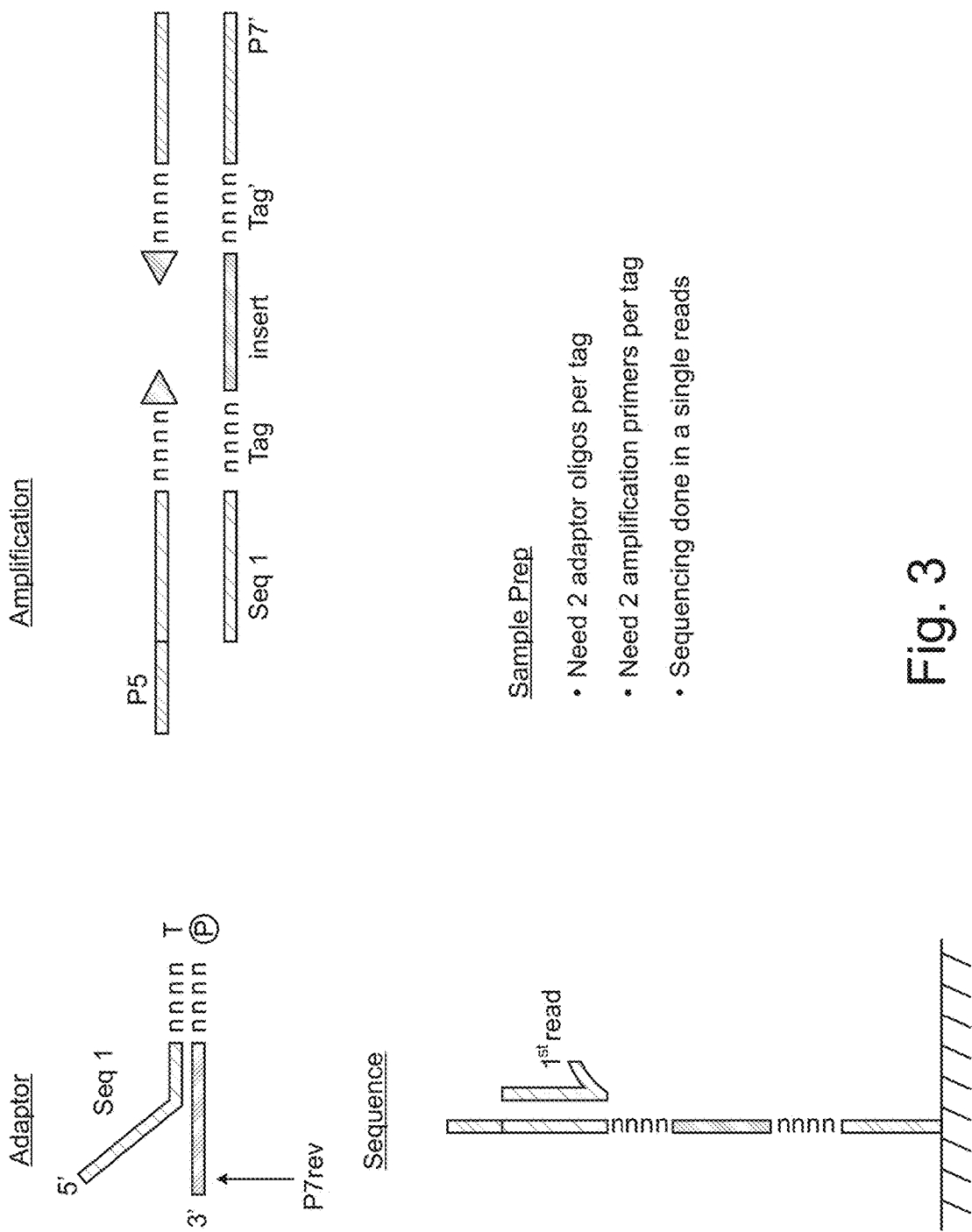
FIG. 3 shows a schematic of an indexed sample construct using the third method of the invention.
Figure 5:
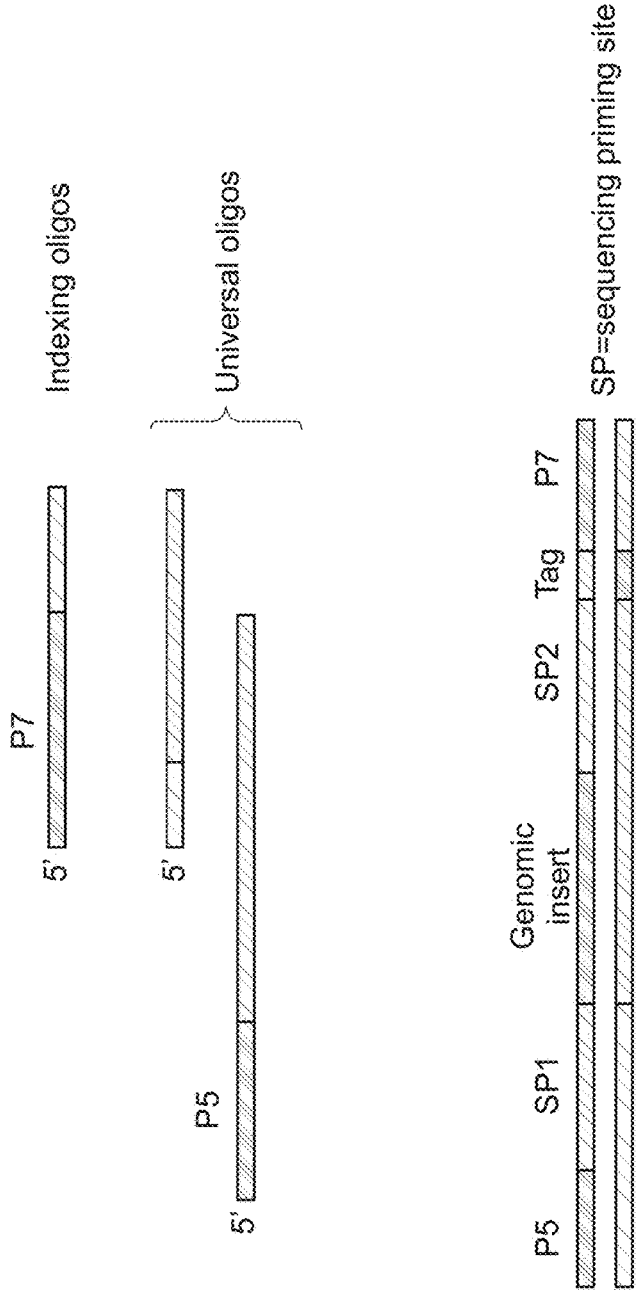
FIG. 5 shows the concept of tagging a sample for use in a paired end reading process

In the first embodiment of the invention, the tag sequences are introduced in a two step process involving ligation of an adaptor that is common to all samples and amplification with a tagged amplification primer. See FIGS. 1 and 6. In the second embodiment the tags are on the adaptor, and the amplification can be performed with universal amplification primers. See FIG. 2. In the third embodiment, the tags are on the adaptors, but at the terminus of the duplex region such that the tag and target sequences are contiguous. See FIG. 3. The third embodiment allows for the sequencing to be performed in a single read, but requires both strands of the adaptor to be modified and therefore requires more oligonucleotides as two unique adaptor strands are needed for each sample.

In each embodiment, the target nucleic acids of each specific fragmented sample are treated by first ligating identical adaptor polynucleotide molecules ('mismatched adaptors', the general features of which are defined below, and further described in copending application US 20070128624, the contents of which are incorporated herein by reference in their entirety) to the 5' and 3' ends of the target polynucleotide duplexes (which may be of known, partially known or unknown sequence) to form adaptor-target constructs and then carrying out an initial primer extension reaction in which extension products complementary to both strands of each individual adaptor-target construct are formed. The resulting primer extension products, and optionally amplified copies thereof, collectively provide a library of template polynucleotides. The term library refers to the collection of target fragments containing known common sequences at their 3' and 5' ends, and may also be referred to as a 3' and 5' modified library.

Depending on the embodiment of the invention, the adaptors may be universal for all samples, or one or both strands of the duplexes may carry the tag sequence to code or track the identity of the samples.

The adaptor polynucleotides used in the method of the invention are referred to herein as 'mismatched' adaptors because, as will be explained in detail herein, it is essential that the adaptors include a region of sequence mismatch, i.e., they must not be formed by annealing of fully complementary polynucleotide strands.

Mismatched adaptors for use in the invention are formed by annealing of two partially complementary polynucleotide strands so as to provide, when the two strands are annealed, at least one double-stranded region and at least one unmatched single-stranded region.

The 'double-stranded region' of the adaptor is a short double-stranded region, typically comprising 5 or more consecutive base pairs, formed by annealing of the two partially complementary polynucleotide strands. This term refers to a double-stranded region of nucleic acid in which the two strands are annealed and does not imply any particular structural conformation.

Generally it is advantageous for the double-stranded region to be as short as possible without loss of function. In this context, 'function' refers to the ability of the double-stranded region to form a stable duplex under standard reaction conditions for an enzyme-catalysed nucleic acid ligation reaction, which will be well known to the skilled reader (e.g. incubation at a temperature in the range of 4° C. to 25° C. in a ligation buffer appropriate for the enzyme), such that the two strands forming the adaptor remain partially annealed during ligation of the adaptor to a target molecule. It is not absolutely necessary for the double-stranded region to be stable under the conditions typically used in the annealing steps of primer extension or PCR reactions.

Since identical adaptors are ligated to both ends of each target molecule, the target sequence in each adaptor-target construct will be flanked by complementary sequences derived from the double-stranded region of the adaptors. The longer the double-stranded region, and hence the complementary sequences derived therefrom in the adaptor-target constructs, the greater the possibility that the adaptor-target construct is able to fold back and base-pair to itself in these regions of internal self-complementarity under the annealing conditions used in primer extension and/or PCR. It is, therefore, generally preferred for the double-stranded region to be 20 or less, 15 or less, or 10 or less base pairs in length in order to reduce this effect. The stability of the double-stranded region may be increased, and hence its length potentially reduced, by the inclusion of non-natural nucleotides which exhibit stronger base-pairing than standard Watson-Crick base pairs.

It is preferred, but not absolutely essential, for the two strands of the adaptor to be 100% complementary in the double-stranded region. It will be appreciated that one or more nucleotide mismatches may be tolerated within the double-stranded region, provided that the two strands are capable of forming a stable duplex under standard ligation conditions.

Adaptors for use in the invention will generally include a double-stranded region forming the 'ligatable' end of the adaptor, i.e. the end that is joined to a target polynucleotide in the ligation reaction. The ligatable end of the adaptor may be blunt or, in other embodiments, short 5' or 3' overhangs of one or more nucleotides may be present to facilitate/promote ligation. The 5' terminal nucleotide at the ligatable end of the adaptor is phosphorylated to enable phosphodiester linkage to a 3' hydroxyl group on the target polynucleotide.

The term 'unmatched region' refers to a region of the adaptor wherein the sequences of the two polynucleotide strands forming the adaptor exhibit a degree of non-complementarity such that the two strands are not capable of fully annealing to each other under standard annealing conditions for a primer extension or PCR reaction. The unmatched region(s) may exhibit some degree of annealing under standard reaction conditions for an enzyme-catalysed ligation reaction, provided that the two strands revert to single stranded form under annealing conditions in an amplification reaction.

It is to be understood that the 'unmatched region' is provided by different portions of the same two polynucleotide strands which form the double-stranded region(s). Mismatches in the adaptor construct can take the form of one strand being longer than the other, such that there is a single stranded region on one of the strands, or a sequence selected such that the two strands do not hybridise, and thus form a single stranded region on both strands. The mismatches may also take the form of 'bubbles', wherein both ends of the adaptor construct(s) are capable of hybridising to each other and forming a duplex, but the central region is not. The portion of the strand(s) forming the unmatched region are not annealed under conditions in which other portions of the same two strands are annealed to form one or more double-stranded regions. For avoidance of doubt it is to be understood that a single-stranded or single base overhang at the 3' end of a polynucleotide duplex that subsequently undergoes ligation to the target sequences does not constitute an 'unmatched region' in the context of this invention.

The lower limit on the length of the unmatched region will typically be determined by function, for example, the need to provide a suitable sequence for binding of a primer for primer extension, PCR and/or sequencing. Theoretically there is no upper limit on the length of the unmatched region, except that in general it is advantageous to minimise the overall length of the adaptor, for example, in order to facilitate separation of unbound adaptors from adaptor-target constructs following the ligation step. Therefore, it is generally preferred that the unmatched region should be less than 50, or less than 40, or less than 30, or less than 25 consecutive nucleotides in length.

The precise nucleotide sequence of the adaptors is generally not material to the invention and may be selected by the user such that the desired sequence elements are ultimately included in the common sequences of the library of templates derived from the adaptors to, for example, provide binding sites for particular sets of universal amplification primers and/or sequencing primers. Additional sequence elements may be included, for example, to provide binding sites for sequencing primers which will ultimately be used in sequencing of template molecules in the library, or products derived from amplification of the template library, for example on a solid support.

Although the precise nucleotide sequence of the adaptor is generally non-limiting to the invention, the sequences of the individual strands in the unmatched region should be such that neither individual strand exhibits any internal self-complementarity which could lead to self-annealing, formation of hairpin structures, etc. under standard annealing conditions. Self-annealing of a strand in the unmatched region is to be avoided as it may prevent or reduce specific binding of an amplification primer to this strand.

The mismatched adaptors are preferably formed from two strands of DNA, but may include mixtures of natural and non-natural nucleotides (e.g. one or more ribonucleotides) linked by a mixture of phosphodiester and non-phosphodiester backbone linkages. Other non-nucleotide modifications may be included such as, for example, biotin moieties, blocking groups and capture moieties for attachment to a solid surface, as discussed in further detail below.

The adaptor constructs may contain exonuclease resistant modifications such as phosphorothioate linkages. Such modifications reduce the number of adaptor-dimers present in the library, since the two adaptors can not undergo ligation without removal of their non complementary overhangs. The adaptors can be treated with an exonuclease enzyme prior to the ligation reaction with the target, to ensure that the overhanging ends of the strands can not be removed during the ligation process. Treatment of the adaptors in this manner reduces the formation of the adaptor-dimers at the ligation step.

Ligation methods are known in the art and utilise standard methods (Sambrook and Russell, Molecular Cloning, A Laboratory Manual, third edition). Such methods utilise ligase enzymes such as DNA ligase to effect or catalyse joining of the ends of the two polynucleotide strands of, in this case, the adaptor duplex construct and the target polynucleotide duplexes, such that covalent linkages are formed. The adaptor duplex construct may contain a 5'-phosphate moiety in order to facilitate ligation to the target 3'-OH. The target contains a 5'-phosphate moiety, either residual from the shearing process, or added using an enzymatic treatment step, and has been end repaired, and optionally extended by an overhanging base or bases, to give a 3'-OH suitable for ligation. In this context, joining means covalent linkage of polynucleotide strands which were not previously covalently linked. In a particular aspect of the invention, such joining takes place by formation of a phosphodiester linkage between the two polynucleotide strands, but other means of covalent linkage (e.g. non-phosphodiester backbone linkages) may be used.

Optionally the combined ligated polynucleotide sequences and unligated adaptor polynucleotide constructs may be purified from any components of the ligation reaction, such as enzymes, buffers, salts and the like. Suitable purification methods are known in the art and utilise standard methods (Sambrook and Russell, Molecular Cloning, A Laboratory Manual, third edition).

In a next step according to the invention an amplification reaction is prepared. The contents of an amplification reaction are known by one skilled in the art and include appropriate substrates (such as dNTPs), enzymes (e.g. a DNA polymerase) and buffer components required for an amplification reaction. Generally amplification reactions require at least two amplification primers, often denoted 'forward' and 'reverse' primers (primer oligonucleotides) that are capable of annealing specifically to a part of the polynucleotide sequence to be amplified under conditions encountered in the primer annealing step of each cycle of an amplification reaction. In certain embodiments the forward and reverse primers may be identical. Thus the primer oligonucleotides must include an 'adaptor-target specific portion', being a sequence of nucleotides capable of annealing to a part of, that is, a primer-binding sequence, in the polynucleotide molecule to be amplified (or the complement thereof if the template is viewed as a single strand) during the annealing step.

Figure 6A:
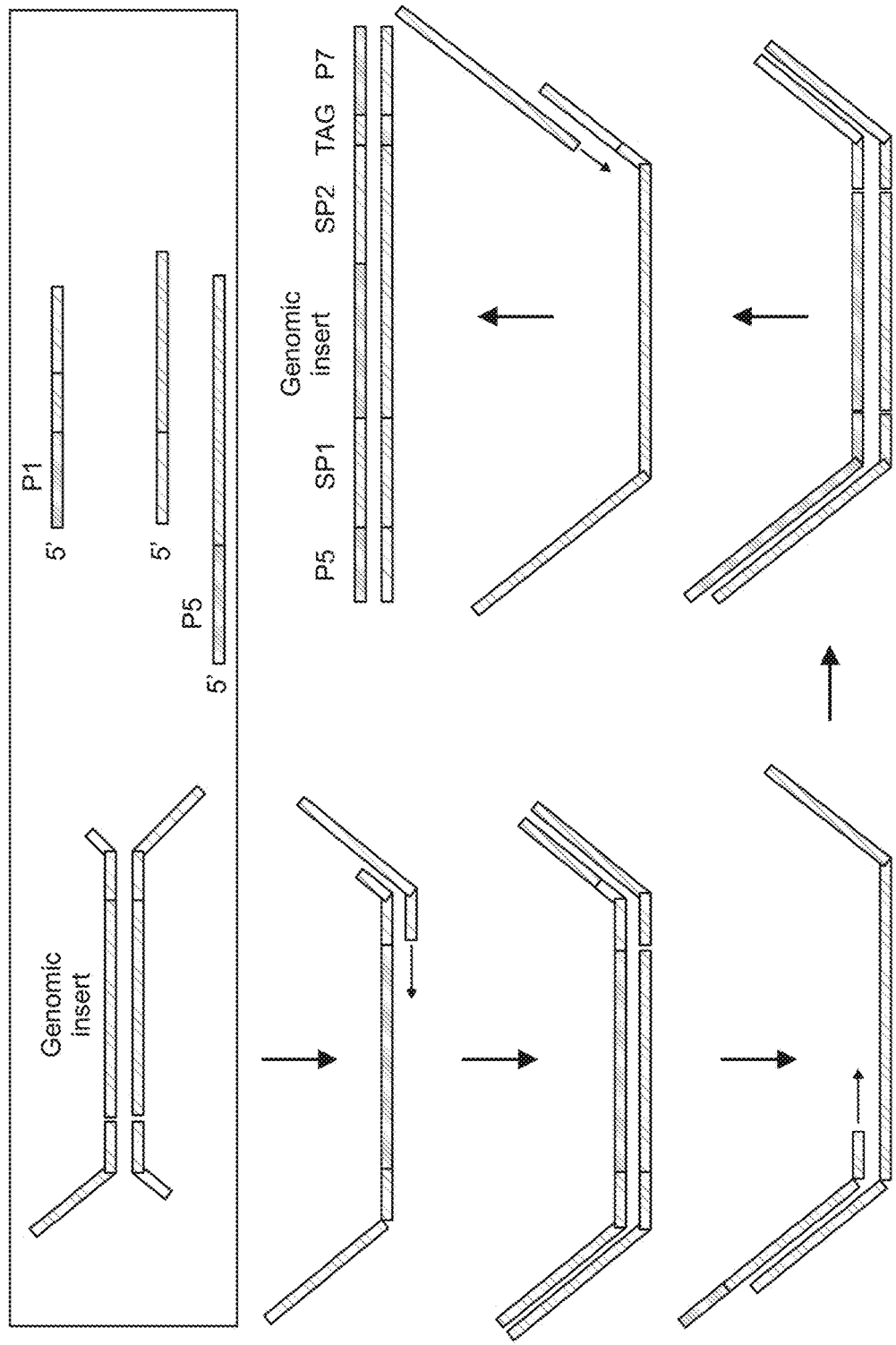
FIG. 6a shows a nested PCR reaction using three amplification primers, one of which carries the tag.

Depending on the embodiment of the invention, the amplification primers may be universal for all samples, or one of the forward or reverse primers may carry the tag sequence that codes for the sample source. The amplification primers may hybridise across the tag region of the ligated adaptor, in which case unique primers will be needed for each sample nucleic acid. The amplification reaction may be performed with more than two amplification primers. In order to prevent the amplification of ligated adapter-adapter dimers, the amplification primers can be modified to contain nucleotides that hybridise across the whole of the ligated adapter and into the ligated template (or the dNTP's attached to the 3' end thereof). This first amplification primer can be modified and treated to help prevent exonuclease digestion of the strands, and thus it may be advantageous to have a first amplification primer that is universal and can amplify all samples rather than modifying and treating each of the tagged primers separately. The tagged primer can be introduced as a sample specific third primer in the amplification reaction, but does not need to be specially modified and treated to reduce exonuclease digestion. The nested PCR approach is shown in FIG. 6. In the case of this embodiment the third amplification primer that carries the tag needs to contain a sequence that is the same as at least a portion of the first amplification primer such that it can be used to amplify the duplex resulting from extension of the first amplification primer.

In the context of the present invention, the term 'polynucleotide molecule to be amplified' refers to the original or starting adaptor-target-adaptor sequence added to the amplification reaction. The 'adaptor-target specific portion' in the forward and reverse amplification primers refers to a sequence capable of annealing to the original or initial adaptor-target-adaptor present at the start of the amplification reaction and reference to the length of the 'adaptor-target specific portion' relates to the length of the sequence in the primer which anneals to the starting adaptor-target. It will be appreciated that if the primers contain any nucleotide sequence which does not anneal to the starting adaptor-target in the first amplification cycle then this sequence may be copied into the amplification products (assuming the primer does not contain a moiety which prevents read-through of the polymerase). Hence the amplified template strands produced in the first and subsequent cycles of amplification may be longer than the starting adaptor-target strands.

Figure 6B:
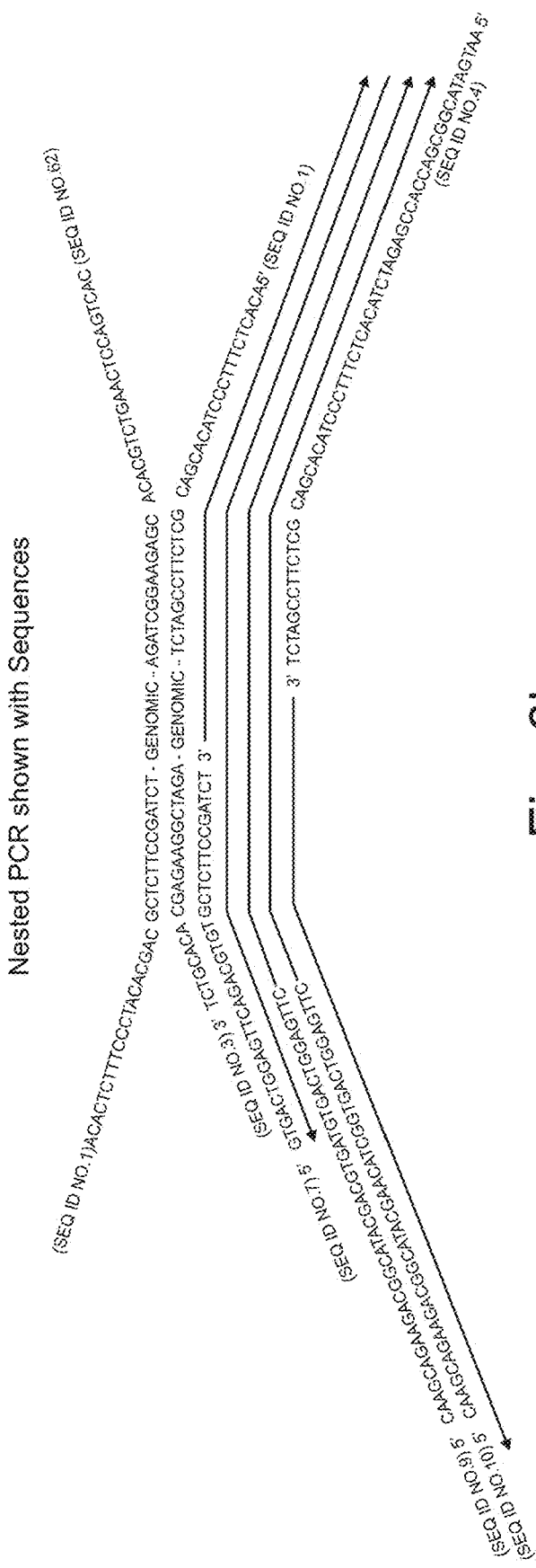
FIG. 6b shows the same nested PCR concept as FIG. 6a, but with the benefit of the sequences of various exemplary adapters and primers.

Since the mis-matched adapters can be different lengths, the length of adapter sequence added to the 3' and 5' ends of each strand may be different. The amplification primers may also be of different lengths to each other, and may hybridise to different lengths of the adapter, and therefore the length added to the ends of each strand can be controlled. In the case of nested PCR, the three or more amplification primers can be designed to be longer than the primer used to amplify the previous amplicon, so the length of the added nucleotides is fully controllable and may be hundreds of base pairs if desired. In the example shown in FIG. 6b, the first amplification primer adds 13 bases to the ligated adapter, and the third amplification primer adds a further 27 bases such that one end of the amplicon is 40 bases longer than the short arm of adapter-target construct. The short arm of the adapter is 20 bases in length, meaning that the prepared template comprises the genomic region plus 60 added bases at the end. In FIG. 6b, the second amplification primer is 25 bases longer than the long arm of adapter, which is 32 bases in length plus the additional T that hybridises across the dATP nucleoside added to the genomic sample. Thus the prepared template comprises the genomic fragment, plus the added dATP, plus 57 known bases. Thus in full, one strand of each template duplex comprises from the 5' end: 60 known bases, T, the genomic fragment, A, 57 known bases-3' end. This strand is fully complementary to a sequence: 5'-57 known bases, T, genomic fragment, A, 60 known bases-3' end. The length 57 and 6 are arbitrary, and shown for the purpose of clarification, and should not be viewed as limiting. The length of the added sequences may be 20-100 bases or more depending on the desired experimental design.

The forward and reverse primers may be of sufficient length to hybridise to the whole of the adaptor sequence and at least one base of the target sequence (or the nucleotide dNTP added as a 3'-overhang on the target strands). The forward and reverse primers may also contain a region that extends beyond the adaptor construct, and therefore the amplification primers may be at least 20-100 bases in length. The forward and reverse primers may be of significantly different lengths; for example one may be 20-40 bases, whereas the other one may be 40-100 bases in length. The nucleotide sequences of the adaptor-target specific portions of the forward and reverse primers are selected to achieve specific hybridisation to the adaptor-target sequences to be amplified under the conditions of the annealing steps of the amplification reaction, whilst minimising non-specific hybridisation to any other target sequences present.

Skilled readers will appreciate that it is not strictly required for the adaptor-target specific portion to be 100% complementary, a satisfactory level of specific annealing can be achieved with less than perfectly complementary sequences. In particular, one or two mis-matches in the adaptor-target specific portion can usually be tolerated without adversely affecting specificity for the template. Therefore the term 'adaptor-target specific portion' should not be interpreted as requiring 100% complementarity with the adaptor-target. However, the requirement that the primers do not anneal non-specifically to regions of the adaptor-target other than their respective primer-binding sequences must be fulfilled.

Amplification primers are generally single stranded polynucleotide structures. They may also contain a mixture of natural and non-natural bases and also natural and non-natural backbone linkages, provided that any non-natural modifications do not preclude function as a primer—that being defined as the ability to anneal to a template polynucleotide strand during conditions of the amplification reaction and to act as an initiation point for synthesis of a new polynucleotide strand complementary to the template strand.

Primers may additionally comprise non-nucleotide chemical modifications, for example phosphorothioates to increase exonuclease resistance, again provided such that modifications do not prevent primer function. Modifications may, for example, facilitate attachment of the primer to a solid support, for example a biotin moiety. Certain modifications may themselves improve the function of the molecule as a primer, or may provide some other useful functionality, such as providing a site for cleavage to enable the primer (or an extended polynucleotide strand derived therefrom) to be cleaved from a solid support.

In an embodiment wherein tags are attached to the adaptors, the amplification can be carried out on either the pooled or unpooled samples. In an embodiment wherein universal adaptors are used, tags must be part of the amplification primers, and therefore, each sample must be amplified independently prior to pooling. The pooled nucleic acid samples can then be processed for sequencing Preparation of Immobilised Samples for Sequencing The pooled sample can then be immobilised in preparation for sequencing. Sequencing can be performed as an array of single molecules, or can be amplified prior to sequencing. The amplification can be carried out using one or more immobilised primers. The immobilised primer(s) can be a lawn on a planar surface, or on a pool of beads. The pool of beads can be isolated into an emulsion with a single bead in each 'compartment' of the emulsion. At a concentration of only one template per 'compartment', only a single template is amplified on each bead.

The term 'solid-phase amplification' as used herein refers to any nucleic acid amplification reaction carried out on or in association with a solid support such that all or a portion of the amplified products are immobilised on the solid support as they are formed. In particular, the term encompasses solid-phase polymerase chain reaction (solid-phase PCR) and solid phase isothermal amplification which are reactions analogous to standard solution phase amplification, except that one or both of the forward and reverse amplification primers is/are immobilised on the solid support. Solid phase PCR covers systems such as emulsions, wherein one primer is anchored to a bead and the other is in free solution, and colony formation in solid phase gel matrices wherein one primer is anchored to the surface, and one is in free solution.

Although the invention encompasses 'solid-phase' amplification methods in which only one amplification primer is immobilised (the other primer usually being present in free solution), it is preferred for the solid support to be provided with both the forward and the reverse primers immobilised. In practice, there will be a 'plurality' of identical forward primers and/or a 'plurality' of identical reverse primers immobilised on the solid support, since the amplification process requires an excess of primers to sustain amplification. References herein to forward and reverse primers are to be interpreted accordingly as encompassing a 'plurality' of such primers unless the context indicates otherwise.

As will be appreciated by the skilled reader, any given amplification reaction requires at least one type of forward primer and at least one type of reverse primer specific for the template to be amplified. However, in certain embodiments the forward and reverse primers may comprise template-specific portions of identical sequence, and may have entirely identical nucleotide sequence and structure (including any non-nucleotide modifications). In other words, it is possible to carry out solid-phase amplification using only one type of primer, and such single-primer methods are encompassed within the scope of the invention. Other embodiments may use forward and reverse primers which contain identical template-specific sequences but which differ in some other structural features. For example one type of primer may contain a non-nucleotide modification which is not present in the other.

In all embodiments of the invention, primers for solid-phase amplification are preferably immobilised by single point covalent attachment to the solid support at or near the 5' end of the primer, leaving the template-specific portion of the primer free to anneal to its cognate template and the 3' hydroxyl group free for primer extension. Any suitable covalent attachment means known in the art may be used for this purpose. The chosen attachment chemistry will depend on the nature of the solid support, and any derivatisation or functionalisation applied to it. The primer itself may include a moiety, which may be a non-nucleotide chemical modification, to facilitate attachment. In a particular embodiment, the primer may include a sulphur-containing nucleophile, such as phosphorothioate or thiophosphate, at the 5' end. In the case of solid-supported polyacrylamide hydrogels (as described below), this nucleophile will bind to a bromoacetamide group present in the hydrogel. A more particular means of attaching primers and templates to a solid support is via 5' phosphorothioate attachment to a hydrogel comprised of polymerised acrylamide and N-(5-bromoacetamidylpentyl) acrylamide (BRAPA), as described fully in WO05065814.

Certain embodiments of the invention may make use of solid supports comprised of an inert substrate or matrix (e.g. glass slides, polymer beads, etc) which has been "functionalised", for example by application of a layer or coating of an intermediate material comprising reactive groups which permit covalent attachment to biomolecules, such as polynucleotides. Examples of such supports include, but are not limited to, polyacrylamide hydrogels supported on an inert substrate such as glass. In such embodiments, the biomolecules (e.g. polynucleotides) may be directly covalently attached to the intermediate material (e.g. the hydrogel), but the intermediate material may itself be non-covalently attached to the substrate or matrix (e.g. the glass substrate). The term "covalent attachment to a solid support" is to be interpreted accordingly as encompassing this type of arrangement.

The pooled samples may be amplified on beads wherein each bead contains a forward and reverse amplification primer. In a particular embodiment, the library of templates prepared according to the first, second or third aspects of the invention is used to prepare clustered arrays of nucleic acid colonies, analogous to those described in US20050100900, U.S. Pat. No. 7,115,400, WO 00/18957 and WO 98/44151, the contents of which are incorporated herein by reference in their entirety, by solid-phase amplification and more particularly solid phase isothermal amplification. The terms 'cluster' and 'colony' are used interchangeably herein to refer to a discrete site on a solid support comprised of a plurality of identical immobilised nucleic acid strands and a plurality of identical immobilised complementary nucleic acid strands. The term 'clustered array' refers to an array formed from such clusters or colonies. In this context the term 'array' is not to be understood as requiring an ordered arrangement of clusters.

The term solid phase, or surface, is used to mean either a planar array wherein primers are attached to a flat surface, for example, glass, silica or plastic microscope slides or similar flow cell devices; beads, wherein either one or two primers are attached to the beads and the beads are amplified; or an array of beads on a surface after the beads have been amplified.

Clustered arrays can be prepared using either a process of thermocycling, as described in WO9844151, or a process whereby the temperature is maintained as a constant, and the cycles of extension and denaturing are performed using changes of reagents. Such isothermal amplification methods are described in patent application numbers WO0246456 and US20080009420 (Isothermal methods for creating clonal single molecule arrays), which are incorporated herein by reference in their entirety. Due to the lower temperatures required in the isothermal process, this is particularly preferred.

Use in Sequencing/Methods of Sequencing

The invention also encompasses methods of sequencing amplified nucleic acids generated by solid-phase amplification. Thus, the invention provides a method of nucleic acid sequencing comprising amplifying a pool of nucleic acid templates using solid-phase amplification as described above and carrying out a nucleic acid sequencing reaction to determine the sequence of the whole or a part of at least one amplified nucleic acid strand produced in the solid-phase amplification reaction, as well as the sequence of the tag that codes for the identity of the sample.

Sequencing can be carried out using any suitable sequencing technique, wherein nucleotides are added successively to a free 3' hydroxyl group, resulting in synthesis of a polynucleotide chain in the 5' to 3' direction. The nature of the nucleotide added is preferably determined after each nucleotide addition. Sequencing techniques using sequencing by ligation, wherein not every contiguous base is sequenced, and techniques such as massively parallel signature sequencing (MPSS) where bases are removed from, rather than added to the strands on the surface are also within the scope of the invention, as are techniques using detection of pyrophosphate release (pyrosequencing). Such pyrosequencing based techniques are particularly applicable to sequencing arrays of beads where the beads have been amplified in an emulsion such that a single template from the library molecule is amplified on each bead.

The initiation point for the sequencing reaction may be provided by annealing of a sequencing primer to a product of the solid-phase amplification reaction. In this connection, one or both of the adaptors added during formation of the template library may include a nucleotide sequence which permits annealing of a sequencing primer to amplified products derived by whole genome or solid-phase amplification of the template library.

Depending on the embodiment of the invention, the tag sequence and fragment sequence may be determined in a single read from a single sequencing primer, or in multiple reads from two sequencing primers. In the case of two reads from two sequencing primers, the 'tag read' and the 'fragment read' can be performed in either order, with a suitable denaturing step to remove the annealed primer after the first sequencing read is completed. Suitable denaturing steps may include formamide, hydroxide or heat as described elsewhere.

The products of solid-phase amplification reactions wherein both forward and reverse amplification primers are covalently immobilised on the solid surface are so-called 'bridged' structures formed by annealing of pairs of immobilised polynucleotide strands and immobilised complementary strands, both strands being attached to the solid support at the 5' end. Arrays comprised of such bridged structures provide inefficient templates for nucleic acid sequencing, since hybridisation of a conventional sequencing primer to one of the immobilised strands is not favoured compared to annealing of this strand to its immobilised complementary strand under standard conditions for hybridisation.

In order to provide more suitable templates for nucleic acid sequencing, it is preferred to remove substantially all or remove or displace at least a portion of one of the immobilised strands in the 'bridged' structure in order to generate a template which is at least partially single-stranded. The portion of the template which is single-stranded will thus be available for hybridisation to a sequencing primer. The process of removing all or a portion of one immobilised strand in a 'bridged' double-stranded nucleic acid structure may be referred to herein as 'linearisation', and is described in further detail in WO07010251, the contents of which are incorporated herein by reference in their entirety.

Bridged template structures may be linearised by cleavage of one or both strands with a restriction endonuclease or by cleavage of one strand with a nicking endonuclease. Other methods of cleavage can be used as an alternative to restriction enzymes or nicking enzymes, including inter alia chemical cleavage (e.g. cleavage of a diol linkage with periodate), cleavage of abasic sites by cleavage with endonuclease (for example 'USER', as supplied by NEB, part number M5505S), or by exposure to heat or alkali, cleavage of ribonucleotides incorporated into amplification products otherwise comprised of deoxyribonucleotides, photochemical cleavage or cleavage of a peptide linker.

It will be appreciated that a linearization step may not be essential if the solid-phase amplification reaction is performed with only one primer covalently immobilised and the other in free solution.

Following the cleavage step, regardless of the method used for cleavage, the product of the cleavage reaction may be subjected to denaturing conditions in order to remove the portion(s) of the cleaved strand(s) that are not attached to the solid support. Suitable denaturing conditions, for example sodium hydroxide solution, formamide solution or heat, will be apparent to the skilled reader with reference to standard molecular biology protocols (Sambrook et al., 2001, *Molecular Cloning, A Laboratory Manual,* 3rd Ed, Cold Spring Harbor Laboratory Press, Cold Spring Harbor Laboratory Press, NY; Current Protocols, eds Ausubel et al.). Denaturation results in the production of a sequencing template which is partially or substantially single-stranded. A sequencing reaction may then be initiated by hybridisation of a sequencing primer to the single-stranded portion of the template.

Thus, the invention encompasses methods wherein the nucleic acid sequencing reaction comprises hybridising a sequencing primer to a single-stranded region of a linearised amplification product, sequentially incorporating one or more nucleotides into a polynucleotide strand complementary to the region of amplified template strand to be sequenced, identifying the base present in one or more of the incorporated nucleotide(s) and thereby determining the sequence of a region of the template strand.

One preferred sequencing method which can be used in accordance with the invention relies on the use of modified nucleotides having removable 3' blocks, for example as described in WO04018497 and U.S. Pat. No. 7,057,026, the contents of which are incorporated herein by reference in their entirety. Once the modified nucleotide has been incorporated into the growing polynucleotide chain complementary to the region of the template being sequenced there is no free 3'-OH group available to direct further sequence extension and therefore the polymerase can not add further nucleotides. Once the nature of the base incorporated into the growing chain has been determined, the 3' block may be removed to allow addition of the next successive nucleotide. By ordering the products derived using these modified nucleotides, it is possible to deduce the DNA sequence of the DNA template. Such reactions can be done in a single experiment if each of the modified nucleotides has a different label attached thereto, known to correspond to the particular base, to facilitate discrimination between the bases added during each incorporation step. Alternatively, a separate reaction may be carried out containing each of the modified nucleotides separately.

The modified nucleotides may carry a label to facilitate their detection. A fluorescent label, for example, may be used for detection of modified nucleotides. Each nucleotide type may thus carry a different fluorescent label, for example, as described in U.S. Provisional Application No. 60/801,270 (Novel dyes and the use of their labelled conjugates), published as WO07135368, the contents of which are incorporated herein by reference in their entirety. The detectable label need not, however, be a fluorescent label. Any label can be used which allows the detection of an incorporated nucleotide.

One method for detecting fluorescently labelled nucleotides comprises using laser light of a wavelength specific for the labelled nucleotides, or the use of other suitable sources of illumination. The fluorescence from the label on the nucleotide may be detected by a CCD camera or other suitable detection means. Suitable instrumentation for recording images of clustered arrays is described in U.S. Provisional Application No. 60/788,248 (Systems and devices for sequence by synthesis analysis), published as WO07123744, the contents of which are incorporated herein by reference in their entirety.

The invention is not intended to be limited to use of the sequencing method outlined above, as essentially any sequencing methodology which relies on successive incorporation of nucleotides into a polynucleotide chain can be used. Suitable alternative techniques include, for example, Pyrosequencing™, FISSEQ (fluorescent in situ sequencing), MPSS and sequencing by ligation-based methods, for example as described is U.S. Pat. No. 6,306,597.

The nucleic acid sample may be further analysed to obtain a second read from the opposite end of the fragment. Methodology for sequencing both ends of a cluster are described in co-pending applications WO07010252 and PCTGB2007/003798, the contents of which are incorporated by reference herein in their entirety. In one example, the series of steps may be performed as follows; generate clusters, linearise, hybridise first sequencing primer and obtain first sequencing read. The first sequencing primer can be removed, a second primer hybridised and the tag sequenced. The nucleic acid strand may then be 'inverted' on the surface by synthesising a complementary copy from the remaining immobilised primers used in cluster amplification. This process of strand resynthesis regenerates the double stranded cluster. The original template strand can be removed, to linearise the resynthesised strand that can then be annealed to a sequencing primer and sequenced in a third sequencing run.

In the cases where strand resynthesis is employed, both strands must be immobilised to the surface in a way that allows subsequent release of a portion of the immobilised strand. This can be achieved through a number of mechanisms as described in WO07010251, the contents of which are incorporated herein by reference in their entirety. For example, one primer can contain a uracil nucleotide, which means that the strand can be cleaved at the uracil base using the enzymes uracil glycosylase (UDG) which removes the nucleoside base, and endonuclease VIII that excises the abasic nucleotide. This enzyme combination is available as USER™ from New England Biolabs (NEB part number M5505). The second primer may comprise an 8-oxoguanine nucleotide, which is then cleavable by the enzyme FPG (NEB part number M0240). This design of primers provides complete control of which primer is cleaved at which point in the process, and also where in the cluster the cleavage occurs. The primers may also be chemically modified, for example with a disulfide or diol modification that allows chemical cleavage at specific locations.

Kits

The invention also relates to kits for use in preparing libraries of tagged polynucleotides using the method of the first, second or third aspects of the invention.

Embodiments of the kit comprise at least a supply of a mismatched adaptor as defined herein, plus a supply of at least one amplification primer which is capable of annealing to the mismatched adaptor and priming synthesis of an extension product, which extension product would include any target sequence ligated to the adaptor when the adaptor is in use.

Particular features of the 'mismatch' adaptors for inclusion in the kit are as described elsewhere herein in relation to other aspects of the invention. The structure and properties of amplification primers are well known to those skilled in the art. Suitable primers of appropriate nucleotide sequence for use with the adaptors included in the kit can be readily prepared using standard automated nucleic acid synthesis equipment and reagents in routine use in the art. The kit may include a supply of one single type of primer or separate supplies (or even a mixture) of two different primers, for example a pair of amplification primers suitable for PCR or isothermal amplification of templates modified with the mismatched adaptor in solution phase and/or on a suitable solid support (i.e. solid-phase amplification). The kit may comprise a mismatch double stranded adapter for ligation to a sample of interest, plus at least two different amplification primers that carry a different tag sequence, where the tag sequence does not hybridise to the adapter. This kit can be used to amplify at least two different samples where each sample is amplified using a single tagged primer, and then pooled after the individual amplification reactions.

In one embodiment the kit may include supplies of different primer-pairs for use in solution phase and solid phase PCR and more particularly isothermal amplification. In this context the 'different' primer-pairs may be of substantially identical nucleotide sequence but differ with respect to some other feature or modification, such as for example surface-capture moieties, etc. In other embodiments the kit may include a supply of primers for use in an initial primer extension reaction and a different primer-pair (or pairs) for solution and/or solid phase amplification.

Adaptors and/or primers may be supplied in the kits ready for use, or more preferably as concentrates requiring dilution before use, or even in a lyophilised or dried form requiring reconstitution prior to use. If required, the kits may further include a supply of a suitable diluent for dilution or reconstitution of the primers. Optionally, the kits may further comprise supplies of reagents, buffers, enzymes, dNTPs, etc., for use in carrying out PCR or isothermal amplification. Suitable (but non-limiting) examples of such reagents are as described in the Materials and Methods sections of the accompanying Examples. Further components which may optionally be supplied in the kit include 'universal' sequencing primers suitable for sequencing templates prepared using the mismatched adaptors and primers.

The invention will be further understood with reference to the following non-limiting experimental examples:

EXAMPLES

The following are examples of general techniques which may be applied in carrying out the method of the invention.

Example 1: Preparation and Conventional Sequencing of Tagged Libraries

The following experimental details describe the complete exposition of one embodiment of the invention as described above.

Two libraries were made, one using purified human BAC DNA (140 k human chromosome 6 insert cloned into a pTARBAC vector) and the other purified PhiX174 RF1 DNA (NEB, N3021L). Each library was prepared separately. The DNA was first prepared for ligation to forked adaptors by: fragmentation of the DNA by nebulisation, end repair of the DNA ends to render them blunt-ended and phosphorylated, then the addition of a single 'A' nucleotide onto the 3' ends of the DNA fragments. The ligation reaction was performed with the prepared fragmented DNA and adaptors pre-formed by annealing 'Oligo A' and 'Oligo B' (sequences given below). The same adaptors were used for each library. The product of the reaction was isolated/purified from unligated adaptor by gel electrophoresis. Finally, the product of the ligation reaction was subjected to cycles of PCR to selectively amplify ligated product that contained genomic DNA with adaptor at both ends of the fragments. During the PCR a unique tag was added to each library using a unique PCR primer, so that the BAC library was indexed with the unique sequence tag 'ATC' and the PhiX library was indexed with the unique sequence tag 'CGA'. See FIG. 1 for general schematic of protocol.

Materials and Methods
  Step 1) Nebulization
    Materials:
    0.5 ug/ul Human BAC DNA (140 k human chromosome 6 insert cloned into a pTARBAC vector)
    1 ug/ul PhiX174 RF1 DNA (NEB, N3021L)
    Nebulization Buffer (53.1 ml glycerol, 42.1 ml water, 3.7 ml 1 M Tris HCl pH7.5, 1.1 ml 0.5 M EDTA)
    TE
    Nebulizers (Invitrogen, K7025-05)
    PCR purification kit columns (Qiagen, 28104)
    Procedure:
    Mixed 5 µl (5 µg) of PhiX174 DNA with 45 µl of TE and 700 µl of nebulization buffer. Mixed 10 µl (5 µg) of BAC DNA with 40 µl of TE and 700 µl of nebulization buffer. Chilled DNA solutions were each fragmented in a nebulizer on ice for 6 minutes under 32 pounds per square inch (psi) of pressure. The recovered volumes were each purified with a Qiagen PCR purification kit column and eluted in 30 µl of EB.

Step 2) End-Repair
    Materials:
    Nebulized DNA (from Step 1)
    Water
    T4 DNA ligase buffer with 10 mM ATP (10×) (NEB, B0202S)
    dNTPs mix (10 mM each) (NEB, N0447S)
    T4 DNA Polymerase (3 U/ul) (NEB, M0203L)
    E. coli DNA Pol I large fragment (Klenow) (5 U/ul) (NEB, M0210S)
    T4 polynucleotide kinase (10 U/ul) (NEB, M0201L)
    PCR purification kit columns (Qiagen, 28104)
    Procedure:
    End repair mix was assembled as follows:

| | |
|---|---|
| Nebulized DNA | 30 µl |
| Water | 45 µl |
| T4 DNA ligase buffer with 10 mM ATP | 10 µl |
| dNTPs | 4 µl |
| T4 DNA pol | 5 µl |
| Klenow DNA pol | 1 ul |
| T4 PNK | 5 ul |
| | 100 µl total |

The reaction was incubated for 30 minutes at room temperature. The DNA was purified on a Qiagen column, eluting in 30 µl EB.

Step 3) A—Tailing Reaction
    Materials:
    End repaired DNA (from Step 2)
    Water
    NEB buffer 2 (10×) (NEB, B7002S)
    dATP (1 mM) (Amersham-Pharmacia, 272050)
    Klenow fragment (3' to 5' exo minus) (5 U/ul) (NEB, M0212B)
    Hot block or PCR machine
    MinElute PCR purification kit column (Qiagen, 28004)
    Procedure:
    The following reaction mix was assembled:

| | |
|---|---|
| End repaired DNA | 30 µl |
| Water | 2 ul |
| NEB buffer 2 | 5 µl |
| dATP | 10 µl |
| Klenow fragment (3' to 5' exo minus) | 3 µl |
| | 50 µl total |

The reaction was incubated for 30 minutes at 37° C., then the DNA purified on a Qiagen MinElute column, eluting in 10 µl EB.

Step 4) Annealed Adaptors
Materials:

Oligo A:
(SEQ ID NO. 1)
5'ACACTCTTTCCCTACACGACGCTCTTCCGATCxT (x = phosphorothioate bond)

Oligo B:
(SEQ ID NO. 2)
5'Phosphate-GATCGGAAGAGCGGTTCAGCAGGAATGCCGAG 50 mM Tris/50 mM NaCl pH7.0
PCR machine
Procedure:

The oligos were mixed together to a final concentration of 15 uM each, in 10 mM Tris/10 mM NaCl pH 7.0. The adaptor strands were annealed in a PCR machine programmed as follows: Ramp at 0.5° C./sec to 97.5° C.; Hold at 97.5° C. for 150 sec; then a step of 97.5° C. for 2 sec with a temperature drop of 0.1° C./cycle for 775 cycles.

In order to ensure that a sequencing primer is attached to both ends of the adapter for the paired end method, the sequence of oligonucleotide B was changed to:

(SEQ ID NO. 3)
5'Phosphate-GATCGGAAGAGCACACGTCT 3'

Step 5) Ligation
Materials:
A-tailed genomic DNA (from Step 3)
Quick ligase buffer (2×) (NEB, B2200S)
Annealed adaptor (15 uM) (from 4.)
Quick Ligase (1 U/up (NEB, M2200L)
PCR purification kit columns (Qiagen, 28104)
Procedure:
Reaction mix was assembled as follows:

| | |
|---|---|
| A-tailed genomic DNA | 10 µl |
| Quick ligase buffer | 25 µl |
| Annealed adaptor | 10 µl |
| Quick Ligase | 5 µl |
| | 50 µl total |

The reaction was incubated for 15 minutes at room temperature, then the DNA purified on a Qiagen column, eluting in 30 µl EB.

Step 6) Gel Purification
Materials:
Ligation reaction (from Step 5)
Agarose (Biorad, 161-3107)
TAE (50×)
Distilled water
Ethidium bromide (Sigma, E1510)
Loading buffer (4×) (50 mM Tris pH8, 40 mM EDTA, 40% w/v sucrose)
Low molecular weight ladder (NEB, N3233L)
Gel trays and tank. Electrophoresis unit
Dark reader transilluminator (Clare Chemical Research, D195M)
Gel extraction kit columns (Qiagen, 28704)
Procedure:

The entire sample from the purified ligation reaction was loaded into one lane of a 2% agarose gel containing ethidium bromide and run at 120V for 60 minutes. The gel was then viewed on a 'White-light' box and fragments from 120 bp to 170 bp excised and purified with a gel extraction column, eluting in 30 µl elution buffer (EB).

Step 7) Exonuclease I Treatment of PCR Primers
Materials:
Exonuclease I (E. coli) (20 U/ul) (NEB, M0293S)
Exonuclease I Reaction Buffer (10×) (NEB, M0293S)
Water
DNA Primers with a phosphorothioate at the n−1 position
P6 Bio-Rad columns (Bio-Rad, 732-6221)
Procedure:

DNA Primers with a phosphorothioate at the n−1 position (5×85 µl of each Primer (approx 25 µM)) were aliquoted into Eppendorf tubes. 10 µl of 10× Exonuclease I Reaction Buffer and 5 µl of Exonuclease I was added to each tube. Each Eppendorf tube was placed in a rack and stored in an oven set at 37° C. for 16 hours. After 16 hr, the tubes were placed on a hotblock set at 80° C. for 2 minutes. Subsequently, the solutions from the Eppendorfs were passed through P6 Bio-Rad columns and spun in a centrifuge at 2000 rpm for 2 minutes. An extra 20 µl of $H_2O$ was added to the columns and the columns respun. The filtered solutions were placed into a SpeedVac® and evaporated until each was at 20 µl, and the fractions combined. The pooled fractions were injected into a reverse phase HPLC system, and the main peak was collected. The collected fractions were evaporated to dryness in a SpeedVac®, 50 µl of water was added and the fraction was subjected again to evaporation to dryness. The resulting pellets were dissolved in 50 µl of water, pooled and a UV measurement taken to determine the concentration of the oligonucleotide.

Step 8) PCR
Materials:
Gel purified DNA (from Step 6)
Water
Phusion master mix (2×) (NEB, F-531L)
Exonuclease treated universal PCR primer (25 uM):

(SEQ ID NO. 4)
5' AATGATACGGCGACCACCGAGATCTACACTCTTTCCCTACACGACGC

TCTTCCGATCxT 3',
where x = phosphorothioate bond (from Step 7)

Exonuclease treated indexing PCR primer 1 (25 uM):

(SEQ ID NO. 5)
5' CAAGCAGAAGACGGCATACGAGATCGGTCTCGGCATTCCTGCTGAAC

CGCTCTTCCGATCxT,
where x = phosphorothioate bond (from Step 7)

Exonuclease treated indexing PCR primer 2 (25 uM):

(SEQ ID NO. 6)
5' CAAGCAGAAGACGGCATACGATCGCGGTCTCGGCATTCCTGCTGAA

CCGCTCTTCCGATCxT,
where x = phosphorothioate bond (from Step 7)

PCR machine
PCR purification kit columns (Qiagen, #28104)

Procedure:
The PCR reaction was prepared as follows:
BAC Library

| Gel purified BAC DNA | 1 μl |
|---|---|
| Phusion mastermix | 25 μl |
| Universal PCR primer | 1 μl |
| Indexing PCR primer 1 | 1 μl |
| Water | 22 μl |
| | 50 μl total |

PhiX174 Library

| Gel purified PhiX174 DNA | 1 μl |
|---|---|
| Phusion mastermix | 25 μl |
| Universal PCR primer | 1 μl |
| Indexing PCR primer 2 | 1 μl |
| Water | 22 μl |
| | 50 μl total |

Thermocycling was carried out in a PCR machine under the following conditions:
30 secs @ 98° C.
[10 sec@ 98° C., 30 sec @ 65° C., 30 sec @ 72° C.] 18 cycles
5 minutes @ 72° C.
Hold @ 4° C.

PCR products were purified on a Qiagen column, eluting in 30 μl EB. The resulting DNA libraries were ready for mixing and amplification on a surface amplification platform.

In the case of paired end runs, the human and Phi-X sample were split into 6 portions, and each portion was amplified with the two universal primers plus one of the 12 primers shown below.

```
Universal LPX primer
                                        (SEQ ID NO. 7)
5' GTGACTGGAGTTCAGACGTGTGCTCTTCCGATCxT 3'

Lpx primer
                                        (SEQ ID NO. 8)
5' AATGATACGGCGACCACCGAGATCTACACTCTTTCCCTACACGACG
CTCTTCCGATCxT Tag1 primer (CGTGAT)
                                        (SEQ ID NO. 9)
5' CAAGCAGAAGACGGCATACGAGATCGTGATGTGACTGGAGTTC 3'

Tag2 primer (ACATCG)
                                        (SEQ ID NO. 10)
5' CAAGCAGAAGACGGCATACGAGATACATCGGTGACTGGAGTTC 3'

Tag3 primer (GCCTAA)
                                        (SEQ ID NO. 11)
5' CAAGCAGAAGACGGCATACGAGATGCCTAAGTGACTGGAGTTC 3'

Tag4 primer (TGGTCA)
                                        (SEQ ID NO. 12)
5' CAAGCAGAAGACGGCATACGAGATTGGTCAGTGACTGGAGTTC 3'

Tag5 primer (CACTGT)
                                        (SEQ ID NO. 13)
5' CAAGCAGAAGACGGCATACGAGATCACTGTGTGACTGGAGTTC 3'

Tag6 primer (ATTGGC)
                                        (SEQ ID NO. 14)
5' CAAGCAGAAGACGGCATACGAGATATTGGCGTGACTGGAGTTC 3'

Tag7 primer (GATCTG)
                                        (SEQ ID NO. 15)
5' CAAGCAGAAGACGGCATACGAGATGATCTGGTGACTGGAGTTC 3'

Tag8 primer (TCAAGT)
                                        (SEQ ID NO. 16)
5' CAAGCAGAAGACGGCATACGAGATTCAAGTGTGACTGGAGTTC 3'

Tag9 primer (CTGATC)
                                        (SEQ ID NO. 17)
5' CAAGCAGAAGACGGCATACGAGATCTGATCGTGACTGGAGTTC 3'

Tag10 primer (AAGCTA)
                                        (SEQ ID NO. 18)
5' CAAGCAGAAGACGGCATACGAGATAAGCTAGTGACTGGAGTTC 3'

Tag11 primer (GTAGCC)
                                        (SEQ ID NO. 19)
5' CAAGCAGAAGACGGCATACGAGATGTAGCCGTGACTGGAGTTC 3'

Tag12 primer (TACAAG)
                                        (SEQ ID NO. 20)
5' CAAGCAGAAGACGGCATACGAGATTACAAGGTGACTGGAGTTC 3'
```

The two universal primers contain a phosphorothioate group (x) and were exonucleases treated and purified prior to amplification. The amplification conditions were as described above, and the 6 tagged human samples, and 6 tagged Phi-X sample were pooled together for sequencing on clusters.

Validation of Libraries by Conventional Sanger Sequencing

Four (4) μl of the libraries were cloned into a plasmid vector (Zero Blunt TOPO PCR cloning kit, Invitrogen #K2800-20) and plated out on agar, according to the manufacturer's instructions. Colonies were picked, mini-prepped and the cloned fragments sequenced by conventional Sanger sequencing.

16 Clones from BAC Library (ATC Tag)

```
1 (204bp) Insert: E. coli 85bp
                                        (SEQ ID NO. 21)
AATGATACGGCGACCACCGAGATCTACACTCTTTCCCTACACGACGCTCT

TCCGATCTACTGATTTCATTGCAGCCAAAGGCAAACTTTGGCTGCATCGT

TTTACAGTCGCCATAAGCCTTTCCTCTGTTAAACCGCCTTCTGAGATCGG

AAGAGCGGTTCAGCAGGAATGCCGAGACCGATCTCGTATGCCGTCTTCTG

CTTG 2 (214bp) Insert: BAC 95bp
                                        (SEQ ID NO. 22)
AATGATACGGCGACCACCGAGATCTACACTCTTTCCCTACACGACGCTCT

TCCGATCTATCAATATTGTGAAAATGACCATACTGCCAAAAAAAAACTAC

AAATTCAATGCAATTTTCATCAAAATACCATCATCATTCTTCACAATATT

GATAGATCGGAAGAGCGGTTCAGCAGGAATGCCGAGACCGATCTCGTATG

CCGTCTTCTGCTTG 3 (215bp) Insert: BAC 96bp
                                        (SEQ ID NO. 23)
AATGATACGGCGACCACCGAGATCTACACTCTTTCCCTACACGACGCTCT

TCCGATCTCTCACTCCTGGCAGAGGGACGTGTGACTAGCCATGGGCCCCT

AGGTCTCCAGTTCCTGGGTAGCTTGTATTTTTGAACATCTCCTGTATATT

AGTTAGATCGGAAGAGCGGTTCAGCAGGAATGCCGAGACCGATCTCGT

ATGCCGTCTTCTGCTTG
```

4 (147bp) Insert: BAC 28bp
(SEQ ID NO. 24)
AATGATACGGCGACCACCGAGATCTACACTCTTTCCCTACACGACGCTCT

TCCGATCTAGTGTAGTTGAGATCTGCCTTAGCAGCAAGATCGGAAGAGCG

GTTCAGCAGGAATGCCGAGACCGATCTCGTATGCCGTCTTCTGCTTG 5 (183bp) Insert: BAC 64bp
(SEQ ID NO. 25)
AATGATACGGCGACCACCGAGATCTACACTCTTTCCCTACACGACGCTCT

TCCGATCTAACACATTTCAAAGTTTGGGGCCCTCCTCCTCCCCAAAAAAC

AAACCACAAAAAACAAACAAAAAGATCGGAAGAGCGGTTCAGCAGGAATG

CCGAGACCGATCTCGTATGCCGTCTTCTGCTTG 6 (170bp) Insert: BAC 59bp
(SEQ ID NO. 26)
GGCGACCACCGAGATCTACACTCTTTCCCTACACGACGCTCTTCCGATCT

GAATGCCTTTTATAGCATTTAATTITTCCTAAGTATAATTACCAAATAAA

AATTGTATAAGATCGGAAGAGCGGTTCAGCAGGAATGCCGAGACCGATCT

CGTATGCCGTCTTCTGCTTG 7 (180bp) Insert: BAC 61bp
(SEQ ID NO. 27)
AATGATACGGCGACCACCGAGATCTACACTCTTTCCCTACACGACGCTCT

TCCGATCTTGGGCCCGGGAGGAGTTTGCCGGGGAGGAGTGGGTTTGGAAT

CGGGGTTAAAGGAAGAGAAGATCGGAAGAGCGGTTCAGCAGGAATGCCG

AGACCGATCTCGTATGCCGTCTTCTGCTTG 8 (190bp) Insert: BAC 73bp
(SEQ ID NO: 28)
TGATACGGCGACCACCGAGATCTACACTCTTTCCCTACACGACGCTCTTC

CGATCTAAGATCTATTTCAAATGGACTGTAGATCTAAGTATAAAAGGTAA

GAGAATAATTATTCTAGAAAGTAAATGTAAGATCGGAAGAGCGGTTCAGC

AGGAATGCCGAGACCGATCTCGTATGCCGTCTTCTGCTTG 9 (192bp) Insert: BAC 74bp
(SEQ ID NO. 29)
AATGATACGGCGACCACCGAGATCTACACTCTTTCCCTACACGACGCTCTT

CCGATCTGGGAGGCCAAGGTGGGTGGATCACCTGAGATCAGGAGTTCGAG

ACCAGCTGGCCAACATGATGAAACTCTGTCTAGATCGGAAGAGCGGTTCA

GCAGGAATGCCGAGACCGATCTCGTATGCCGTCTTCTGCTTG 10 (185bp) Insert: BAC 66bp
(SEQ ID NO. 30)
AATGATACGGCGACCACCGAGATCTACACTCTTTCCCTACACGACGCTCT

TCCGATCTTGACCATTGTAACCATTAATGTAGACTGCAATGATATGCACT

ATTTACAACCTTTTTTAAGACTCTAGATCGGAAGAGCGGTTCAGCAGGAA

TGCCGAGACCGATCTCGTATGCCGTCTTCTGCTTG 11 (199bp) Insert: BAC 80bp
(SEQ ID NO. 31)
AATGATACGGCGACCACCGAGATCTACACTCTTTCCCTACACGACGCTCT

TCCGATCTCTTTGAAGAGCTGGCAGTAGAAGATAAACAGGCTGGGGAAGA

AGAGAAAGTGCTCAAGGAGAAGGAGCAGCAGCAGCAGCAGATCGGAAGAG

CGGTTCAGCAGGAATGCCGAGACCGATCTCGTATGCCGTCTTCTGCTTG 12 (212bp) Insert: BAC 93bp
(SEQ ID NO. 32)
AATGATACGGCGACCACCGAGATCTACACTCTTTCCCTACACGACGCTCT

TCCGATCTAGTATTCAACAAGTCTGTCTTTTCCAAGTGTCTTTAAAGACC

AGAAATACCTGTTTTTAACACACAGGGTTGCAAAATTCAGAGGAGATTGG

CAGATCGGAAGAGCGGTTCAGCAGGAAtGCCGAGACCGATCTCGTATGCC

GTCTTCTGCTTG 13 (247bp) Insert: E. coli 128bp
(SEQ ID NO. 33)
AATGATACGGCGACCACCGAGATCTACACTCTTTCCCTACACGACGCTCT

TCCGATCTCTTGAGATGAGTGATGACGGCGCGCTGGAAGTTGCTCGTCGC

GCTCGCGGTACGCCGCGCATTGCCAACCGTCTGCTGCGTCGAGTGCGTGA

TTTCGCCGAAGTGAAGCACGATGGCACCATCTCAAGAGATCGGAAGAGCG

GTTCAGCAGGAATGCCGAGACCGATCTCGTATGCCGTCTTCTGCTTG 14 (202bp) Insert: BAC 83bp
(SEQ ID NO. 34)
AATGATACGGCGACCACCGAGATCTACACTCTTTCCCTACACGACGCTCT

TCCGATCTGGGGTTGGTGGAACCCAGATGCCTCCCAGGATTGGTGGGCCC

TGTGGCACTTGTACCTGCTGTTGCTGTTGCTGCTGCTGAGATCGGAA

GAGCGGTTCAGCAGGAATGCCGAGACCGATCTCGTATGCCGTCTTCTGCT

TG 15 (166bp) Insert: BAC 47bp
(SEQ ID NO. 35)
AATGATACGGCGACCACCGAGATCTACACTCTTTCCCTACACGACGCTCT

TCCGATCTATGATAAGGAGCAGGTTTACAGATCATAAGTGCAAAAGCGGG

CGAGAAGATCGGAAGAGCGGTTCAGCAGGAATGCCGAGACCGATCTCGTA

TGCCGTCTTCTGCTTG 16 (147bp) Insert: BAC 31bp
(SEQ ID NO. 36)
GATACGGCGACCACCGAGATCTACACTCTTTCCCTACACGACGCTCTTCC

GATCTCTGATACTGTTGTAACCACCCAATTGGTTCAAGATCGGAAGAGCG

GTTCAGCAGGAATGCCGAGACCGATCTCGTATGCCGTCTTCTGCTTG

16 Clones from PhiX174 Library (CGA Tag)

1 (183bp) Insert: PhiX 67bp
(SEQ ID NO. 37)
AATGATACGACCACCGAGATCTACACTCTTTCCCTACACGACGCTCTTCC

GATCTTAAAGCTACCAGTTATATGGCTGTTGGTTTCTATGTGGCTAAATA

CGTTAACAAAAAGTCAGATATGAGATCGGAAGAGCGGTTCAGCAGGAATG

CCGAGACCGCGATCGTATGCCGTCTTCTGCTTG 2 (174bp) Insert: PhiX 58bp
(SEQ ID NO. 38)
GATACGGCGACCACCGAGATCTACACTCTTTCCCTACACGACGCTCTTCC

GATCTCGACCACTCGCGATTCAATCATGACTTCGTGATAAAAGATTGAGT

GTGAGGTTATAACAGATCGGAAGAGCGGTTCAGCAGGAATGCCGAGACCG

CGATCGTATGCCGTCTTCTGCTTG 3 (179bp) Insert: PhiX 62bp
(SEQ ID NO. 39)
TGATACGGCGACCACCGAGATCTACACTCTTTCCCTACACGACGCTCTTC

CGATCTTCTATGAAGGATGTTTTCCGTTCTGGTGATTCGTCTAAGAAGTT

TAAGATTGCTGAGGGTCAAGATCGGAAGAGCGGTTCAGCAGGAATGCCGA

GACCGCGATCGTATGCCGTCTTCTGCTTG 4 (169bp) Insert: PhiX 50bp
(SEQ ID NO. 40)
AATGATACGGCGACCACCGAGATCTACACTCTTTCCCTACACGACGCTCT

TCCGATCTGGTTGCGCCGCCAAAACGTCGGCTACAGTAACTTTTCCCAGC

CTCAATCTAGATCGGAAGAGCGGTTCAGCAGGAATGCCGAGACCGCGATC

GTATGCCGTCTTCTGCTTG 5 (166bp) Insert: PhiX 50bp
(SEQ ID NO. 41)
TGATACGGCGACCACCGAGATCTACATCTTTCCCTACACGACGCTCTTCC

GATCTAACAACTGAACGGACTGGAAACACTGGTCATAATCATGGTGGCGA

ATAAGAGATCGGAAGAGCGGTTCAGCAGGAATGCCGAGACCGCGATCGTA

TGCCGTCTTCTGCTTG 6 (164bp) Insert: PhiX 45bp
(SEQ ID NO. 42)
AATGATACGGCGACCACCGAGATCTACACTCTTTCCCTACACGACGCTCT

TCCGATCTAAATACGTTAACAAAAAGTCAGATATGGACCTTGCTGCTAAA

GGTAGATCGGAAGAGCGGTTCAGCAGGAATGCCGAGACCGCGATCGTATG

CCGTCTTCTGCTTG 7 (194bp) Insert: PhiX 75bp
(SEQ ID NO. 43)
AATGATACGGCGACCACCGAGATCTACACTCTTTCCCTACACGACGCTCT

TCCGATCTGTCAATATAACCAGTAGTGTTAACAGTCGGGAGAGGAGTGGC

ATTAACACCATCCTTCATGAACTTAATCCACTGAGATCGGAAGAGCGGTT

CAGCAGGAATGCCGAGACCGCGATCGTATGCCGTCTTCTGCTTG 8 (198bp) Insert: PhiX 79bp
(SEQ ID NO. 44)
AATGATACGGCGACCACCGAGATCTACACTCTTTCCCTACACGACGCTCT

TCCGATCTGATAGTTTGACGGTTAATGCTGGTAATGGTGGITTTCTTCAT

TGCATTCAGATGGATACATCTGTCAACGCCGCTAATCAGATCGGAAGAGC

GGTTCAGCAGGAATGCCGAGACCGCGATCGTATGCCGTCTTCTGCTTG 9 (179bp) Insert: PhiX 60bp
(SEQ ID NO. 45)
AATGATACGGCGACCACCGAGATCTACACTCTTTCCCTACACGACGCTCT

TCCGATCTTGAAACCAACATAAACATTATTGCCCGGCGTACGAGGAAGGA

CGTCAATAGTCACACAGTAGATCGGAAGAGCGGITCAGCAGGAATGCCGA

GACCGCGATCGTATGCCGTCTTCTGCTTG 10 (198bp) Insert: PhiX 79bp
(SEQ ID NO. 46)
AATGATACGGCGACCACCGAGATCTACACTCTTTCCCTACACGACGCTCT

TCCGATCTCCAGCTTCTTCGGCACCTGTTTTACAGACACCTAAAGCTACA

TCGTCAACGTTATATTTTGATAGTTTGACGGTTAATAAGATCGGAAGAGC

GGTTCAGCAGGAATGCCGAGACCGCGATCGTATGCCGTCTTCTGCTTG 11 (151bp) Insert: PhiX 32bp
(SEQ ID NO. 47)
AATGATACGGCGACCACCGAGATCTACACTCTTTCCCTACACGACGCTCT

TCCGATCTCAGTTTTGCCGCAAGCTGGCTGCTGAACGCCCAGATCGGAAG

AGCGGTTCAGCAGGAATGCCGAGACCGCGATCGTATGCCGTCTTCTGCTT

G 12 (173bp) Insert: PhiX 54bp
(SEQ ID NO. 48)
AATGATACGGCGACCACCGAGATCTACACTCTTTCCCTACACGACGCTCT

TCCGATCTTTTGCTGATGAACTAAGTCAACCTCAGCACTAACCTTGCGAG

TCATTTCTTTGAAGATCGGAAGAGCGGTTCAGCAGGAATGCCGAGACCGC

GATCGTATGCCGTCTTCTGCTTG 13 (151bp) Insert: PhiX 32bp
(SEQ ID NO. 49)
AATGATACGGCGACCACCGAGATCTACACTCTTTCCCTACACGACGCTCT

TCCGATCTAATAGACGCAACGCGAGCAGTAGACTCCTTCTAGATCGGAAG

AGCGGTTCAGCAGGAATGCCGAGACCGCGATCGTATGCCGTCTTCTGCTT

G 14 (168bp) Insert: PhiX 49bp
(SEQ ID NO. 50)
AATGATACGGCGACCACCGAGATCTACACTCTTTCCCTACACGACGCTCT

TCCGATCTGGAGGCCTCCAGCAATCTTGAACACTCATCCTTAATACCTTT

CTTTTTGAGATCGGAAGAGCGGTTCAGCAGGAATGCCGAGACCGCGATCG

TATGCCGTCTTCTGCTTG 15 (181bp) Insert: PhiX 62bp
(SEQ ID NO. 51)
AATGATACGGCGACCACCGAGATCTACACTCTTTCCCTACACGACGCTCT

TCCGATCTACTCCTAAGCAGAAAACCTACCGCGCTTCGCTTGGTCAACCC

CTCAGCGGCAAAAATTAAAAAGATCGGAAGAGCGGTTCAGCAGGAATGCC

GAGACCGCGATCGTATGCCGTCTTCTGCTTG 16 (182bp) Insert: E. coli 63bp
(SEQ ID NO. 52)
AATGATACGGCGACCACCGAGATCTACACTCTTTCCCTACACGACGCTCT

TCCGATCTGAGCCGACATCGAGGTGCCAAACACCGCCGTCGATATGAACT

CTTGGGCGGTATCAGCCTGTTAGATCGGAAGAGCGGTTCAGCAGGAATGC

CGAGACCGCGATCGTATGCCGTCTTCTGCTTG

These results confirm that the library preparation method produces 2 libraries of 'sequenceable' DNA templates. Each library contained a plurality of genomic inserts, each of which was flanked by the two adaptors (AATGATACGGC-GACCACCGAGATCTACACTCTTTCCCTACAC-GACGCTCTTCCGATCT and AGATCGGAAGAGCGGT-TCAGCAGGAATGCCGAGACCGNNNTCGTATGCC-GTCTTCTGCTT G) (SEQ ID NO. 54), required for cluster formation and SBS sequencing. The insert DNA from each of the libraries aligned to the correct reference, either BAC or PhiX, with a small amount of E. coli contamination in each library. The correct TAG (CGA for PhiX or ATC for BAC) was present in each library.

Example of Cluster Preparation Using the Mixed PHiX and BAC Libraries

Example 2): Acrylamide Coating of Glass Chips

The solid supports used are typically 8-channel glass chips such as those provided by Silex Microsystems (Sweden). However, the experimental conditions and procedures are readily applicable to other solid supports.

Chips were washed as follows: neat Decon for 30 minutes, milliQ $H_2O$ for 30 minutes, NaOH 1N for 15 minutes, milliQ $H_2O$ for 30 minutes, HCl 0.1N for 15 minutes, milliQ $H_2O$ for 30 minutes.

Polymer Solution Preparation:
For 10 ml of 2% polymerisation mix.
- 10 ml of 2% solution of acrylamide in milliQ $H_2O$
- 165 µl of a 100 mg/ml N-(5-bromoacetamidylpentyl) acrylamide (BRAPA) solution in DMF (23.5 mg in 235 µl DMF)
- 11.5 µl of TEMED
- 100 µl of a 50 mg/ml solution of potassium persulfate in milliQ $H_2O$ (20 mg in 400 µl $H_2O$)

The 10 ml solution of acrylamide was first degassed with argon for 15 minutes. The solutions of BRAPA, TEMED and potassium persulfate were successively added to the acrylamide solution. The mixture was then quickly vortexed and immediately used. Polymerization was then carried out for 1 h 30 minutes at RT. Afterwards the channels were washed with milliQ $H_2O$ for 30 minutes and filled with 0.1 M potassium phosphate buffer for storage until required.

Example 3) Synthesis of
N-(5-Bromoacetamidylpentyl) Acrylamide
(BRAPA) (1)

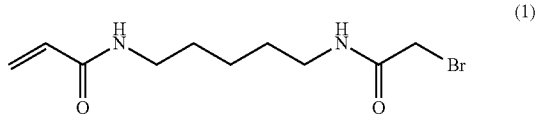

(1)

N-Boc-1,5-diaminopentane toluene sulfonic acid was obtained from Novabiochem. The bromoacetyl chloride and acryloyl chloride were obtained from Fluka. All other reagents were Aldrich products.

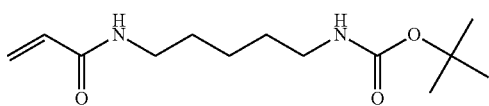

(2)

To a stirred suspension of N-Boc-1,5-diaminopentane toluene sulfonic acid (5.2 g, 13.88 mmol) and triethylamine (4.83 ml, 2.5 eq) in THF (120 ml) at 0° C. was added acryloyl chloride (1.13 ml, 1 eq) through a pressure equalized dropping funnel over a one hour period. The reaction mixture was then stirred at room temperature and the progress of the reaction checked by TLC (petroleum ether: ethyl acetate 1:1). After two hours, the salts formed during the reaction were filtered off and the filtrate evaporated to dryness. The residue was purified by flash chromatography (neat petroleum ether followed by a gradient of ethyl acetate up to 60%) to yield 2.56 g (9.98 mmol, 71%) of product 2 as a beige solid. $^1$H NMR (400 MHz, $d_6$-DMSO): 1.20-1.22 (m, 2H, $CH_2$), 1.29-1.43 (m, 13H, tBu, 2×$CH_2$), 2.86 (q, 2H, J=6.8 Hz and 12.9 Hz, $CH_2$), 3.07 (q, 2H, J=6.8 Hz and 12.9 Hz, $CH_2$), 5.53 (dd, 1H, J=2.3 Hz and 10.1 Hz, CH), 6.05 (dd, 1H, J=2.3 Hz and 17.2 Hz, CH), 6.20 (dd, 1H, J=10.1 Hz and 17.2 Hz, CH), 6.77 (t, 1H, J=5.3 Hz, NH), 8.04 (bs, 1H, NH). Mass (electrospray+) calculated for $C_{13}H_{24}N_2O_3$ 256, found 279 (256+$Na^+$).

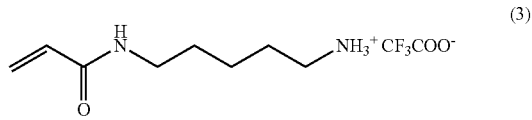

(3)

Product 2 (2.56 g, 10 mmol) was dissolved in trifluoroacetic acid:dichloromethane (1:9, 100 ml) and stirred at room temperature. The progress of the reaction was monitored by TLC (dichloromethane:methanol 9:1). On completion, the reaction mixture was evaporated to dryness, the residue co-evaporated three times with toluene and then purified by flash chromatography (neat dichloromethane followed by a gradient of methanol up to 20%). Product 3 was obtained as a white powder (2.43 g, 9 mmol, 90%). $^1$H NMR (400 MHz, $D_2O$): 1.29-1.40 (m, 2H, $CH_2$), 1.52 (quint., 2H, J=7.1 Hz, $CH_2$), 1.61 (quint., 2H, J=7.7 Hz, $CH_2$), 2.92 (t, 2H, J=7.6 Hz, $CH_2$), 3.21 (t, 2H, J=6.8 Hz, $CH_2$), 5.68 (dd, 1H, J=1.5 Hz and 10.1 Hz, CH), 6.10 (dd, 1H, J=1.5 Hz and 17.2 Hz, CH), 6.20 (dd, 1H, J=10.1 Hz and 17.2 Hz, CH). Mass (electrospray+) calculated for $C_8H_{16}N_2O$ 156, found 179 (156+$Na^+$).

To a suspension of product 3 (6.12 g, 22.64 mmol) and triethylamine (6.94 ml, 2.2 eq) in THF (120 ml) was added bromoacetyl chloride (2.07 ml, 1.1 eq), through a pressure equalized dropping funnel, over a one hour period and at −60° C. (cardice and isopropanol bath in a Dewar). The reaction mixture was then stirred at room temperature overnight and the completion of the reaction was checked by TLC (dichloromethane:methanol 9:1) the following day. The salts formed during the reaction were filtered off and the reaction mixture evaporated to dryness. The residue was purified by chromatography (neat dichloromethane followed by a gradient of methanol up to 5%). 3.2 g (11.55 mmol, 51%) of the product 1 (BRAPA) were obtained as a white powder. A further recrystallization performed in petroleum ether:ethyl acetate gave 3 g of the product 1. $^1$H NMR (400 MHz, $d_6$-DMSO): 1.21-1.30 (m, 2H, $CH_2$), 1.34-1.48 (m, 4H, 2×$CH_2$), 3.02-3.12 (m, 4H, 2×$CH_2$), 3.81 (s, 2H, $CH_2$), 5.56 (d, 1H, J=9.85 Hz, CH), 6.07 (d, 1H, J=16.9 Hz, CH), 6.20 (dd, 1H, J=10.1 Hz and 16.9 Hz, CH), 8.07 (bs, 1H, NH), 8.27 (bs, 1H, NH). Mass (electrospray+) calculated for $C_{10}H_{17}BrN_2O_2$ 276 or 278, found 279 (278+$H^+$), 299 (276+$Na^+$).

Example 4) Grafting Primers onto Surface of SFA Coated Chip

An SFA coated chip is placed onto a modified MJ-Research thermocycler and attached to a peristaltic pump. Grafting mix consisting of 0.5 µM of a forward primer and 0.5 µM of a reverse primer in 10 mM phosphate buffer (pH 7.0) is pumped into the channels of the chip at a flow rate of 60 µl/minutes for 75 s at 20° C. The thermocycler is then heated to 51.6° C., and the chip is incubated at this temperature for 1 hour. During this time, the grafting mix undergoes 18 cycles of pumping: grafting mix is pumped in at 15 µl/minutes for 20 s, then the solution is pumped back and forth (5 s forward at 15 µl/minutes, then 5 s backward at 15 µl/minutes) for 180 s. After 18 cycles of pumping, the chip is washed by pumping in 5×SSC/5 mM EDTA at 15 µl/minutes for 300 s at 51.6° C. The thermocycler is then cooled to 20° C.

The primers are typically 5'-phosphorothioate oligonucleotides incorporating any specific sequences or modifications required for cleavage. Their sequences and suppliers vary according to the experiment for which they are to be used, and in this case were complementary to the 5'-ends of the template duplex. The DNA sequence used in this process was the pool of the two libraries, which have ends complementary to the grafted primers. The library mix was denatured using sodium hydroxide treatment followed by snap dilution as described.

For some of the experiments detailed, the amplified clusters contained a diol linkage in one of the grafted primers. Diol linkages can be introduced by including a suitable linkage into one of the primers used for solid-phase amplification. Synthesis of the diol phosphoramidite is described in Example 4 below. Products containing such diol linkages can be cleaved using periodate and propanolamine as described, and the resulting single stranded polynucleotides hybridised as described.

The grafted primers contain a sequence of T bases at the 5'-end to act as a spacer group to aid linearisation and hybridization. The sequences of the two primers grafted to the chip are as follows:

```
P5diol:
                                          (SEQ ID NO. 55)
5' PS-TTTTTTTTTT-diol-AATGATACGGCGACCACCGA P7:
                                          (SEQ ID NO. 56)
5' PS-TTTTTTTTTTCAAGCAGAAGACGGCATACGA
```

Example 5: Preparation of Diol-Phosphoramidite for DNA Coupling

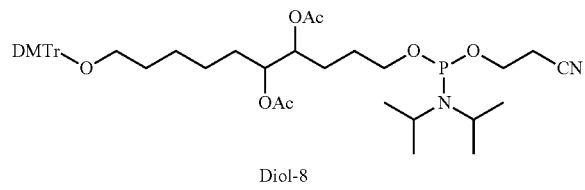

Diol-8

Step 1:

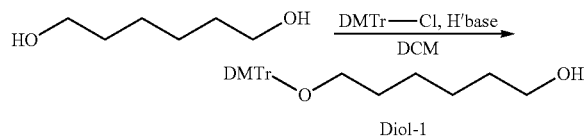

Diol-1

1,6-Hexanediol (Sigma Aldrich 99%) (14.6 g, 124 mmol), N,N-diisopropylethylamine (Hünig's base; Sigma Aldrich; redistilled) (21.6 mL, 124 mmol) is dissolved in anhydrous DCM/DMF (250/50 mL) under $N_2$. The solution is cooled to 0° C. and the first portion of 4,4'-dimethoxytrityl chloride (DMTr-Cl; Sigma-Aldrich 95%) (10.5 g, 31 mmol) is added. The reaction mixture is then warmed to room temperature. After stirring for 1 h, the reaction mixture is cooled to 0° C. again and the second portion of DMTr-Cl (10.5 g, 31 mmol) is added and then allowed to stir at room temperature for another 2 hours. TLC (EtOAc: petroleum ether 4:6) analysis indicates ca. 95% consumption of starting material derivative (DMTr-OH). The reaction is concentrated under reduced pressure and Aq. $NaHCO_3$ (sat.) solution (500 mL) is poured into the residue. The resulting mixture is extracted with petroleum ether/EtOAc (2:1) (3×1000 mL). The combined organic layers are dried over $MgSO_4$, and concentrated under vacuum. The residue is co-evaporated with xylene (2×100 mL) to remove DMF. The reaction mixture, is pre-absorbed on silica gel and subjected to flash chromatography using solvents containing 1% $Et_3N$ petroleum ether to petroleum ether/EtOAc (7:3) as eluent. The yield of pale yellow oil is 16.58 g, 64%, with a further 7.8 g (17%) of the bis-tritylated by-product.

TLC: $R_f$: 0.35 (diol-1); $R_f$: 0.7 (bis-tritylated by-product) (petroleum ether/EtOAc 6:4).

$^1$H NMR (400 MHz, $CDCl_3$): δ 1.32-1.44 (m, 4H, 2×$CH_2$), 1.54-1.68 (m, 4H, 2×$CH_2$), 3.06 (t, J=6.6 Hz, 2H, $CH_2O$), 3.62-3.68 (m, 2H, $CH_2OH$), 3.81 (s, 6H, 2×MeO), 6.83-6.85 (m, 4H, Ph), 7.24-7.35 (m, 7H, Ph), 7.45-7.47 (m, 2H, Ph).

Step 2:

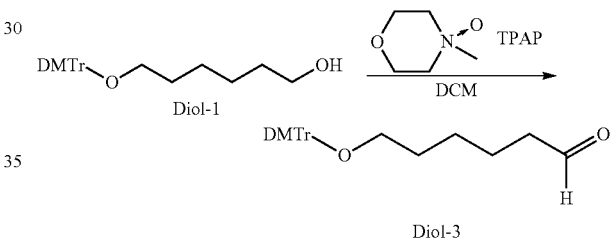

Diol-3

To a solution of Diol-1 (16.6 g, 39.5 mmol) in anhydrous DCM (200 mL), tetrapropylammonium perruthenate (TPAP; Sigma Aldrich 97%) (277 mg, 0.79 mmol) is added under $N_2$ atmosphere. The solution is cooled to 0° C. and N-methylmopholine N-oxide (Sigma Aldrich 97%) (2.7 g, 23 mmol) is added. The reaction is warmed to room temperature. After 1 hour, the other three portions of N-methylmopholine N-oxide (3×2.0 g, 51.2 mmol) are added within a period of four hours. TLC (EtOAc: petroleum ether 4:6) indicates the reaction goes to completion. The reaction is quenched with aq. $NaHCO_3$ (sat.) (1000 mL) and extracted to $CH_2Cl_2$ (4×1000 mL). The combined organic layers are dried over $MgSO_4$. The solution is concentrated under reduced pressure. Diol-3, 9.9 g, 60%, is isolated by flash chromatography using solvents containing 1% $Et_3N$ from petroleum ether to petroleum ether/EtOAc (6:4) as eluent, as a pale yellow oil.

TLC: $R_f$: 0.7 (petroleum ether/EtOAc 6:4).

$^1$H NMR (400 MHz, $CDCl_3$): δ 1.30-1.37 (m, 2H, $CH_2$), 1.48-1.57 (m, 4H, 2×$CH_2$), 2.34 (td, J=1.7 and 7.4 Hz, 2H, $CH_2CHO$), 2.97 (s, 2H, $CH_2O$), 3.72 (s, 6H, 2×MeO), 6.73-6.76 (m, 4H, Ph), 7.10-7.26 (m, 7H, Ph), 7.34-7.36 (m, 2H, Ph), 9.67 (t, J=1.7, 1H, CHO).

Step 3:

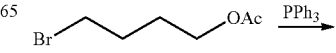

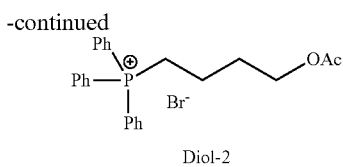

Diol-2

A solution of triphenylphosphine (Sigma-Aldrich 99%, ReagentPlus™). (39.3 g, 150 mmol) and 4-bromobutyl acetate (Sigma-Aldrich)(26 mL, 180 mmol) in anhydrous toluene (300 mL) is heated under reflux for 36 hours under $N_2$ in an oil-bath (140° C.). During the reflux, oil is precipitated out. The reaction mixture is cooled to room temperature. TLC (petroleum ether/EtOAc 7:3) analysis of the toluene solution showed that there is still triphenylphosphine ($R_f$; 0.8) left. The supernatant is decanted into another round-bottomed flask and concentrated down to the approximate volume of 30 mL. The solution is heated under reflux again for another 12 hours. The supernatant is decanted. The portions of oil are combined together, dissolved in water (500 mL) and extracted with EtOAc (2×500 mL). The combined organic layers are back-extracted with water (150 mL). Two lots of aqueous layers are combined, and evaporated under reduced pressure. The resulting residue is co-evaporated with acetonitrile (2×100 mL) to give 78.4 g, 95% yield of a pale yellow oil. NMR indicates that the product is pure, and is used for the next step reaction without further purification.

TLC: $R_f$; 0.0 (petroleum ether/EtOAc 7:3).

$^1$H NMR (400 MHz, $CDCl_2$): δ 1.63-1.73 (m, 2H, $CH_2$), 1.94 (s, 3H, 2×$CH_2$), 2.06-2.16 (m, 2H, $CH_2$), 3.97-4.05 (m, 2H, $CH_2$P), 4.11 (t, J=6.0, 2H, $CH_2$O), 7.69-7.95 (m, 15H, Ph).

$^{31}$P NMR (162 MHz, $CDCl_3$): 25.9 ppm.

Mass spec details: LC-MS (Electrospray positive): ($M^+$) 377.

Step 4:

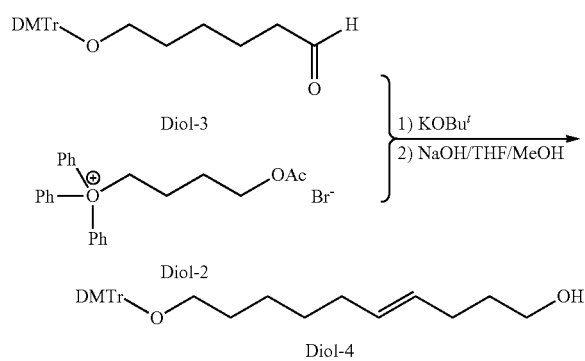

Diol-2 (10.34 g, 22.7 mmol) is weighed into a round-bottomed flask and dissolved with DCM (20 mL). The solution is then evaporated under reduced pressure until it gives a white foam. The flask is then subjected to high vacuum for 24 h. To this flask, anhydrous THF (180 mL) is added under $N_2$. The resulting suspension is cooled to −78° C. with an acetone-dry ice bath. With vigorous stirring, KOBu$^t$ (3.3 g, 29.5 mmol) is added under $N_2$. Slowly the colour of the suspension turns orange, and white solids are gradually precipitated out. To this suspension, a solution of diol-3 (dried at 60° C. under high vacuum for 1 h before the reaction), (9.5 g, 22.7 mmol) in THF (50 mL) is added drop wise over half an hour. Acetone-dry ice bath is then removed. The reaction mixture is slowly warmed to room temperature and stirred for another hour. The colour of the reaction mixture turns yellow after the addition of diol-3. The reaction mixture is concentrated down under reduced pressure. The resulting residue is partitioned between DCM (800 mL) and aq. NaCl (sat.) (800 mL). The aqueous layer is extracted with an additional DCM (2×800 mL). The organic extractions are combined, dried over $MgSO_4$, filtered, and evaporated under reduced pressure to give yellow oil. The oil is dissolved in THF/MeOH (125/100 mL) and cooled to 0° C. To this solution, NaOH (1M in $H_2O$, 25 mL) is added. After allowing the reaction to stir for 1 hour, TLC analysis indicates full consumption of starting material. The reaction mixture is neutralized with acetic acid (1.5 mL). The reaction mixture is concentrated down under reduced pressure. The resulting residue is partitioned between DCM (800 mL) and aq. $NaHCO_3$ (sat.) (800 mL). The aqueous layer is extracted with additional DCM (2×800 mL). The organic extractions are combined, dried over $MgSO_4$, filtered, and evaporated to give a pale yellow oil. Diol-4, 6.45 g, 60% is isolated by flash chromatography using solvents containing 1% $Et_3N$ from petroleum ether to petroleum ether/EtOAc (5:5) as eluent, as a light yellow oil.

TLC: $R_f$=0.45 (petroleum ether/EtOAc 6:4).

$^1$H NMR (400 MHz, $CDCl_2$) δ 1.24-1.32 (m, 4H, 2×$CH_2$), 1.54-1.57 (m, 4H, 2×$CH_2$), 1.93-1.96 (m, 2H, $CH_2$), 2.02-2.07 (m, 2H, $CH_2$), 2.96 (t, J=6.6 Hz, 2H, $CH_2$O), 3.54-3.59 (m, 2H, $CH_2$OH), 3.72 (s, 6H, 2×MeO), 5.29-5.32 (m, 2H, 2×=CH), 6.73-6.77 (m, 4H, Ph), 7.11-7.27 (m, 7H, Ph), 7.36-7.38 (m, 2H, Ph).

Step 5:

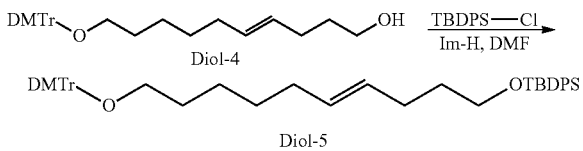

To a solution of Diol-4 (5.68 g, 12 mmol) and imidazole (Sigma Aldrich, 99%), (1.63 g, 24 mmol) in anhydrous DMF (100 mL), t-butyldiphenylsilyl chloride (Sigma Aldrich, 98%), (4.05 mL, 15.6 mmol) is added drop wise under $N_2$ atmosphere at room temperature. The reaction is stirred for 1 hour. TLC (petroleum ether/EtOAc 8:2) indicates that the starting material is fully consumed. A saturated aq. $NaHCO_3$ solution (500 mL) is added to quench the reaction. The resulting mixture is extracted with petroleum ether/EtOAc (2:1) (3×500 mL). The organic layers are combined, dried over $MgSO_4$, filtered, and evaporated to give a yellow oil. Diol-5, 8.14 g, 95% is isolated by flash chromatography using solvents containing 1% $Et_3N$ from petroleum ether to petroleum ether/EtOAc (9:1) as eluent, as a colourless oil.

TLC: $R_f$=0.7 (petroleum ether:EtOAc 8:2).

$^1$H NMR (400 MHz, $CDCl_3$): δ 0.97 (s, 9H, 3×Me), 1.19-1.30 (m, 4H, 2×$CH_2$), 1.48-1.55 (m, 4H, 2×$CH_2$), 1.91-1.95 (m, 2H, $CH_2$), 2.01-2.06 (m, 2H, $CH_2$), 2.95 (t, J=6.6 Hz, 2H, $CH_2$O), 3.58 (t, J=6.3 Hz, 2H, $CH_2$O), 3.70 (s, 6H, 2×MeO), 5.24-5.27 (m, 2H, 2×=CH), 6.72-6.75 (m, 4H, Ph), 7.11-7.37 (m, 15H, Ph), 7.57-7.60 (m, 4H, Ph).

Step 6:

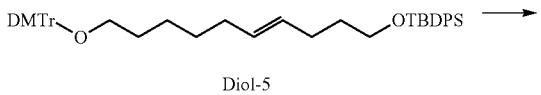

-continued

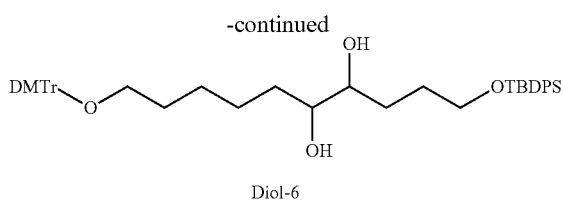

Diol-6

A mixture of diol-5 (9.27 g, 13 mmol), AD-mix-α (Sigma Aldrich), (18.2 g), methanesulfonamide (Sigma Aldrich, 97%), (1.23 g, 13 mmol), t-BuOH (65 mL) and water (65 mL) is stirred together vigorously at 55° C. for 14 h. The TLC analysis (petroleum ether:EtOAc 6:4) indicates ca. 95% consumption of the starting material. The reaction mixture is cooled to room temperature, treated with sodium sulfite (15.3 g, 12 mmol), then further stirred for 30 minutes. A saturated aq. NaHCO$_3$ solution (500 mL) is added to the reaction. The resulting mixture is extracted with EtOAc (3×500 mL). The organic layers are combined, dried over MgSO$_4$, filtered, and evaporated to give yellow oil. Diol-6, 7.96 g, 82%, is isolated by flash chromatography (silica gel, Fluka, 70-230 mesh) using solvents containing 1% Et$_3$N from petroleum ether to petroleum ether/EtOAc (1:1) as elutant, as a white solid.

TLC: R$_f$=0.3 (petroleum ether:EtOAc 6:4).

$^1$H NMR (400 MHz, CDCl$_3$) δ 1.07 (s, 9H, 3×Me), 1.41-1.7 (m, 12H, 6×CH$_2$), 1.94 (d, J=4.3 Hz, 1H, OH), 2.94-2.95 (m, 1H, OH), 3.06 (t, J=6.6 Hz, 2H, CH$_2$O), 3.61-3.63 (m, 2H, 2×CHOH), 3.73 (t, J=5.6 Hz, 2H, CH$_2$O), 3.81 (s, 6H, 2×MeO), 5.24-5.27 (m, 2H, 2×=CH), 6.82-6.85 (m, 4H, Ph), 7.21-7.47 (m, 15H, Ph), 7.57-7.60 (m, 4H, Ph).

Step 7:

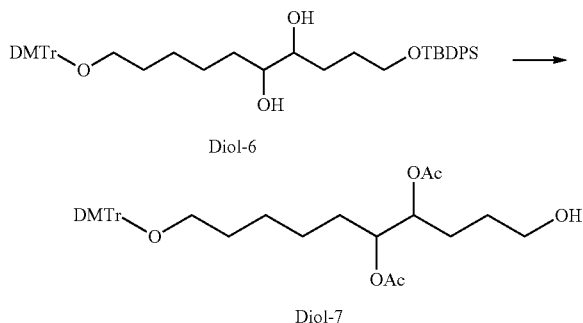

To a solution of diol-6 (7.96 g, 13 mmol) and DMAP (Sigma-Aldrich ReagentPlus™, 99%). (260 mg, 2.13 mmol) in a mixture of pyridine (15 mL) and DCM (30 mL), acetic anhydride (Fluka 99%), (2.5 mL, 26.68 mmol) is added at room temperature. TLC analysis (petroleum ether:EtOAc 6:4) indicates full consumption of the starting material after 1 h. The reaction is quenched by saturated aq. NaHCO$_3$ solution (500 mL). After 5 minutes, the mixture is extracted with DCM (3×500 mL). The organic layers are combined, dried over MgSO$_4$, filtered, and evaporated. The residue is co-evaporated with toluene (2×100 mL). The resulting yellow oil is subjected to a plug of silica gel (50 g, Fluka, 70-230 mesh) to remove DMAP using eluents containing 0.1% Et$_3$N from petroleum ether to petroleum ether/EtOAc (7:3) (250 mL each). The combined fractions of product are concentrated to dryness. The resulting colourless oil is dissolved in THF (100 mL) and treated with TBAF (Sigma-Aldrich; 5% wt water), (1 M in THF, 15 mL) at 0° C. The reaction solution is slowly warmed to room temperature and stirred for 2 hours. TLC analysis (petroleum ether:EtOAc 6:4) indicates that desilylation is completed. The volatile solvent (THF) is evaporated under reduced pressure at low temperature. A saturated aq. NaHCO$_3$ solution (500 mL) is added to the residue. The resulting mixture is extracted with EtOAc (3×500 mL). The organic layers are combined, dried over MgSO$_4$, filtered, and evaporated to give yellow oil. Diol-7, 4.2 g, 66%, is isolated by flash chromatography using solvents containing 1% Et$_3$N from petroleum ether to petroleum ether/EtOAc (1:1) as eluent, as a white solid.

TLC: R$_f$=0.45 (petroleum ether:EtOAc 1:1).

$^1$H NMR (400 MHz, CDCl$_3$) δ 1.29-1.33 (m, 4H, 2×CH$_2$), 1.47-1.63 (m, 8H, 4×CH$_2$), 1.99, 2.01 (2s, 6H, 2 MeC(O)), 3.00 (t, J=6.5 Hz, 2H, CH$_2$O), 3.60-3.64 (m, 2H, CH$_2$O), 3.75 (s, 6H, 2×MeO), 4.92-4.97 (m, 2H, 2×CHOAc), 6.76-6.80 (m, 4H, Ph), 7.15-7.29 (m, 7H, Ph), 7.38-7.40 (m, 2H, Ph).

Step 8:

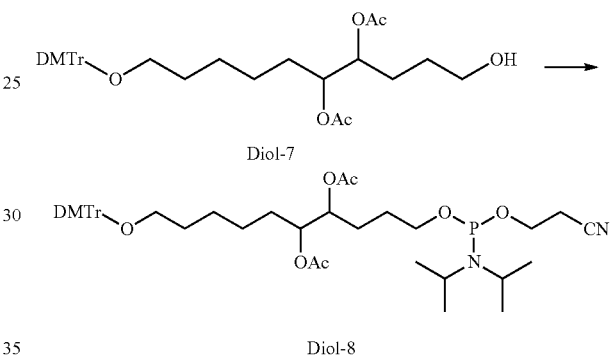

To a solution of diol-7 (2.08 g, 3.5 mmol) and diisopropylethylamine (Sigma Aldrich), (1.53 ml, 8.75 mmol) in DCM (17 mL), 2-cyanoethyl N,N-diisopropylchlorophosphor-amidite (1.0 g, 4.2 mmol) is added drop wise at room temperature under N$_2$. After stirring for 1 hour, TLC analysis (petroleum ether:EtOAc 4:6) indicates the full consumption of the starting material. The solvent (THF) is concentrated under reduced pressure. The resulting residue is subjected to chromatography directly. Diol-8, 2.5 g, 90%, is isolated by flash chromatography using solvents containing 1% Et$_3$N from petroleum ether to petroleum ether/EtOAc (1:1) as eluent, as a colourless syrup.

TLC: R$_f$=0.55 (petroleum ether: EtOAc 4:6).

$^1$H NMR (400 MHz, CDCl$_3$) δ 1.09, 1.10, 1.11, 1.12 (4 s, 12H, N(CHMe$_2$)$_2$), 1.26-1.31 (m, 4H, 2×CH$_2$), 1.45-1.56 (m, 8H, 4×CH$_2$), 1.95, 1.969, 1.971, 1.98 (4 s, 6H, 2 MeCO), 2.56 (t, J=6.5 Hz, 2H, CH$_2$CN), 2.95 (t, J=6.5 Hz, 2H, CH$_2$O), 3.49-3.55 (m, 4H, CH$_2$O), 3.72 (s, 6H, 2×MeO), 4.89-4.92 (m, 2H, 2×CHOAc), 6.74-6.76 (m, 4H, Ph), 7.13-7.25 (m, 7H, Ph), 7.34-7.37 (m, 2H, Ph).

$^{31}$P NMR (162 MHz, CDCl$_3$): 148.67, 148.69 ppm.

Example 6) Preparation of Clusters by Isothermal Amplification

Step 1: Hybridisation and Amplification

The DNA sequence used in the amplification process is the mixture of the two libraries prepared in Example 1, which have ends complementary to the grafted primers. The duplex DNA (1 nM) is denatured using 0.1 M sodium hydroxide treatment followed by snap dilution to the desired 0.2-2 pM 'working concentration' in 'hybridization buffer' (5×SSC/0.1% Tween).

Figure 10:
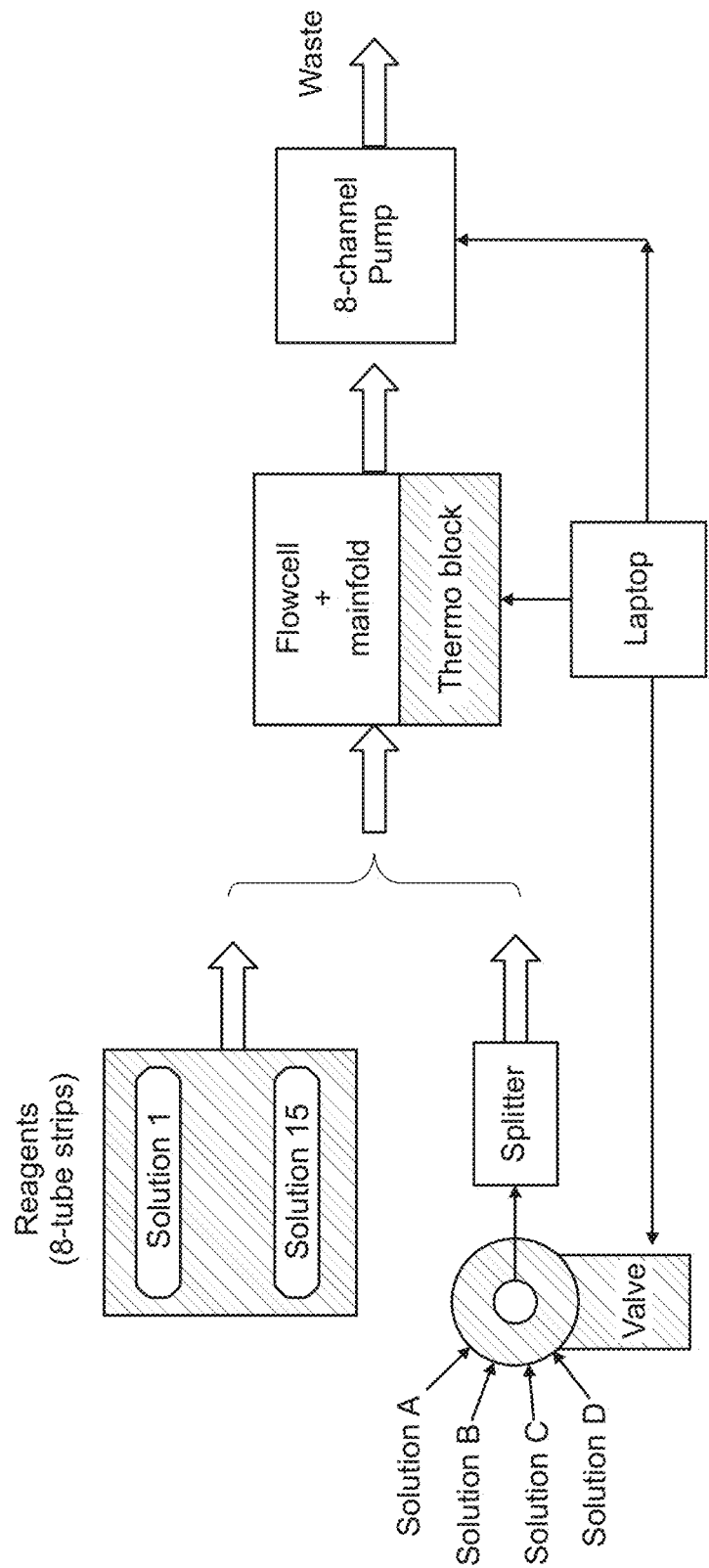
FIG. 10 shows a schematic of MJ Research thermocycler, coupled with an 8-way peristaltic pump Ismatec IPC ISM931 equipped with Ismatec tubing (orange/yellow, 0.51 mm ID).

Surface amplification was carried out by isothermal amplification using an MJ Research thermocycler, coupled with an 8-way peristaltic pump Ismatec IPC ISM931 equipped with Ismatec tubing (orange/yellow, 0.51 mm ID). A schematic of the instrument is shown in FIG. 10.

The single stranded template (denatured as indicated above) is hybridised to the grafted primers immediately prior to the amplification reaction, which thus begins with an initial primer extension step rather than template denaturation. The hybridization procedure begins with a heating step in a stringent buffer to ensure complete denaturation prior to hybridisation. After the hybridization, which occurs during a 20 minutes slow cooling step, the flowcell was washed for 5 minutes with a wash buffer (0.3×SSC/0.1% Tween).

A typical amplification process is presented in Table 1, which details the flow volumes per channel.

TABLE 1

Template Hybridization and 1st Extension

| Step | Description | T (° C.) | Time (sec) | Flow rate (µl/min) | Pumped V (µl) |
|---|---|---|---|---|---|
| 1 | Pump Hybridization pre-mix | 20 | 120 | 60 | 120 |
| 2 | Pump Hybridization mix | 98.5 | 300 | 15 | 75 |
| 3 | Remove bubbles | 98.5 | 10 | 100 | 16.7 |
| 4 | Stop flow and hold T | 98.5 | 30 | static | 0 |
| 5 | Slow cooling | 98.5-40.2 | 19.5 min | static | 0 |
| 6 | Pump wash buffer | 40.2 | 300 | 15 | 75 |
| 7 | Pump amplification pre-mix | 40.2 | 200 | 15 | 50 |
| 8 | Pump amplification mix | 40.2 | 75 | 60 | 75 |
| 9 | First Extension | 74 | 90 | static | 0 |
| 10 | cool to room temperature | 20 | 0 | static | 0 |

TABLE 2

Isothermal Amplification

| Step | Description | T (° C.) | Time (sec) | Flow rate (µl/min) | Pumped V (µl) |
|---|---|---|---|---|---|
| (1) | Pump Formamide | 60 | 75 | 60 | 75 |
| This sequence 35 times | Pump Amplification pre-mix | 60 | 75 | 60 | 75 |
| | Pump Bst mix | 60 | 95 | 60 | 95 |
| | Stop flow and hold T | 60 | 180 | static | 0 |
| 2 | Pump wash buffer | 60 | 120 | 60 | 120 |

Details are as follows: Hybridisation pre mix (buffer)=5× SSC/0.1% Tween; Hybridisation mix=0.1 M hydroxide DNA sample, diluted in hybridisation pre mix; Wash buffer=0.3×SSC/0.1% Tween; Amplification pre mix=2 M betaine, 20 mM Tris, 10 mM Ammonium Sulfate, 2 mM Magnesium sulfate, 0.1% Triton, 1.3% DMSO, pH 8.8; Amplification mix=2 M betaine, 20 mM Tris, 10 mM Ammonium Sulfate, 2 mM Magnesium sulfate, 0.1% Triton, 1.3% DMSO, pH 8.8 plus 200 µM dNTP's and 25 units/mL of Taq polymerase (NEB Product ref M0273L); Bst mix=2 M betaine, 20 mM Tris, 10 mM Ammonium Sulfate, 2 mM Magnesium sulfate, 0.1% Triton, 1.3% DMSO, pH 8.8 plus 200 µM dNTP's and 80 units/mL of Bst polymerase (NEB Product ref M0275L)

Step 2: Blocking Extendable 3'—OH Groups

To prepare the blocking pre-mix, 1530 µL of water and 170 µL of 10× blocking buffer (NEB buffer 4; product number B7004S) are mixed for a final volume of 1700 µL. To prepare the blocking mix, 1065.13 µL of blocking pre-mix, 21.12 µL of 125 µM ddNTP mix, and 13.75 µL of TdT terminal transferase (NEB; part no M0252S) are mixed for a final volume of 1100 µL.

To block the nucleic acid within the clusters formed in the flow cell channels, the computer component of the instrumentation flows the appropriate blocking buffer through the flow cell, and controls the temperature as shown in the exemplary embodiments below in Table 3.

| Step | Description | T (° C.) | Time (sec) | Flow rate (µl/min) | Pumped V (µl) |
|---|---|---|---|---|---|
| 1 | Pump Blocking pre-mix | 20 | 200 | 15 | 50 |
| 2 | Pump Blocking mix | 37.7 | 300 | 15 | 75 |
| 3 | Stop flow and hold T | 37.7 | 20 | static | 0 |
| 4 | Cyclic pump Blocking mix and wait | 37.7 | 8 × (20 + 180) | 15/ static | 45 |
| 5 | Pump wash buffer | 20 | 300 | 15 | 75 |

Example 7: Linearisation and Hybridization of a Sequencing Primer

To prepare the linearization mix, 1429 µL of water, 64 mg of sodium periodate, 1500 µL of formamide, 60 µL of 1M Tris pH8, and 6011.4 µL of 3-aminopropanol are mixed for a final volume of 3 mL. The periodate is first mixed with the water while the Tris is mixed with the formamide. The two solutions are then mixed together and the 3-aminopropanol is added to that mixture.

To linearize the nucleic acid within the clusters formed within the flow cell channels, 300 µL per channel of linearisation mix is flowed in at 15 µL/minutes at 20° C.; followed by 75 µL of water at the same flow rate.

To prepare the primer mix, 895.5 µL of hybridization buffer and 4.5 µl of sequencing primer (100 µM) are mixed to a final volume of 900 µL. The sequence of the sequencing primer used in the first reaction was:

(SEQ ID NO. 57)
5'-ACACTCTTTCCCTACACGACGCTCTTCCGATC

To denature the nucleic acid within the clusters and to hybridize the sequencing primer, the following reagents are flowed through the cell as shown in Table 4:

| Step | Description | T (° C.) | Time (sec) | Flow rate (µl/min) | Pumped V (µl) |
|---|---|---|---|---|---|
| 1 | Pump 0.1M NaOH | 20 | 300 | 15 | 75 |
| 2 | Pump TE | 20 | 300 | 15 | 75 |
| 3 | Pump Primer mix | 20 | 300 | 15 | 75 |
| 4 | Hold at 60 C. | 60 | 900 | 0 | 0 |
| 5 | Pump wash buffer | 40.2 | 300 | 15 | 75 |

Example 8: Sequencing from the Target Fragment

Sequencing of the clusters from the above illustrative protocol was carried out using modified nucleotides prepared as described in International patent application WO 2004/018493, and labeled with four spectrally distinct fluorophores, as described in U.S. application No. 60/801,270; filed May 18, 2006. Sequencing of clusters is described in more detail in patent WO06064199. The contents of the above-listed three documents are incorporated herein by reference in their entireties.

A mutant 9° N polymerase enzyme (an exo-variant including the triple mutation L408Y/Y409A/P410V and C223S) was used for the nucleotide incorporation steps.

Incorporation mix, Incorporation buffer (50 mM Tris-HCl pH 8.0, 6 mM MgSO4, 1 mM EDTA, 0.05% (v/v) Tween—20, 50 mM NaCl) plus 110 nM YAV exo-C223S, and 1 µM each of the four labeled modified nucleotides, was applied to the clustered templates, and heated to 45° C.

Templates were maintained at 45° C. for 30 minutes, cooled to 20° C. and washed with Incorporation buffer, then with 5×SSC/0.05% Tween 20. Templates were then exposed to Imaging buffer (100 mM Tris pH7.0, 30 mM NaCl, 0.05% Tween 20, 50 mM sodium ascorbate, freshly dissolved). Templates were scanned in 4 colors at room temperature. Templates were then exposed to sequencing cycles of Cleavage and Incorporation as follows:

Cleavage: Prime with Cleavage buffer (0.1M Tris pH 7.4, 0.1M NaCl and 0.05% Tween 20), 125 µL/channel; 60 µL/minutes.
Heat to 60° C.
Treat the clusters with Cleavage mix (100 mM TCEP in Cleavage buffer), 75 µL/channel; 60 µL/minutes.
Wait for a total of 15 minutes in addition to pumping fresh cleavage mix, 25 µL/channel; 60 µL/minutes, every 4 minutes.
Cool to 20° C.
Wash with Enzymology buffer.
Wash with 5×SSC/0.05% Tween 20.
Prime with Imaging buffer.
Scan in 4 colors at RT.
Incorporation: Prime with Incorporation buffer, 125 µL/channel; 60 µL/minutes, Heat to 60° C. Treat with Incorporation mix, 75 µL/channel; 60 µL/minutes. Wait for a total of 15 minutes in addition to pumping fresh Incorporation mix, 25 µL/channel; 60 µL/minutes, every 4 minutes.
Cool to 20° C.
Wash with Incorporation buffer, 75 µL/channel; 60 µL/minutes.
Wash with 5×SSC/0.05% Tween 20, 75 µL/channel; 60 µL/minutes
Prime with imaging buffer, 100 µL/channel; 60 µL/minutes
Scan in 4 colors at RT.
Repeat the process of Incorporation and Cleavage for as many cycles as required.

Incorporated nucleotides were detected using a Total Internal Reflection based fluorescent CCD imaging apparatus described in "Systems and Devices for Sequence by Synthesis Analysis," U.S. Ser. No. 60/788,248, filed Mar. 31, 2006.

Example 9) Sequencing the Tag

The first sequencing primer can be removed, and a second one applied using the same protocol as described in Example 7. The sequence of the second sequencing primer was as follows:

```
                                           (SEQ ID NO. 58)
5'-AGATCGGAAGAGCGGTTCAGCAGGAATGCCGAGACCG
```

The sequencing cycles described in Example 8 can be repeated to sequence the tag. In this case, only three cycles of sequencing were performed to analyse the tag. The data in FIG. 4 show that all the clusters sequenced aligned against a known sample (PhiX, BAC or E. coli contamination), and that for the samples that aligned correctly, 98% showed the correct tag. The 0.1% errors derive from mis-alignments of the target read, rather than errors in the tag sequences.

Example 10) 12-Plex Paired Reads from a Library of Fragments

Step 1) Grafting Primers onto Surface of SFA Coated Chip

An SFA coated chip is placed onto a modified MJ-Research thermocycler and attached to a peristaltic pump. Grafting mix consisting of 0.5 µM of a forward primer and 0.5 µM of a reverse primer in 10 mM phosphate buffer (pH 7.0) is pumped into the channels of the chip at a flow rate of 60 µl/minutes for 75 s at 20° C. The thermocycler is then heated to 51.6° C., and the chip is incubated at this temperature for 1 hour. During this time, the grafting mix undergoes 18 cycles of pumping: grafting mix is pumped in at 15 µl/minutes for 20 s, then the solution is pumped back and forth (5 s forward at 15 µl/minutes, then 5 s backward at 15 µl/minutes) for 180 s. After 18 cycles of pumping, the chip is washed by pumping in 5×SSC/5 mM EDTA at 15 µl/minutes for 300 s at 51.6° C. The thermocycler is then cooled to 20° C.

The primers are typically 5'-phosphorothioate oligonucleotides incorporating any specific sequences or modifications required for cleavage. Their sequences and suppliers vary according to the experiment for which they are to be used, and in this case were complementary to the 5'-ends of the template duplex. The DNA sequence used in this process was the pool of the twelve libraries, which have ends complementary to the grafted primers. The library mix was denatured using sodium hydroxide treatment followed by snap dilution as described.

The grafted primers contain a sequence of T bases at the 5'-end to act as a spacer group to aid linearisation and hybridization. The sequences of the three primers grafted to the chip are as follows:

```
Oligo A:
                                           (SEQ ID NO. 59)
5'-PS-TTTTTTTTTTAATGATACGGCGACCACCGAGAUCTACAC-3'
where U = 2-deoxyuridine;

Oligo B:
                                           (SEQ ID NO. 60)
5'-PS-TTTTTTTTTTCAAGCAGAAGACGGCATACGoxoA-3',
where Goxo = 8-oxoguanine).
```

Step 2) Preparation of Clusters by Isothermal Amplification:

The DNA sequence used in the amplification process is the mixture of the twelve libraries prepared in Example 1, which have ends complementary to the grafted primers. The duplex DNA (1 nM) is denatured using 0.1 M sodium hydroxide treatment followed by snap dilution to the desired 0.2-2 pM 'working concentration' in 'hybridization buffer' (5×SSC/0.1% Tween).

Surface amplification was carried out by isothermal amplification using a commercially available Solexa/Illumina cluster station as described in WO08002502. The cluster station is essentially a hotplate and a fluidics system for controlled delivery of reagents to a flow cell.

The single stranded template (denatured as indicated above) is hybridised to the grafted primers immediately prior to the amplification reaction, which thus begins with an initial primer extension step rather than template denaturation. The hybridization procedure begins with a heating step in a stringent buffer to ensure complete denaturation prior to hybridisation. After the hybridization, which occurs during a 20 minute slow cooling step, the flowcell was washed for 5 minutes with a wash buffer (0.3×SSC/0.1% Tween).

During template hybridization and first extension, a number of solutions/buffers are typically employed, e.g., a solution comprising the DNA samples, a hybridization buffer (5×SSC/0.1% Tween), a wash buffer (0.3×SSC/0.1% Tween), a 2M sodium hydroxide solution, a cluster buffer (200 mM Tris, 100 mM Ammonium Sulfate, 20 mM Magnesium sulfate, 1% Triton, 1.3% DMSO, pH 8.8); an amplification additive (5 M betaine), DNA polymerase, and 10 mM dNTP mix.

To prepare the hybridization mixes, a 0.2 ml strip sample tube and the hybridization buffer are pre-chilled. Using 1.7 ml Eppendorf tube(s), the DNA template(s) are then diluted to 1 nM in buffer EB (Qiagen). 1 µL of 2 M NaOH is added to 19 µL of template, vortexed briefly and incubated for 5 minutes at room temperature to denature the DNA template into single strands. The denatured DNA is diluted to working concentration (0.2-2 pM) in pre-chilled hybridization buffer (e.g. for 1 mL of 1 pM Hybridization mix, 1 µL of denatured DNA is diluted into 1 mL of pre-chilled hybridization buffer). The volume required depends on the number of channels used—at least 120 µL of hybridization mix per channel is optionally used. Thus, 1 mL of hybridization mix is enough for 8 channels. The samples are vortexed briefly, spun down and aliquoted into the pre-chilled 0.2 ml strip tubes (with no bubbles in the bottom of the tubes) and used immediately.

To prepare the Amplification pre-mix (of sufficient volume for the first extension and 35 cycles of isothermal amplification), 35 mL of H₂O (MilliQ), 7 mL of Cluster buffer (200 mM Tris, 100 mM Ammonium Sulfate, 20 mM Magnesium sulfate, 1% Triton, 1.3% DMSO, pH 8.8), and 28 mL of Amplification additive (5 M betaine solution) are mixed to achieve a final volume of 70 mL.

To prepare the first extension Taq mix, 780 µL of Amplification pre-mix, 16 µL of 10 mM dNTPs, and 4 µL of Taq DNA polymerase are mixed together for a final volume of 800 µl.

A typical amplification process is detailed in Table 1, which includes the flow volumes per channel, controlled automatically by the computer component of the invention.

TABLE 1

Template hybridization and first extension.

| Step | Description | T (° C.) | Time (sec) | Flow rate (µl/min) | Pumped V (µl) |
|---|---|---|---|---|---|
| 1 | Pump Hybridization pre-mix | 20 | 120 | 60 | 120 |
| 2 | Pump Hybridization mix | 96 | 300 | 15 | 75 |
| 3 | Remove bubbles | 96 | 6 | 100 | 10 |
| 4 | Stop flow and hold T | 96 | 30 | static | 0 |

TABLE 1-continued

Template hybridization and first extension.

| Step | Description | T (° C.) | Time (sec) | Flow rate (µl/min) | Pumped V (µl) |
|---|---|---|---|---|---|
| 5 | Slow cooling | 96-40 | 1120 | static | 0 |
| 6 | Pump wash buffer | 40 | 300 | 15 | 75 |
| 7 | Pump amplification pre-mix | 40 | 280 | 15 | 70 |
| 8 | Pump amplification mix | 40 | 95 | 60 | 95 |
| 9 | First Extension | 74 | 90 | static | 0 |
| 10 | cool to room temperature | 20 | 0 | static | 0 |

Isothermal Amplification at 60° C. Using Formamide as Denaturant

The copied DNA can be isothermally amplified into clusters at 60° C. using formamide as a denaturant. The isothermal amplification (including both temperature control and reagent control) is overseen by the computer component. Table 2 gives outlines of exemplary script controls. After the isothermal amplification, and optional washing step occur, the nucleic acid of the clusters is ready to be linearized (see below).

TABLE 2

Isothermal amplification

| Step | Description | T (° C.) | Time (sec) | Flow rate (µl/min) | Pumped V (µl) |
|---|---|---|---|---|---|
| (1) | Pump Formamide | 60 | 56 | 30 | 28 |
| This sequence 35 times | Pump Amplification pre-mix | 60 | 56 | 30 | 28 |
|  | Pump Bst mix | 60 | 72 | 30 | 36 |
| 2 | Pump wash buffer | 60 | 280 | 30 | 140 |
| 3 | Pump Storage Buffer | 20 | 380 | 15 | 95 |

Wash buffer=0.3×SSC/0.1% Tween
Amplification pre mix=2 M betaine, 20 mM Tris, 10 mM Ammonium Sulfate, 2 mM Magnesium sulfate, 0.1% Triton, 1.3% DMSO, pH 8.8
Bst mix=2 M betaine, 20 mM Tris, 10 mM Ammonium Sulfate, 2 mM Magnesium sulfate, 0.1% Triton, 1.3% DMSO, pH 8.8 plus 200 µM dNTPs and 80 units/mL of Bst polymerase (NEB Product ref M0275L)
Storage Buffer=5×SSC.

Step 3) Preparation of Clusters for First Sequencing Read

The preparation for read one was performed on the Illumina cluster station. All volumes used in the protocol were 95 µl per lane unless otherwise stated. Linearisation of A-type surface immobilised oligonucleotides was achieved by incubation with USER enzyme mix (cocktail of Uracil DNA Glycosylase and Endonuclease VIII, NEB #M5505, 10 U/ml, 10 mM KCl, 20 mM Tris pH 8.8, 10 mM (HN4)2SO4, 2 mM MgSO4, 0.1% Triton X-100, 37° C., 30 minutes). All exposed 3'-OH termini of DNA, either from the extended template or unextended surface oligonucleotides were blocked by dideoxy chain termination using a cocktail of terminal transferase (0.25 U/µl) and a modified polymerase (SBS polymerase as described below) (0.015 mg/ml, 100 µM ddNTP, 50 mM tris, 50 mM NaCl, 6 mM MgSO4, 1 mM EDTA, 0.05% Tween 20). Blocking was achieved in a two stage protocol, initial incubation at 37° C. for 30 minutes followed by a ramping to 60° C. and incubating the flowcell for a further 15 minutes). Linearised and blocked clusters were washed with 0.3×SSC and storage buffer prior to denaturation with 0.1N NaOH. Denatured clusters were neutralised with TE buffer (10 mM Tris pH 8.0, 1 mM EDTA) and washed with storage buffer. The read 1 specific sequencing primer (SEQ ID NO. 61)
(5'-ACACTCTTTCCCTACACGACGCTCTTCCGATC-3', 0.5 µM in hybridisation buffer) was annealed to the clusters by incubation at 60° C. for 15 minutes, followed by a 0.3×SSC wash at 40° C. (ramp rate 1° C./sec). The flowcell was finally flushed with storage buffer (at 20° C.). Processed flowcells were transferred to the Illumina Genome Analyser for sequencing read 1.

Step 4) Sequencing from the Target Fragment

Sequencing of the clusters from the above illustrative protocol was carried out using modified nucleotides prepared as described in International patent application WO 2004/018493, and labeled with four spectrally distinct fluorophores, as described in PCT application number PCT/GB2007/001770, published as WO07135368. Sequencing of clusters is described in more detail in WO06064199. The contents of the above-listed documents are incorporated herein by reference in their entireties.

A mutant 9° N polymerase enzyme (an exo-variant including the triple mutation L408Y/Y409A/P410V and C223S) (SBS polymerase) was used for the nucleotide incorporation steps.

All processes were conducted as described in the Illumina Genome Analyser operating manual. The flowcell was mounted to the analyser, primed with sequencing reagents: position #1=incorporation mix (1 µM dNTP mix, 0.015 µg/ml SBS polymerase, 50 mM Tris pH 9.0, 50 mM NaCl, 6 mM MgSO4, 1 mM EDTA, 0.05% Tween 20); position #2=spare (MilliQ water only); position #3=scan mix (100 mM Tris pH 7.0, 50 mM sodium acsorbate); position #4=High salt wash (5×SSC, 0.05% Tween 20); position #5=incorporation buffer (50 mM Tris pH 9.0, 50 mM NaCl, 1 mM EDTA, 0.05% Tween 20); position #6=cleavage mix (100 mM TCEP, 100 mM Tris pH 9.0, 100 mM NaCl, 50 mM sodium ascorbate, 0.05% Tween 20); position #7=cleavage buffer (100 mM Tris pH 9.0, 100 mM NaCl, 0.05% Tween 20); position #8=spare (single reads) or connected to PE module outlet (paired read experiments). Flowcells were sequenced using standard sequencing recipes for either 27- or 37-cycle experiments. Data was analysed using the standard analysis pipeline.

Incorporation: Prime with Incorporation buffer, 125 µL/channel; 60 µL/minutes, Heat to 60° C.
Treat with Incorporation mix, 75 µL/channel; 60 µL/minutes.
Wait for a total of 15 minutes in addition to pumping fresh Incorporation mix, 25 µL/channel; 60 µL/minutes, every 4 minutes.
Cool to 20° C.
Wash with Incorporation buffer, 75 µL/channel; 60 µL/minutes.
Wash with 5×SSC/0.05% Tween 20, 75 µL/channel; 60 µL/minutes
Prime with imaging buffer, 100 µL/channel; 60 µL/minutes
Scan in 4 colors at RT.
Cleavage: Prime with Cleavage buffer (0.1M Tris pH 7.4, 0.1M NaCl and 0.05% Tween 20), 125 µL/channel; 60 µL/minutes.
Heat to 60° C.
Treat the clusters with Cleavage mix (100 mM TCEP in Cleavage buffer), 75 µL/channel; 60 µL/minutes.
Wait for a total of 15 minutes in addition to pumping fresh cleavage mix, 25 µL/channel; 60 µL/minutes, every 4 minutes.
Cool to 20° C.
Wash with Enzymology buffer.
Wash with 5×SSC/0.05% Tween 20.

Repeat the process of Incorporation and Cleavage for as many cycles as required.

Incorporated nucleotides were detected using the Illumina genome analyzer, a Total Internal Reflection based fluorescent CCD imaging apparatus described in "Systems and Devices for Sequence by Synthesis Analysis," U.S. Ser. No. 60/788,248, filed Mar. 31, 2006 and corresponding PCT application PCT/US07/07991, published as WO07123744, the contents of which are incorporated herein by reference in their entireties.

Step 5) Sequencing of the Tag

Following the successful completion of sequencing the first read on the Genome Analyser, flowcells remained mounted and were prepared for tag sequencing in situ, using the Illumina Paired End module. Temperature control was achieved by using the Genome Analyser peltier. All flow rates were 60 µl/min and 75 µl per lane unless otherwise stated. Clusters were denatured with 0.1 M NaOH to remove the extended sequencing primer from read 1. Hybridisation of the tag sequencing primer (SEQ ID NO. 62)
(5'-GATCGGAAGAGCACACGTCTGAACTCCAGTCAC-3'), 0.5 µM in hybridisation buffer) as described for read 1. Sequencing of the tag was performed on the Illumina Genome Analyser.

Step 6) Preparation of the Clusters for the Paired Sample Read

Following the successful completion sequencing of two reads on the Genome Analyser, flowcells remained mounted and were prepared for paired read 2 in situ, using the Illumina Paired End module. Temperature control was achieved by using the Genome Analyser peltier. All flow rates were 60 µl/min and 75 µl per lane unless otherwise stated. Clusters were denatured with 0.1 M NaOH to remove the extended sequencing primer from the tag sequencing. Clusters were 3'-dephosphorylated using T4 polynucleotide kinase (Invitrogen #18004-010, 200 U/ml, 50 mM imidazole pH 6.4, 12 mM MgCl2, 70 µM ADP, 1 mM 2-mercaptoethanol, 37° C., 30 minutes), prior to re-synthesis of the A-strand achieved using 15 cycles of 60° C. isothermal amplification (same reagents and conditions as described for cluster creation except conducted at 30 µl/min). Clusters were washed before and after resynthesis with 0.3×SSC (150 µl and 245 µl respectively). Linearisation of the B-strand of the re-synthesised clusters was achieved by the excision of 8-oxoguanine from the B-type oligo using Fpg (formamidopyrimidine DNA glycosylase, NEB #M0240, 80 U/ml, 10 mM Bis Tris propane pH 7.0, 10 mM MgCl2, 1 mM dithiothreitol, 37° C., 30 minutes). Blocking was performed as described for read 1 using the same blocking cocktail. Linearised and blocked clusters were denatured prior to hybridisation of the read 2 specific sequencing primer (SEQ ID NO. 63)
(5'-GTGACTGGAGTTCAGACGTGTGCTCTTCCGATC-3'), 0.5 µM in hybridisation buffer) as described for read 1. Read 2 of the processed flowcells was subsequently sequenced on the Illumina Genome Analyser.

Data generated from the 12 samples is shown in FIG. 8. In each case the tag sequence could unambiguously determine the source of the sample. Each sample from the 12 was represented by a reasonable number of clusters, and for each tag read, the large majority (>90%) of the reads aligned against the source genome identified by the tag.

While the foregoing invention has been described in some detail for purposes of clarity and understanding, it will be clear to one skilled in the art from a reading of this disclosure that various changes in form and detail can be made without departing from the true scope of the invention. For example, all the techniques and apparatus described above may be used in various combinations. All publications, patents, patent applications, or other documents cited in this application are incorporated by reference in their entirety for all purposes to the same extent as if each individual publication, patent, patent application, or other document were individually indicated to be incorporated by reference for all purposes.

The invention claimed is:

1. A method for sequencing nucleic acid sequences and identifying subsets of nucleic acid sequences, each subset of nucleic acid sequences isolated from a different source, the method comprising the steps of:
   (a) providing at least two different samples of randomly fragmented double stranded nucleic acid targets, wherein each of the randomly fragmented double stranded nucleic acid targets is isolated from a different source;
   (b) ligating a sample specific tagged adaptor to each end of each target fragment of each sample to generate adaptor-target-adaptors, wherein the tagged adaptor comprises at least one region of single stranded nucleic acid and a region of double stranded nucleic acid comprising a sample specific tag sequence that differentiates adaptor-target-adaptors originating from different samples, and wherein the sample specific tag sequence is attached directly to the target fragment in each adaptor-target-adaptor with no intervening nucleotides;
   (c) amplifying the adaptor-target-adaptors of each sample with a pair of amplification primers complementary to the sample specific tag sequence to generate amplified adaptor-target-adaptors from each sample;
   (d) pooling the amplified adaptor-target-adaptors of the at least two different samples;
   (e) immobilizing the pooled adaptor-target-adaptors on a surface;
   (f) sequencing the immobilized adaptor-target-adaptors on the surface to determine a sequence read of each immobilised adaptor-target-adaptor and identify the sample specific tag sequence of each immobilised adaptor-target-adaptor, thereby determining nucleic acid sequences of the immobilized adaptor-target-adaptors and identifying each of the immobilized adaptor-target-adaptors as a member of a subset of nucleic acid sequences.

2. The method of claim 1, wherein the sequencing of the target fragment and the sample specific tag sequence is performed in a single sequencing read.

3. The method of claim 1, wherein the sequencing of the target fragment and the sample specific tag sequence is performed in two sequencing reads.

4. The method of claim 3, wherein the solid surface is a flow cell or a collection of beads.

5. The method of claim 4, wherein the beads are isolated as single beads in an emulsion.

6. The method of claim 1, wherein the immobilized adaptor-target-adaptors are amplified on the solid surface prior to sequencing to generate an amplified array.

7. The method of claim 6, wherein the amplified array is a clustered array of amplified single molecules.

8. The method of claim 7, wherein the clustered array is formed by solid-phase nucleic acid amplification.

9. The method of claim 8, wherein the clustered array is formed by isothermal solid-phase nucleic acid amplification.

10. The method of claim 1, wherein the sequencing step comprises cycles of ligation with labelled oligonucleotides.

11. The method of claim 10, wherein the oligonucleotides are labelled with fluorophores.

12. The method of claim 1, wherein the sequencing comprises cycles of addition of nucleotides.

13. The method of claim 12, wherein the nucleotides are labelled.

14. The method of claim 13, wherein the nucleotides are labelled with fluorophores.

15. The method of claim 1, wherein the sequencing step is carried out on a flow cell or an array of immobilised beads.

16. The method of claim 1, wherein the immobilized adaptor-target-adaptors undergo a sequencing reaction from both ends to obtain a paired end read.

17. The method of claim 16, further comprising synthesizing a complementary copy of the immobilized adaptor-target-adaptors and sequencing the opposite end of the complementary copy.

18. The method of claim 17, wherein the opposite end of the complementary copy is sequenced after the sample specific tag sequence is determined.

\* \* \* \* \*